US005821246A

United States Patent [19]
Brown et al.

[11] Patent Number: 5,821,246
[45] Date of Patent: Oct. 13, 1998

[54] ANILINE DERIVATIVES

[75] Inventors: Dearg Sutherland Brown; Jeffrey James Morris; Andrew Peter Thomas, all of Macclesfield, United Kingdom

[73] Assignee: Zeneca Limited, London, United Kingdom

[21] Appl. No.: 836,362

[22] PCT Filed: Nov. 8, 1995

[86] PCT No.: PCT/GB95/02606

§ 371 Date: May 12, 1997

§ 102(e) Date: May 12, 1997

[87] PCT Pub. No.: WO96/15118

PCT Pub. Date: May 23, 1996

[30] Foreign Application Priority Data

Nov. 12, 1994 [GB] United Kingdom ................... 9422866
Apr. 7, 1995 [GB] United Kingdom ................... 9507308

[51] Int. Cl.$^6$ ..................... A61K 31/51; A61K 31/535; C07D 403/00; C07D 239/82
[52] U.S. Cl. ..................... 514/253; 514/259; 544/284; 544/293
[58] Field of Search ................... 544/293, 284; 514/259, 253

[56] References Cited

U.S. PATENT DOCUMENTS

| 3,266,990 | 8/1966 | Lutz et al. | 514/259 |
| 4,343,940 | 8/1982 | Kreighbaum et al. | 514/259 |

FOREIGN PATENT DOCUMENTS

| 0 326 307 | 2/1989 | European Pat. Off. . |
| 0 326 330 A2 | 8/1989 | European Pat. Off. . |
| 0 520 722 A1 | 12/1992 | European Pat. Off. . |
| 0 566 226 A1 | 10/1993 | European Pat. Off. . |
| 0 602 851 A1 | 6/1994 | European Pat. Off. . |
| 0 635 498 A1 | 1/1995 | European Pat. Off. . |
| 0 635 507 A1 | 1/1995 | European Pat. Off. . |
| 0 682 027 A1 | 11/1995 | European Pat. Off. . |
| 0 787 722 A1 | 8/1997 | European Pat. Off. . |
| 2 033 894 | 5/1980 | United Kingdom . |
| 2 160 201 | 12/1985 | United Kingdom . |
| WO 97/13760 | 4/1977 | WIPO . |
| WO 97/13771 | 4/1977 | WIPO . |
| WO 92/14816 | 9/1992 | WIPO . |
| WO 92/20642 | 11/1992 | WIPO . |
| WO 95/06648 | 3/1995 | WIPO . |
| 95/15758 | 6/1995 | WIPO . |
| WO 95/15952 | 6/1995 | WIPO . |
| WO 95/19169 | 7/1995 | WIPO . |
| WO 95/19774 | 7/1995 | WIPO . |
| WO 95/19970 | 7/1995 | WIPO . |
| WO 95/21613 | 8/1995 | WIPO . |
| WO 95/23141 | 8/1995 | WIPO . |
| WO 95/24190 | 9/1995 | WIPO . |
| WO 96/07657 | 3/1996 | WIPO . |
| WO 96/09294 | 3/1996 | WIPO . |
| WO 96/15118 | 5/1996 | WIPO . |
| WO 96/16960 | 6/1996 | WIPO . |
| WO 96/29331 | 9/1996 | WIPO . |
| WO 96/30347 | 10/1996 | WIPO . |
| WO 96/31510 | 10/1996 | WIPO . |
| WO 96/33977 | 10/1996 | WIPO . |
| WO 96/33978 | 10/1996 | WIPO . |
| WO 96/33979 | 10/1996 | WIPO . |
| WO 96/33980 | 10/1996 | WIPO . |
| WO 96/33981 | 10/1996 | WIPO . |
| WO 96/34867 | 11/1996 | WIPO . |
| WO 96/35689 | 11/1996 | WIPO . |
| WO 96/39145 | 12/1996 | WIPO . |
| WO 96/40142 | 12/1996 | WIPO . |
| WO 96/40648 | 12/1996 | WIPO . |
| WO 97/02266 | 1/1997 | WIPO . |
| WO 97/03069 | 1/1997 | WIPO . |
| WO 97/18212 | 5/1997 | WIPO . |

OTHER PUBLICATIONS

Rewcastle et al., "Tyrosine Kinase Inhibitors. 5. Synthesis and Structure–Activity Relationships for 4–[(Phenylmethyl)amino]–and 4–(Phenylamino)quinazolines as Potent Adenosine 5'–Triphosphate Binding Site Inhibitors of the Tyrosine Kinase Domain of the Epidermal Growth Factor Receptor," J.Med.Chem. 1995, vol. 38, pp. 3482–3487.

Burke, Jr., "Protein–tyrosine kinase inhibitors," Drugs of the Future 1992, vol. 17(2), pp. 119–131.

Spence, "Inhibitors of Tyrosine Kinase Activity as Anticancer Therapeutics: Recent Developments," Expert Opinion in Therapeutic Patents, Jan. 1993, Patent Update, Anticancers, etc., pp. 3–9, Current Drugs Ltd ISSN 0962–2594,.

Spada et al., Small molecule inhibitors of tyrosine Kinase activity, Exp.Opin.Ther.Patents (1995), 5(8):805–817, Patent Update, Oncologic, Endocrine & Metabolic, Ashley Publications Ltd ISSN 1354–3776.

(List continued on next page.)

Primary Examiner—Matthew V. Grumbling
Attorney, Agent, or Firm—Cushman Darby & Cushman Intellectual Property Group of Pillsbury Madison & Sutro, LLP

[57] ABSTRACT

The invention concerns aniline derivatives of formula I wherein m is 1, 2 or 3, n is 0, 1, 2 or 3, Q is phenyl or naphthyl or a 5- or 6-membered heteroaryl moiety containing 1, 2 or 3 heteroatoms selected from oxygen, nitrogen and sulfur, and X, $R^1$ and $R^2$ are defined in the claims; or pharmaceutical compositions containing them, and the methods of using the compounds as tyrosine kinase inhibitors and for the treatment of proliferative diseases such as cancer.

13 Claims, No Drawings

OTHER PUBLICATIONS

Bridges, "The current status of tyrosine kinase inhibitors: do the diarylamine inhibitors of the EGF receptor represent a new beginning?," Exp.Opin.Ther.Patents (1995), 5(12): 1245–1257, Editorial, Oncologic, Endocrine & Metabolic, 1995 Ashley Publications Ltd ISSN 1354–3776.

Traxler et al., "Recent advances in protein tyrosine kinase inhibitors," Drugs of the Future 1995, vol. 20(12, pp. 1261–1274.

Iyer et al., "Studies in Potential Amoebicides: Part III–Synthesis of $_4$–Substituted Amino–8–Hydroxy) Quinazolines & $_3$–Substituted 8–Hydroxy(&8–Methoxy)–$_4$–Quinazolones," J.Sci.Industr.Res., vol. 15C, Jan. 1956, pp. 1–7.

Kobayashi, Derwent Abstract 82–87077, vol. 6, No. 244, Dec. 1982, JP 57–144266, Sep. 1982, "4–Anilinoquinazoline Derivative, its Preparation and Analgesic and Antiphlogistic Agent Containing Said Derivative as Active Component".

Sankyo and Ube, Derwent Abstract 81–28290, JP 56–20577, Feb. 1981, "4–(N–alkyl:anilino) quinazoline derivs . . . having analgesic and antiinflammatory actions".

Kyorin, Derwent Abstract 84–53835, JP 59–13765, Jan. 1984, "2–(4–Quinazolinyl)amino benzoic acid derivs . . . having analgesic and antiinflammatory activities".

Li et al., Chem.Abs., vol. 92:76445u, 1980, pp. 674–675.

Lin et al., Chem.Abs., vol. 96:122728w, 1982, p. 695.

Fry et al., "Specific Inhibitor of the Epidermal Growth Factor Receptor Tyrosine Kinase," Science, vol. 265, Aug. 19, 1994, pp. 1093–1095.

Buchdunger et al., "–4,5–Dianilinophthalimide: A protein–tyrosine kinase inhibitor with selectivity for the epidermal growth factor receptor signal transduction pathway and potent in vivo antitumor activity," Proc.Natl.Acad.Sci., USA, vol. 91, pp. 2334–2338, Mar. 1994, Applied Biological Sciences.

Trinks et al., "Dianilinophthalimides: Potent and Selective, ATP–Competitive Inhibitors of the EGF–Receptor Protein Tyrosine Kinase," J.Med. Chem. 1994, vol. 37, pp. 1015–1027.

Maguire et al., "A New Series of PDGF Receptor Tyrosine Kinase Inhibitors: 3–Substituted Quinoline Derivatives," J.Med.Chem. 1994, vol. 37, pp. 2129–2137.

Dolle et al., "5,7–Dimethoxy–3–(4–pyridinyl)quinoline Is a Potent and Selective Inhibitor of Human Vascular β–Type Platelet–Derived Growth Factor Receptor Tyrosine Kinase," J.Med.Chem. 1994, vol. 37, pp. 2627–2629.

Senger et al., "Vascular Permeability Factor (VPF, VEGF) in Tumor Biology, "Cancer and Metastasis Review, vol. 12, 1993, pp. 303–324.

Ward et al., "Epidermal Growth Factor Receptor Tyrosine Kinase –Investigation of Catalytic Mechanism, Structure–Based Searching and Discovery of a Potent Inhibitor," Parmacology, vol. 48, No. 4, pp. 659–666 (1994).

Kolch et al., "Regulation of the Expression of the VEGF/VPS and its Receptors: Role in Tumor Angiogenesis," Breast Cancer Research and Treatment, vol. 36, 1995, pp. 139–155.

Connolly, et al., "Human Vascular Permeability Factor," J.Bio.Chem., vol. 264, No. 33, Nov. 1989, pp. 20017–20024.

Cullinan–Bove, et al., "Vascular Endothelial Growth Factor/Vascular Permeability Factor Expression in the Rat Uterus . . . ," Endocrinology, vol. 133, No. 2, 1993, pp. 829–837.

Fan et al., "Controlling the Vasculature: Angiogenesis, Anti–Angiogenesis . . . ," TiPS Review, vol. 16, Feb. 1995, pp. 57–65.

Folkman, "Angiogenesis in Cancer, Vascular, Rheumatoid and Other Disease," Nature Medicine, vol. 1, No. 1, 1995, pp. 27–30.

Jakeman et al., "Developmental Expression of Binding Sites and Messenger Ribonucleic Acid . . . ," Endocrinology, vol. 133, No. 2, 1993, pp. 848–859.

Kim et al., "Inhibition of Vascular Endothelial Growth Factor–Induced Angiogenesis Suppresses Tumour Growth in Vivo," Nature, vol. 362, Apr. 1993, pp. 841–844.

Bridges et al: Enantioselective Inhibition of the Epidermal Growth Factor Receptor Tyrosine Kinase by 4–(α–Phenethylamino) quinazoline, Bioorganic & Medicinal Chemistry, vol. 3, No. 12, pp. 1651–1656, (1995).

Agrawal: "Studies on Potential Filaricides; Part XI", Chemical Abstracts, vol. 95, No. 1, 1981, abstract No. 7199s, pp. 682–683; see abstract & Indian J. Chem. Sect. B, vol. 19B, No. 12, 1980 India pp. 1084–1087.

ANILINE DERIVATIVES

The invention relates to aniline derivatives, or pharmaceutically-acceptable salts thereof, which possess anti-proliferative activity such as anti-cancer activity and are accordingly useful in methods of treatment of the human or animal body. The invention also relates to processes for the manufacture of said aniline derivatives, to pharmaceutical compositions containing them and to their use in the manufacture of medicaments of use in the production of an anti-proliferative effect in a warm-blooded animal such as man.

many of the current treatment regimes for cell proliferation diseases such as psoriasis and cancer utilise compounds which inhibit DNA synthesis. Such compounds are toxic to cells generally but their toxic effect on rapidly dividing cells such as tumour cells can be beneficial. Alternative approaches to anti-proliferative agents which act by mechanisms other than the inhibition of DNA synthesis have the potential to display enhanced selectivity of action.

In recent years it has been discovered that a cell may become cancerous by virtue of the transformation of a portion of its DNA into oncogene i.e. a gene which, on activation, leads to the formation of malignant tumour cells (Bradshaw, *Mutagenesis*, 1986, 1, 91). Several such oncogenes give rise to the production of peptides which are receptors for growth factors. The growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988, 57, 443; Larsen et al. *Ann. Reports in Med. Chem.* 1989, Chpt. 13).

Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research*, 1993, 60, 43–73) based on families of growth factors which bind to different receptor tyrosine kinases. The classification includes Class I receptor tyrosine kinases comprising the EGF family of receptor tyrosine kinases such as the EGF, transforming growth factor α (TGFα), NEU, erbB, Xmrk, DER and let23 receptors, Class II receptor tyrosine kinases comprising the insulin family of receptor tyrosine kinases such as the insulin, IGFI and insulin-related receptor (IRR) receptors and Class III receptor tyrosine kinases comprising the platelet-derived growth factor (PDGF) family of receptor tyrosine kinases such as the PDGFα, PDGFβ and colony-stimulating factor 1 (CDF1) receptors. It is known that Class I kinases such as the EGF family of receptor tyrosine kinases are frequently present in common human cancers such as breast cancer (Sainsbury et al., *Brit. J. Cancer*, 1988, 58, 458; Guerin et al., *Oncogene Res.*, 1988, 3, 21), squamous cell cancer of the lung (Hendler et al., *Cancer Cells*, 1989, 7, 347), bladder cancer (Neal et al., *Lancet*, 1985, 366), oesophageal cancer (Mukaida et al., *Cancer*, 1991, 68, 142), gastrointestinal cancer such as colon, rectal or stomach cancer (Bolen et al., *Oncogene Res.*, 1987, 1, 149), leukaemia (Konaka et al., *Cell*, 1984, 37, 1035) and ovarian, bronchial or pancreatic cancer (European Patent Specification No. 0400586). As further human tumour tissues are tested for the EGF family of receptor tyrosine kinases it is expected that their widespread prevalance will be established in further cancers such as thyroid and uterine cancer. It is also known that EGF type tyrosine kinase activity is rarely detected in normal cells whereas it is more frequently detectable in malignant cells (Hunter, *Cell*, 1987, 50, 823). It has been shown more recently (W. J. Gullick, *Brit. Med. Bull.*, 1991, 47, 87) that EGF receptors which possess tyrosine kinase activity are overexpressed in many human cancers such as brain, lung squamous cell, bladder, gastric, colorectal, breast, head and neck, oesophageal, gynaecological and thyroid tumours.

Accordingly it has been recognised that an inhibitor of receptor tyrosine kinases should be of value as a selective inhibitor of the growth of mammalian cancer cells (Yaish et al. *Science*, 1988, 242, 933). Support for this view is provided by the demonstration that erbstatin, an EGF receptor tyrosine kinase inhibitor, specifically attenuates the growth in athymic nude mice of a transplanted human mammary carcinoma which expresses EGF receptor tyrosine kinase but is without effect on the growth of another carcinoma which does not express EGF receptor tyrosine kinase (Toi et al., *Eur. J. Cancer Clin. Oncol.*, 1990, 26, 722.) Various derivatives of styrene are also stated to possess tyrosine kinase inhibitory properties (European Patent Application Nos. 0211363, 0304493 and 0322738) and to be of use as anti-tumour agents. The in vivo inhibitory effect of two such styrene derivatives which are EGF receptor tyrosine kinase inhibitors has been demonstrated against the growth of human squamous cell carcinoma inoculated into nude mice (Yoneda et al., *Cancer Research*, 1991, 51, 4430). Accordingly it has been indicated that Class I receptor tyrosine kinase inhibitors will prove to be useful in the treatment of a variety of human cancers. Various known tyrosine kinase inhibitors are disclosed in a more recent review by T. R. Burke Jr. (*Drugs of the Future*, 1992, 17, 119).

It is also expected that inhibitors of EGF type receptor tyrosine kinases will be useful in the treatment of other diseases of excessive cellular proliferation such as psoriasis (where TGFA is believed to be the most important growth factor) and benign prostatic hypertrophy (BPH).

We have now found that certain aniline derivatives possess anti-proliferative properties which are believed to arise from their Class I receptor tyrosine kinase inhibitory properties.

It is known from European Patent Applications Nos. 0520722 and 0566226 that certain quinazoline derivatives which bear an anilino substituent at the 4-position possess receptor tyrosine kinase inhibitory activity. It is further known from European Patent Application No. 0602851 that certain quinazoline derivatives which bear a heteroarylamino substituent at the 4-position also possess receptor tyrosine kinase inhibitory activity.

It is further known from International Patent Application WO 92/20642 that certain aryl and heteroaryl compounds inhibit EGF and/or PDGF receptor tyrosine kinase. There is the disclosure of certain quinazoline derivatives therein but no mention is made of 4-anilinoquinazoline derivatives.

It is further known from European Patent Application No. 0635507 that certain tricyclic compounds which comprise a 5- or 6-membered ring fused to the benzo-ring of a quinazoline possess receptor tyrosine kinase inhibitory activity. It is also known from European Patent Application No. 0635498 that certain quinazoline derivatives which carry an amino group at the 6-position and a halogeno group at the 7-position possess receptor tyrosine kinase inhibitory activity.

The in vitro anti-proliferative effect of a 4-anilinoquinazoline derivative has been disclosed by Fry et al., *Science*, 1994, 265, 1093. It was stated that the compound 4-(3'-bromoanilino)-6,7-dimethoxyquinazoline was a highly potent inhibitor of EGF receptor tyrosine kinase.

The in vivo inhibitory effect of a 4,5-dianilinophthalimide derivative which is an inhibitor of the EGF family of receptor tyrosine kinases has been demonstrated against the growth in BALB/c nude mice of a human epidermoid carcinoma A-431 or of a human ovarian carcinoma SKOV-3 (Buchdunger et al., *Proc. Nat. Acad. Sci.*, 1994, 91, 2334).

There is no disclosure in these documents of quinazoline derivatives which bear at the 4-position an anilino substituent which is itself substituted at the 4-position by an aryl- or heteroaryl-containing substituent. We have now found that such compounds possess anti-proliferative properties which are believed to arise from their Class I receptor tyrosine kinase inhibitory activity.

According to the present invention there is provided an aniline derivative of the formula I (set out hereinafter) wherein m is 1, 2 or 3 and each $R^1$ is independently halogeno, hydroxy, amino, hydroxyamino, ureido, trifluoromethoxy, (1–4C)alkyl, (1–4C)alkoxy, (2–4C)alkanoyloxy, (2–4C)alkenyloxy, (2–4C)alkynyloxy, (1–3C)alkylenedioxy, (1–4C)alkylamino, di-[(1–4C)alkyl]amino, pyrrolidin-1-yl, piperidino, morpholino, piperazin-1-yl, 4-(1–4C)alkylpiperazin-1-yl, (1–4C)alkylthio, halogeno-(2–4C)alkoxy, hydroxy-(2–4C)alkoxy, (1–4C)alkoxy-(2–4C)alkoxy, amino-(2–4C)alkoxy, (1–4C)alkylamino-(2–4C)alkoxy, di-[(1–4C)alkyl]amino-(2–4C)alkoxy, pyrrolidin-1-yl-(2–4C)alkoxy, piperidino-(2–4C)alkoxy, morpholino-(2–4C)alkoxy, piperazin-1-yl-(2–4C)alkoxy, 4-(1–4C)alkylpiperazin-1-yl-(2–4C)alkoxy, hydroxy-(2–4C)alkylamino-(2–4C)alkoxy, di-[hydroxy-(2–4C)alkyl]amino-(2–4C)alkoxy, (1–4C)alkoxy-(2–4C)alkylamino-(2–4C)alkoxy, di-[(1–4C)alkoxy-(2–4C)-alkyl]amino-(2–4C)alkoxy, amino-(2–4C)alkylamino-(2–4C)alkoxy, di-[amino-(2–4C)alkyl]amino-(2–4C)alkoxy, (1–4C)alkylamino-(2–4C)alkylamino-(2–4C)alkoxy, di-[(1–4C)alkylamino-(2–4C)alkyl]amino-(2–4C)alkoxy, di-{di-[(1–4C)alkyl]amino-(2–4C)alkyl}amino-(2–4C)alkoxy, pyrrolidin-1-yl-(2–4C)alklamino-(2–4C)alkoxy, piperidino-(2–4C)alkylamino-(2–4C)alkoxy, morpholino-(2–4C)alkylamino-(2–4C)alkoxy, piperazin-1-yl-(2–4C)alkylamino-(2–4C)alkoxy, 4-(1–4C)alkylpiperazin-1-yl-(2–4C)alkylamino-(2–4C)alkoxy, (1–4C)alkylthio-(2–4C)alkoxy, (1–4C)alkylsulphinyl-(2–4C)alkoxy, (1–4C)alkylsulphonyl-(2–4C)alkoxy, halogeno-(2–4C)alkylamino, hydroxy-(2–4C)alkylamino, (1–4C)alkoxy-(2–4C)alkylamino, amino-(2–4C)alkylamino, (1–4C)alkylamino-(2–4C)alkylamino, di-[(1–4C)alkyl]amino-(2–4C)alkylamino, pyrrolidin-1-yl-(2–4C)alkylamino, piperidino-(2–4C)alkylamino, morpholino-(2–4C)alkylamino, piperazin-1-yl-(2–4C)alkylamino, 4-(1–4C)alkylpiperazin-1-yl-(2–4C)alkylamino, hydroxy-(2–4C)alkylamino-(2–4C)alkylamino, di-[hydroxy-(2–4C)alkyl]amino-(2–4C)alkylamino, (1–4C)alkoxy-(2–4C)alkylamino-(2–4C)alkylamino, di-[(1–4C)alkoxy-(2–4C)alkyl]amino-(2–4C)alkylamino, amino-(2–4C)alkylamino-(2–4C)alkylamino, di-[amino-(2–4C)alkyl]amino-(2–4C)alkylamino, (1–4C)alkylamino-(2–4C)alkylamino-(2–4C)alkylamino, di-[(1–4C)alkylamino-(2–4C)alkyl]amino-(2–4C)alkylamino, di-{di-[(1–4C)alkyl]amino-(2–4C)alkyl}amino-(2–4C)alkylamino, pyrrolidin-1-yl-(2–4C)alkylamino, piperidino-(2–4C)alkylamino, morpholino-(2–4C)alkylamino, piperazin-1-yl-(2–4C)alkylamino, 4-(1–4C)alkylpiperazin-1-yl-(2–4C)alkylamino-(2–4C)alkylamino, N-(1–4C)alkyl-halogeno-(2–4C)alkylamino, N-(1–4C)alkyl-hydroxy-(2–4C)alkylamino, N-(1–4C)alkyl-(1–4C)alkoxy-(2–4C)alkylamino, di-[halogeno-(2–4C)alkyl]amino, di-[hydroxy-(2–4C)alkyl]amino, di-[(1–4C)alkoxy-(2–4C)alkyl]amino, (2–4C)alkanoylamino, 2-oxopyrrolidin-1-yl, 2-oxopiperidin-1-yl, halogeno-(2–4C)alkanoylamino, hydroxy-(2–4C)alkanoylamino, (1–4C)alkoxy-(2–4C)alkanoylamino, (3–4C)alkenoylamino, (3–4C)alkynoylamino, (2–4C)alkanoyloxy-(2–4C)alkanoylamino, amino-(2–4C)alkanoylamino, (1–4C)alkylamino-(2–4C)alkanoylamino, di-[(1–4C)alkyl]amino-(2–4C)alkanoylamino, pyrrolidin-1-yl-(2–4C)alkanoylamino, piperidino-(2–4C)alkanoylamino, morpholino-(2–4C)alkanoylamino, piperazin-1-yl-(2–4C)alkanoylamino, 4-(1–4C)alkylpiperazin-1-yl-(2–4C)alkanoylamino, (1–4C)alkylthio-(2–4C)alkanoylamino, (1–4C)alkylsulphinyl-(2–4C)alkanoylamino, (1–4C)alkylsulphonyl-(2–4C)alkanoylamino, N-(1–4C)alkyl-(2–4C)alkanoylamino, N-(1–4C)alkyl-halogeno-(2–4C)alkanoylamino, N-(1–4C)alkyl-hydroxy-(2–4C)alkanoylamino, N-(1–4C)alkyl-(1–4C)alkoxy-(2–4C)alkanoylamino, N-(1–4C)alkyl-(3–4C)alkenoylamino or N-(1–4C)alkyl-(3–4C)alkynoylamino, and wherein any of the above-mentioned $R^1$ substituents comprising a $CH_2$ (methylene) group which is not attached to a halogeno, SO or $SO_2$ group or to a N, O or S atom optionally bears on said $CH_2$ group a substituent selected from hydroxy, amino, (1–4C)alkoxy, (1–4C)alkylamino and di-[(1–4C)alkyl]amino;

n is 0, 1, 2 or 3 and each $R^2$ is independently halogeno, trifluoromethyl, hydroxy, amino, nitro, cyano, (1–4C)alkyl, (1–4C)alkoxy, (1–4C)alkylamino, di-[(1–4C)alkyl]amino or (2–4C)alkanoylamino;

X is a group of the formula CO, $C(R^3)_2$, $CH(OR^3)$, $C(R^3)_2$—$C(R^3)_2$, $C(R^3)$=$C(R^3)$, C≡C, CH(CN), O, S, SO, $SO_2$, $CONR^3$, $SO_2NR^3$, $NR^3CO$, $NR^3SO_2$, $OC(R^3)_2$, $SC(R^3)_2$, $C(R^3)_2O$ or $C(R^3)_2S$ wherein each $R^3$ is independently hydrogen or (1–4C)alkyl; and Q is a phenyl or naphthyl group or a 5- or 6-membered heteroaryl moiety containing 1, 2 or 3 heteroatoms selected from oxygen, nitrogen and sulphur, which heteroaryl moiety is a single ring or is fused to a benzo ring, and wherein said phenyl or naphthyl group or heteroaryl moiety is optionally substituted with 1, 2 or 3 substituents selected from halogeno, trifluoromethyl, cyano, carbamoyl, hydroxy, amino, nitro, (1–4C)alkyl, (1–4C)alkoxy, (1–4C)alkylamino, di-[(1–4C)alkyl]amino, (2–4C)alkanoylamino, N-(1–4C)alkylcarbamoyl and N,N-di-[(1–4C)alkyl]carbamoyl;

or a pharmaceutically-acceptable salt thereof.

According to a further aspect of the present invention there is provided an aniline derivative of the formula I wherein m is 1, 2 or 3 and each $R^1$ is independently halogeno, hydroxy, amino, hydroxyamino, ureido, trifluoromethoxy, (1–4C)alkyl, (1–4C)alkoxy, (1–3C)alkylenedioxy, (1–4C)alkylamino, di-[(1–4C)alkyl]amino, pyrrolidin-1-yl, piperidino, morpholino, piperazin-1-yl, 4-(1–4C)alkylpiperazin-1-yl, (1–4C)alkylthio, halogeno-(2–4C)alkoxy, hydroxy-(2–4C)alkoxy, (1–4C)alkoxy-(2–4C)alkoxy, amino-(2–4C)alkoxy, (1–4C)alkylamino-(2–4C)alkoxy, di-[(1–4C)alkyl]amino-(2–4C)alkoxy, pyrrolidin-1-yl-(2–4C)alkoxy, piperidino-(2–4C)alkoxy, morpholino-(2–4C)alkoxy, piperazin-1-yl-(2–4C)alkoxy, 4-(1–4C)alkylpiperazin-1-yl-(2–4C)alkoxy, halogeno-(2–4C)alkylamino, hydroxy-(2–4C)alkylamino, (1–4C) alkoxy-(2–4C)alkylamino, amino-(2–4C)alkylamino, (1–4C)alkylamino-(2–4C)alkylamino, di-[(1–4C)alkyl] amino-(2–4C)alkylamino, pyrrolidin-1-yl-(2–4C) alkylamino, piperidino-(2–4C)alkylamino, morpholino-(2–4C)alkylamino, piperazin-1-yl-(2–4C)alkylamino, 4-(1–4C)alkylpiperazin-1-yl-(2–4C)alkylamino, (2–4C) alkanoylamino, 2-oxopyrrolidin-1-yl, 2-oxopiperidin-1-yl, halogeno-(2–4C)alkanoylamino, hydroxy-(2–4C) alkanoylamino, (1–4C)alkoxy-(2–4C)alkanoylamino, (3–4C)alkenoylamino, (3–4C)alkynoylamino, N-(1–4C) alkyl-(2–4C)alkanoylamino, N-(1–4C)alkyl-halogeno-(2–4C)alkanoylamino, N-(1–4C)alkyl-hydroxy-(2–4C) alkanoylamino, N-(1–4C)alkyl-(1–4C)alkoxy-(2–4C) alkanoylamino, N-(1–4C)alkyl-(3–4C)alkenoylamino or N-(1–4C)alkyl-(3–4C)alkynoylamino;

n is 0, 1, or 2 and each $R^2$ is independently halogeno, trifluoromethyl, hydroxy, amino, nitro, cyano, (1–4C) alkyl, (1–4C)alkoxy, (1–4C)alkylamino, di-[(1–4C) alkyl]amino or (2–4C)alkanoylamino;

X is a group of the formula CO, $C(R^3)_2$, $CH(OR^3)$, CH(CN), O, S, SO, $SO_2$, $CONR^3$, $SO_2NR^3$, $NR^3CO$, $NR^3SO_2$, $OC(R^3)_2$, $SC(R^3)_2$, $C(R^3)_2O$ or $C(R^3)_2S$ wherein each $R^3$ is independently hydrogen or (1–4C) alkyl; and Q is a phenyl or naphthyl group or a 5- or 6-membered heteroaryl moiety containing 1, 2 or 3 heteroatoms selected from oxygen, nitrogen and sulphur, which heteroaryl moiety is a single ring or is fused to a benzo ring, and wherein said phenyl or naphthyl group or heteroaryl moiety is optionally substituted with 1, 2 or 3 substituents selected from halogeno, trifluoromethyl, cyano, carbamoyl, hydroxy, amino, nitro, (1–4C)alkyl, (1–4C)alkoxy, (1–4C) alkylamino, di-[(1–4C)alkyl]amino, (2–4C) alkanoylamino, N-(1–4C)alkylcarbamoyl and N,N-di-[(1–4C)alkyl]carbamoyl;

or a pharmaceutically-acceptable salt thereof.

The chemical formulae referred to herein by Roman numerals are set out for convenience on a separate sheet hereinafter. In this specification the term "alkyl" includes both straight and branched chain alkyl groups but references to individual alkyl groups such as "propyl" are specific for the straight chain version only. For example when $R^1$ is a hydroxy-(2–4C)alkoxy group, suitable values for this generic radical include 2-hydroxyethoxy, 2-hydroxypropoxy, 1-hydroxyprop-2-yloxy and 3-hydroxypropoxy. An analogous convention applies to other generic terms.

Within the present invention it is to be understood that an aniline derivative of the formula I may exhibit the phenomenon of tautomerism and that the formulae drawings within this specification can represent only one of the possible tautomeric forms. It is to be understood that the invention encompasses any tautomeric form which possesses anti-proliferative activity and is not to be limited merely to any one tautomeric form utilised within the formulae drawings.

The quinazolines of the formula I are unsubstituted at the 2-position thus it is to be understood that the $R^1$ groups are located only on the benzo portion of the quinazoline ring.

It is also to be understood that certain aniline derivatives of the formula I can exist in solvated as well as unsolvated forms such as, for example, hydrated forms. It is to be understood that the invention encompasses all such solvated forms which possess anti-proliferative activity.

Suitable values for the generic radicals referred to above include those set out below.

A suitable value for $R^1$, a substituent on a $CH_2$ group within $R^1$, for $R^2$ or a substituent on Q when it is halogeno is, for example fluoro, chloro, bromo or iodo;

when it is (1–4C)alkyl is, for example, methyl, ethyl, propyl, isopropyl or butyl;

when it is (1–4C)alkoxy is, for example, methoxy, ethoxy, propoxy, isopropoxy or butoxy;

when it is (1–4C)alkylamino is, for example, methylamino, ethylamino or propylamino;

when it is di-[(1–4C)alkyl]amino is, for example, dimethylamino, diethylamino, N-ethyl-N-methylamino or dipropylamino;

and when it is (2–4C)alkanoylamino is, for example, acetamido, propionamido or butyramido.

Suitable values for each $R^1$ substituent which may be present on the quinazoline ring include, for example:

| | |
|---|---|
| for (2-4C)alkanoyloxy: | acetoxy and propionyloxy; |
| for (2-4C)alkenyloxy: | vinyloxy and allyloxy; |
| for (2-4C)alkynyloxy: | 2-propynyloxy; |
| for (1-4C)alkylthio: | methylthio, ethylthio and propylthio; |
| for (1-3C)alkylenedioxy: | methylenedioxy, ethylenedioxy and propylenedioxy; |
| for 4-(1-4C)alkyl piperazin-1-yl: | 4-methylpiperazin-1-yl and 4-ethylpiperazin-1-yl; |
| for halogeno-(2-4C)alkoxy: | 2-fluoroethoxy, 2-chloroethoxy, 2-bromoethoxy, 3-fluoropropoxy, 3-chloropropoxy, 2,2,2-trifluoroethoxy, 1,1,2,2,2-pentafluoroethoxy, 2,2,3,3-tetrafluoropropoxy, 2,2,3,3,3-pentafluoropropoxy and 1,1,2,2,3,3,3-heptafluoropropoxy; |
| for hydroxy- (2-4C)alkoxy: | 2-hydroxyethoxy, 3-hydroxypropoxy and 4-hydroxybutoxy; |
| for (1-4C)alkoxy- (2-4C)alkoxy: | 2-methoxyethoxy, 2-ethoxyethoxy, 3-methoxypropoxy and 3-ethoxypropoxy; |
| for amino-(2-4C)alkoxy: | 2-aminoethoxy and 3-aminopropoxy; |
| for (1-4C)alkylamino-(2-4C)-alkoxy: | 2-methylaminoethoxy, 2-ethyl aminoethoxy, 2-propylaminoethoxy, 3-methylaminopropoxy and |

| | |
|---|---|
| for di-[(1-4C)alkyl]amino-(2-4C)alkoxy: | 3-ethylaminopropoxy; 2-dimethylaminoethoxy, 2-(N-ethyl-N-methylamino)ethoxy, 2-diethylaminoethoxy, 2-dipropylaminoethoxy, 3-dimethylaminopropoxy and 3-diethylaminopropoxy; |
| for pyrrolidin-1-yl-(2-4C)alkoxy: | 2-(pyrrolidin-1-yl)ethoxy and 3-(pyrrolidin-1-yl)propoxy; |
| for piperidino-(2-4C)alkoxy: | 2-piperidinoethoxy and 3-piperidinopropoxy; |
| for morpholino-(2-4C)alkoxy: | 2-morpholinoethoxy and 3-morpholinopropoxy; |
| for piperazin-1-yl-(2-4C)alkoxy: | 2-(piperazin-1-yl)ethoxy and 3-(piperazin-1-yl)propoxy; |
| for 4-(1-4C)alkylpiperazin-1-yl (2-4C)alkoxy: | 2-(4-methylpiperazin-1-yl)ethoxy and 3-(4-methylpiperazin-1-yl)propoxy; |
| for hydroxy-(2-4C)alkylamino-(2-4C)alkoxy: | 2-(2-hydroxyethylamino)ethoxy, 3-(2-hydroxyethylamino)propoxy and 2-(3-hydroxypropylamino)ethoxy; |
| for di-[hydroxy-(2-4C)alkyl]-amino-(2-4C)alkoxy: | 2-[di-(2-hydroxyethyl)amino]ethoxy, 3-[di-(2-hydroxyethyl)amino]propoxy and 2-[di-(3-hydroxypropyl)amino]ethoxy; |
| for (1-4C)alkoxy-(2-4C)-alkylamino-(2-4C)alkoxy: | 2-(2-methoxyethylamino)ethoxy, 3-(2-methoxyethylamino)propoxy and 2-(3-methoxypropylamino)ethoxy; |
| for di-[(1-4C)alkoxy-(2-4C)-alkyl]amino-(2-4C)alkoxy: | 2-[di-(2-methoxyethyl)amino]ethoxy, 3-[di-(2-methoxyethyl)amino]propoxy and 2-[di-(3-methoxypropyl)amino]ethoxy; |
| for amino-(2-4C)alkylamino-(2-4C)alkoxy: | 2-(2-aminoethylamino)ethoxy, 3-(2-aminoethylamino)propoxy and 2-(3-aminopropylamino)ethoxy; |
| for di-[amino-(2-4C)alkyl]-amino-(2-4C)alkoxy: | 2-[di-(2-aminoethyl)amino]ethoxy, 3-[di-(2-aminoethyl)amino]propoxy and 2-di-(3-aminopropyl)amino]-ethoxy; |
| for (1-4C)alkylamino-(2-4C)-alkylamino-(2-4C)alkoxy: | 2-(2-methylaminoethylamino)ethoxy, 3-(2-methylaminoethylamino)propoxy and 2-(3-methylaminopropylamino)-ethoxy; |
| for di-[(1-4C)alkylamino-(2-4C)-alkyl]amino-(2-4C)alkoxy: | 2-[di-(2-methylaminoethyl)amino]-ethoxy, 3-[di-(2-methylaminoethyl) amino]propoxy and 2-[di-(3-methylaminopropyl)amino]-ethoxy; |
| for di-[(1-4C)alkyl]amino; (2-4C)alkylamino-(2-4C)alkoxy-: | 2-(2-dimethylaminoethylamino)ethoxy, 3-(2-dimethylaminoethylamino)propoxy and 2-(3-dimethylaminopropylamino)-ethoxy; |
| for di-{di-[(1-4C)alkyl]amino-(2-4C)alkyl]amino-(2-4C)alkoxy: | 2-[di-(2-dimethylaminoethyl)amino]-ethoxy, 3-[di-(2-dimethylaminoethyl)amino]-propoxy and 2-[di-(3-dimethylaminopropyl)amino]-ethoxy; |
| for pyrrolidin-1-yl-(2-4C) alkylamino-(2-4C)alkoxy: | 2-(2-pyrrolidin-1-ylethylamino)-ethoxy, 3-(2-pyrrolidin-1-ylethylamino)-propoxy and 2-(3-pyrrolidin-1-ylpropylamino)-ethoxy; |
| for piperidino-(2-4C)-alkylamino-(2-4C)alkoxy: | 2-(2-piperidinoethylamino)ethoxy, 3-(2-piperidinoethylamino)propoxy and 2-(3-piperidinopropylamino)-ethoxy; |
| for morpholino-(2-4C)alkylamino-(2-4C)alkoxy: | 2-(2-morpholinoethylamino)ethoxy, 3-(2-morpholinoethylamino)propoxy and 2-(3-morpholinopropylamino)-ethoxy; |
| for piperazin-1-yl-(2-4C)-alkylamino-(2-4C)alkoxy: | 2-(2-piperazin-1-ylethylamino)-ethoxy, 3-(2-piperazin-1-ylethylamino) propoxy and 2-(3-piperazin-1-ylpropylamino)-ethoxy; |
| for 4-(1-4C)alkylpiperazin-1-yl-(2-4C)alkylamino-(2-4C)alkoxy: | 2-(2-(4-methylpiperazin-1-ylethyl) amino) ethoxy, |

| | |
|---|---|
| | 3-(2-(4-methylpiperazin-1-ylethyl) amino]propoxy and 2-[3-( 4-methylpiperazin-1-ylpropyl)- amino]ethoxy; |
| for (1-4C)alkylthio-(2-4C)alkoxy: | 2-methylthioethoxy and 3-methylthiopropoxy; |
| for (1-4C)alkylsulphinyl-(2-4C)- alkoxy: | 2-methylsulphinylethoxy and 3-methylsulphinylpropoxy; |
| for (1-4C)alkylsulphonyl-(2-4C)- alkoxy: | 2-methylsulphonylethoxy and 3-methylsulphonylpropoxy; |
| for halogen-(2-4C)alkylamino: | 2-fluoroethylamino, 2-chloroethylamino, 2-bromoethylamino, 3-fluoropropylamino and 3-chloropropylamino; |
| for hydroxy-(2-4C)alkylamino: | 2-hydroxyethylamino, 3-hydroxypropylamino and 4-hydroxybutylamino; |
| for (1-4C)alkoxy-(2-4C)alkyl- amino: | 2-methoxyethylamino, 2-ethoxyethylamino, 3-methoxypropylamino and 3-ethoxypropylamino; |
| for amino-(2-4C)alkylamino: | 2-aminoethylamino, 3-aminopropyl- amino and 4-aminobutylamino; |
| for (1-4C)alkylamino- (2-4C)alkylamino: | 2-methylaminoethylamino, 2-ethyl- aminoethylamino, 2-propylamino- ethylamino, 3-methylaminopropyl amino, 3-ethylaminopropylamino and 4-methylaminobutylamino; |
| for di-[(1-4C)alkyl]amino- (2-4C)alkylamino: | 2-dimethylaminoethylamino, 2-(N-ethyl-N-methylamino)ethylamino, 2-diethylaminoethylamino, 2-dipropylaminoethylamino, 3-dimethylaminopropylamino, 3-diethylaminopropylamino and 4-dimethylaminobutylamino; |
| for pyrrolidin-1-yl-(2-4C)- alkylamino: | 2-(pyrrolidin-1-yl)ethylamino and 3-(pyrrolidin-1-yl) propylamino; |
| for piperidino-(2-4C)alkylamino: | 2-piperidinoethylamino and 3-piperidinopropylamino; |
| for morpholino-(2-4C)alkylamino: | 2-morpholinoethylamino and 3-morpholinopropylamino; |
| for piperazin-1-yl-(2-4C)- alkylamino: | 2-(piperazin-1-yl)ethylamino and 3-(piperazin-1-yl)propylamino; |
| for 4-(1-4C)alkylpiperazin-1-yl- (2-4C)alkylamino: | 2-(4-methylpiperazin-1-yl)ethylamino and 3-(4-methylpiperazin-1-yl)- propylamino; |
| for hydroxy-(2-4C)alkylamino- (2-4C)alkylamino; | 2-(2-hydroxyethylamino)ethylamino, 3-(2-hydroxyethylamino)propylamino and 2-(3-hydroxypropylamino)- ethylamino; |
| for di-[hydroxy-(2-4C)alkyl]- amino-(2-4C)alkylamino: | 2-[di-(2-hydroxyethyl)amino]- ethylamino, 3-[di-(2-hydroxyethyl)- amino]propylamino and 2-[di-(3-hydroxypropyl)amino] ethylamino; |
| for (1-4C)alkoxy-(2-4C)- alkylamino-(2-4C)alkylamino: | 2-(2-methoxyethylamino) ethylamino, 3-(2-methoxyethylamino) propylamino and 2-(3-methoxypropylamino)- ethylamino; |
| for di-[(1-4C)alkoxy-(2-4C)- alkyl]amino-(2-4C)alkylamino: | 2-[di-(2-methoxyethyl)amino]- ethylamino, 3-[di-(2-methoxyethyl)amino]- propylamino and 2-[di-(3-methoxypropyl)amino]- ethylamino; |
| for amino-(2-4C)alkylamino- (2-4C)alkylamino: | 2-(2-aminoethylamino)ethylamino, 3-(2-aminoethylamino) propylamino and 2-(3-aminopropylamino) ethylamino; |
| for di-[amino-(2-4C)alkyl]amino- (2-4C)alkylamino: | 2-[di-(2-aminoethyl)amino]- ethylamino, 3-[di-(2-aminoethyl)- amino]propylamino and 2-[di-(3-aminopropyl)amino]- ethylamino; |
| for (1-4C)alkylamino-(2-4C)- alkylamino-(2-4C)alkylamino: | 2-(2-methylaminoethylamino)- ethylamino, 3-(2-methylaminoethylamino)- propylamino and 2-(3-methylamino- propylamino)ethylamino; |
| for di-[(1-4C)alkylamino-(2-4C) | 2-[di-(2-methylaminoethyl)amino]- |

| | |
|---|---|
| alkyl]amino-(2-4C)alkylamino | ethylamino, 3-[di-(2-methylamino-ethyl)amino]propylamino and 2-[di-(3-methylaminopropyl)amino]-ethylamino; |
| for di-[(1-4C)alkyl]amino-(2-4C)-alkylamino-(2-4C)alkylamino: | 2-(2-dimethylaminoethylamino)-ethylamino, 3-(2-dimethylamino-ethylamino) propylamino and 2-(3-dimethylaminopropylamino)-ethylamino; |
| for di-(di-[(1-4C)alkylamino (2-4C)alkylamino-(2-4C)-alkylamino: | 2-[di-(2-dimethylaminoethyl)amino)-ethylamino, 3-[di-(2-dimethylamino-ethyl)amino]propylamino and 2-[di-(3-dimethylaminopropyl)amino)-ethylamino; |
| for pyrrolidin-1-yl-(2-4C)-alkylamino-(2-4C)alkylamino: | 2-(2-pyrrolidin-1-ylethylamino)-ethylamino, 3-(2-pyrrolidin-1-ylethylamino) propylamino and 2-(3-pyrrolidin-1-ylpropylamino)-ethylamino; |
| for piperidino-(2-4C)alkylamino-(2-4C)alkylamino: | 2-(2-piperidinoethylamino)-ethylamino, 3-(2-piperidinoethylamino)-propylamino and 2-(3-piperidinopropylamino)-ethylamino; |
| for morpholino-(2-4C)alkylamino-(2-4C)alkylamino: | 2-(2-morpholinoethylamino)-ethylamino, 3-(2-morpholinoethylamino-propylamino and 2-(3-morpholino-propylamino)ethylamino; |
| for piperazin-1-yl-(2-4C)-alkylamino-(2-4C)alkylamino: | 2-(2-piperazin-1-ylethylamino)-ethylamino, 3-(2-piperazin-1 ylethylamino) propylamino and 2-(3-piperazin-1-ylpropylamino) ethylamino; |
| for 4-(1-4C)alkylpiperazin-1-yl-(2-4C)alkylamino-(2-4C)-alkylamino: | 2-[2-(4-methylpiperazin-1-ylethyl)-amino]ethylamino, 3-[2-(4-methyl-piperazin-1-ylethyl)amino]-propylamino and 2-[3-(4-methylpiperazin-1-ylpropyl)-amino]ethylamino; |
| for N-(1-4C)alkyl-halogeno-(2-4C)alkylamino: | N-(2-chloroethyl)-methylamino, N-(2-bromoethyl)-N-methylamino and N-(2-bromoethyl)-N-ethylamino; |
| for N-(1-4C)alkyl-hydroxy-(2-4C)-alkylamino: | N-(2-hydroxyethyl)-N-methylamino, N-(3-hydroxypropyl)-N-methylamino and N-ethyl-N-(2-hydroxyethyl)amino; |
| for N-(1-4C)alkyl-(1-4C)alkoxy (2-4C)alkylamino: | N-methyl-N-(2-methoxyethyl)amino, N-methyl-N-(3-methoxypropyl)amino and N-ethyl-N-(2-methoxyethyl)amino; |
| for di-[halogeno-(2-4C)alkyl]-amino: | di-(2-chloroethyl)amino and di-(3-chloropropyl)amino; |
| for di-[hydroxy-(2-4C)alkyl]-amino: | di-(2-hydroxyethyl)amino and di-(3-hydroxypropyl)amino; |
| for di-[(1-4C)alkoxy-(2-4C)-alkyl]amino: | di-(2-methoxyethyl)amino, di-(2-ethoxyethyl)amino and di-(3-methoxypropyl)amino; |
| for halogeno-(2-4C)alkanoylamino: | 2-chloroacetamido, 2-bromoacetamido, 3-chloropropylamido and 3-bromo-propionamido; |
| for hydroxy-(2-4C)alkanoylamino: | 2-hydroxyacetamido, 3-hydroxy-propionamido and 4-hydroxybutyramido; |
| for (1-4C)alkoxy-(2-4C)-alkanoylamino: | 2-methoxyacetamido, 2-ethoxy-acetamido, 2-propoxyacetamido, 3-methoxypropionamido, 3-ethoxypropionamido and 4-methoxybutyramido; |
| for (3-4C)alkenoylamino: | acrylamido, methacrylamido, crotonamido and isocrotonamido; |
| for (3-4C)alkynoylamino: | propiolamido; |
| for (2-4C)alkanoyloxy-(2-4C)-alkanoylamino: | 2-acetoxyacetamido, 2-acetoxypropionamido, 3-acetoxypropionamido and 2-propionyloxyacetamido; |
| for amino-(2-4C)alkanoylamino: | 2-aminoacetamido, 2-aminopropionamido and 3-aminopropionamido; |
| for (1-4C)alkylamino-(2-4C)-alkanoylamino: | 2-methylaminoacetamido, 2-ethylaminoacetamido, |

| | -continued |
|---|---|
| | 2-methylaminopropionamido and |
| | 3-methylaminopropionamido; |
| for di-[(1-4C)alkyl]amino-(2-4C) alkanoylamino: | 2-dimethylaminoacetamido, 2-diethylaminoacetamido, 2-dimethylaminopropionamido and 3-dimethylaminopropionamido; |
| for pyrrolidin-1-yl-(2-4C) alkanoylamino: | 2-pyrrolidin-1-ylacetamido, 2-pyrrolidin-1-ylpropionamido and 3-pyrrolidin-1-ylpropionamido; |
| for piperidino-(2-4C)-alkanoylamino: | 2-piperidinoacetamido, 2-piperidinopropionamido and 3-piperidinopropionamido; |
| for morpholino-(2-4C)-alkanoylamino: | 2-morpholinoacetamido, 2-morpholinopropionamido and 3-morpholinopropionamido; |
| for piperazin-1-yl-(2-4C)-alkanoylamino: | 2-piperazin-1-ylacetamido, 2-piperazin-1-ylpropionamido and 3-piperazin-1-ylpropionamido; |
| for 4-(1-4C)alkylpiperazin-1-yl-(2-4C)alkanoylamino: | 2-(4-methylpiperazin-1-yl)acetamido, 2-(4-methylpiperazin-1-yl)-propionamido and 3-(4-methyl piperazin-1-yl)propionamido; |
| tor (1-4C)alkylthio-(2-4C)-alkanoylamino: | 2-methylthioacetamido, 2-ethylthioacetamido, 2-methylthiopropionamido and 3-methylthiopropionamido; |
| for (1-4C)alkylsulphinyl-(2-4C)-alkanoylamino: | 2-methylsulphinylacetamido and 3-methylsulphinylpropionamido; |
| for (1-4C)alkylsulphonyl-(2-4C)-alkanoylamino: | 2-methylsulphonylacetamido and 3-methylsulphonylpropionamido |
| for $\underline{N}$-(1-4C)alkyl-(2-4C)-alkanoylamino: | $\underline{N}$-methylacetamido, $\underline{N}$-ethylacetamido and $\underline{N}$-methylpropionamido; |
| for $\underline{N}$-(1-4C)alkylbenzamido: | $\underline{N}$-methylbenzamido; |
| for $\underline{N}$-(1-4C)alkyl-halogeno-(2-4C)alkanoylamino: | 2-chloro-$\underline{N}$-methylacetamido, 2-chloro-$\underline{N}$-ethylacetamido and 3-chloro-$\underline{N}$-methylpropionamido; |
| for $\underline{N}$-(1-4C)alkyl-hydroxy-(2-4C)alkanoylamino: | 2-hydroxy-$\underline{N}$-methylacetamido, $\underline{N}$-ethyl-2-hydroxyacetamido and 3-hydroxy-$\underline{N}$-methylacetamido; |
| for $\underline{N}$-(1-4C)alkyl-(1-4C)alkoxy (2-4C)alkanoylamino: | 2-methoxy-$\underline{N}$-methylacetamido, $\underline{N}$-ethyl-2-methoxyatetamido, 2-ethoxy-$\underline{N}$-methylacetamido and 2-ethoxy-$\underline{N}$-ethylacetamido; |
| for $\underline{N}$-(1-4C)alkyl-(3-4C) alkenoylamino: | $\underline{N}$-methylacrylamido, $\underline{N}$-ethylacrylamido and $\underline{N}$-methylmethacrylamido; |
| for $\underline{N}$-(1-4C)alkyl-(3-4C) alkynoylamino: | $\underline{N}$-methylpropiolamido and $\underline{N}$-ethylpropiolamido |

When the group $(R^1)_m$ represents a (1–3C)alkylenedioxy moiety, the oxygen atoms thereof occupy adjacent positions on the quinazoline ring, especially the 6- and 7-positions.

When m is 1 the $R^1$ substituent is preferably located at the 6- or 7-position of the quinazoline ring and when m is 2 the $R^1$ substituents are preferably located at the 6- and 7-positions of the quinazoline ring.

Suitable substituents formed when any of the $R^1$ substituents comprising a $CH_2$ group which is not attached to a halogeno, SO or $SO_2$ group or to a N, O or S atom bears on said $CH_2$ group a substituent selected from hydroxy, amino, (1–4C)alkoxy, (1–4C)alkylamino and di-[(1–4C)alkyl] amino include, for example, substituted (1–4C)alkylamino-(2–4C)alkoxy or di-[(1–4C)alkyl]amino-(2–4C)alkoxy groups, for example hydroxy-(1–4C)alkylamino-(2–4C) alkoxy or hydroxy-di-[(1–4C)alkyl]amino-(2–4C)alkoxy groups such as 3-methylamino-2-hydroxypropoxy and 3-dimethylamino-2-hydroxypropoxy.

A suitable value for the $R^3$ group which may be present within X when said $R^3$ group is (1–4C)alkyl is, for example, methyl, ethyl or propyl.

A suitable value for Q when it is a naphthyl group is, for example, 1-naphthyl or 2-naphthyl.

A suitable value for Q when it is a 5- or 6-membered heteroaryl moiety containing 1, 2 or 3 heteroatoms selected from oxygen, nitrogen and sulphur, which is a single ring is, for example, furyl, pyrrolyl, thienyl, pyridyl, oxazolyl, isoxazolyl, pyrazolyl, imidazolyl, thiazolyl, isothiazolyl, pyrazinyl, pyrimidinyl, pyridazinyl, 1,2,3-triazolyl, 1,2,4-triazolyl, oxadiazolyl, furazanyl or thiadiazoylyl, or which is fused to a benzo ring is, for example, benzofuryl, indolyl, benzothienyl, quinolyl, isoquinolyl, benzoxazolyl, indazolyl, benzimidazolyl, benzothiazolyl, cinnolinyl, quinazolinyl, quinoxalinyl or benzotriazolyl. Said heteroaryl moiety may be attached to X through any available position. The optional substituents on Q may be located at any available position including on any available nitrogen heteroatom.

A suitable value for a N-(1–4C)alkylcarbamoyl substituent which may be present on Q is, for example, N-methylcarbamoyl and N-ethylcarbamoyl; and for a N,N-di-[(1–4C)alkyl]carbamoyl substituent which may be present on Q is, for example, N,N-dimethylcarbamoyl and N,N-diethylcarbamoyl.

A suitable pharmaceutically-acceptable salt of an aniline derivative of the invention is, for example, an acid-addition salt of an aniline derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of an aniline derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention include, for example, aniline derivatives of the formula I, or pharmaceutically-acceptable salts thereof, wherein:

(a) m is 1 or 2 and each $R^1$ is hydroxy, amino, hydroxyamino, trifluoromethoxy, (1–4C)alkoxy, (1–4C)alkylamino, di-[(1–4C)alkyl]amino, pyrrolidin-1-yl, piperidino, morpholino, piperazin-1-yl, 4-(1–4C)alkylpiperazin-1-yl, (1–4C)alkylthio, halogeno-(2–4C)alkoxy, hydroxy-(2–4C)alkoxy, (1–4C)alkoxy-(2–4C)alkoxy, hydroxy-(2–4C)alkylamino, (1–4C)alkoxy-(2–4C)alkylamino, (2–4C)alkanoylamino, 2-oxopyrrolidin-1-yl, halogeno-(2–4C)alkanoylamino, hydroxy-(2–4C)alkanoylamino or (1–4C)alkoxy-(2–4C)alkanoylamino; and n, $R^2$, X and Q have any of the meanings defined hereinbefore or in this section relating to particular novel compounds of the invention;

(b) m is 1 or 2 and each $R^1$ is independently hydroxy, trifluoromethoxy, (1–4C)alkoxy, (1–3C)alkylenedioxy, halogeno-(2–4C)alkoxy, hydroxy-(2–4C)alkoxy, (1–4C)alkoxy-(2–4C)alkoxy, (1–4C)alkylamino-(2–4C)alkoxy or di-[(1–4C)alkyl]amino-(2–4C)alkoxy; and n, $R^2$, X and Q have any of the meanings defined hereinbefore or in this section relating to particular novel compounds of the invention;

(c) m is 1 or 2 and each $R^1$ is amino, hydroxyamino, (1–4C)alkylamino, di-[(1–4C)alkyl]amino, hydroxy-(2–4C)alkylamino, (1–4C)alkoxy-(2–4C)alkylamino, (2–4C)alkanoylamino, halogeno-(2–4C)alkanoylamino, (1–4C)alkoxy-(2–4C)alkanoylamino, (1–4C)alkylamino-(2–4C)alkanoylamino or di-[(1–4C)alkyl]amino-(2–4C)alkanoylamino; and n, $R^2$, X and Q have any of the meanings defined hereinbefore or in this section relating to particular novel compounds of the invention;

(d) m is 1 or 2 and each $R^1$ is amino, hydroxyamino, (1–4C)alkylamino, di-[(1–4C)alkyl]amino, (2–4C)alkanoylamino, 2-oxopyrrolidin-1-yl, halogeno-(2–4C)alkanoylamino, (3–4C)alkenoylamino, (3–4C)alkynoylamino, N-(1–4C)alkyl-(2–4C)alkanoylamino and N-(1–4C)alkyl-halogeno-(2–4C)alkanoylamino; and n, $R^2$, X and Q have any of the meanings defined hereinbefore or in this section relating to particular novel compounds of the invention;

(e) m is 1 or 2 and each $R^1$ is hydroxy or (1–4C)alkoxy; and n, $R^2$, X and Q have any of the meanings defined hereinbefore or in this section relating to particular novel compounds of the invention;

(f) n is 0 or 1 and $R^2$ is hydroxy, halogeno, trifluoromethyl, amino, nitro, cyano, (1–4C)alkyl or (1–4C)alkoxy; and m, $R^1$, X and Q have any of the meanings defined hereinbefore or in this section relating to particular novel compounds of the invention.

(g) n is 1 and $R^2$ is halogeno, cyano or (1–4C)alkyl; and m, $R^1$, X and Q have any of the meanings defined hereinbefore or in this section relating to particular novel compounds of the invention;

(h) X is a group of the formula CO, $C(R^3)_2$, $CH(OR^3)$, O, S, SO or $SO_2$, wherein each $R^3$ is independently hydrogen or (1–4C)alkyl; and m, $R^1$, n, $R^2$ and Q have any of the meanings defined hereinbefore or in this section relating to particular novel compounds of the invention;

(i) X is a group of the formula $CONR^3$, $SO_2NR^3$, $NR^3CO$ or $NR^3SO_2$; wherein $R^3$ is hydrogen or (1–4C)alkyl; and m, $R^1$ n, $R^2$ and Q have any of the meanings defined hereinbefore or in this section relating to particular novel compounds of the invention;

(j) X is a group of the formula $OC(R^3)_2$, $SC(R^3)_2$, $C(R^3)_2O$ or $C(R^3)_2S$, wherein each $R^3$ is independently hydrogen or (1–4C)alkyl; and m, $R^1$, n, $R^2$ and Q have any of the meanings defined hereinbefore or in this section relating to particular novel compounds of the invention;

(k) X is a group of the formula $OC(R^3)_2$, wherein each $R^3$ is independently hydrogen or (1–4C)alkyl; and m, $R^1$, n, $R^2$ and Q have any of the meanings defined hereinbefore or in this section relating to particular novel compounds of the invention;

(l) Q is a phenyl or naphthyl group which is optionally substituted with 1, 2 or 3 substituents selected from halogeno, trifluoromethyl, cyano, carbamoyl, hydroxy, (1–4C)alkyl and (1–4C)alkoxy; and m, $R^1$, n, $R^2$ and X have any of the meanings defined hereinbefore or in this section relating to particular novel compounds of the invention;

(m) Q is a 5- or 6-membered heteroaryl moiety containing 1, 2 or 3 heteroatoms selected from oxygen, nitrogen and sulphur, and wherein said heteroaryl moiety is optionally substituted with 1 or 2 substituents selected from halogeno and (1–4C)alkyl; and m, $R^1$, n, $R^2$ and X have any of the meanings defined hereinbefore or in this section relating to particular novel compounds of the invention; or (n) Q is a 5- or 6-membered heteroaryl moiety selected from furyl, pyrrolyl, thienyl, pyridyl, oxazolyl, imidazolyl, thiazolyl, pyrimidinyl, 1,2,4-triazolyl, oxadiazolyl and thiadiazolyl, and wherein said heteroaryl moiety is optionally substituted with 1 or 2 (1–4C)alkyl substituents; and m, $R^1$, n, $R^2$ and X have any of the meanings defined hereinbefore or in this section relating to particular novel compounds of the invention.

A preferred compound of the invention is an aniline derivative of the formula I wherein m is 1 with the substituent located at the 6-position or m is 2 with the substituents located at the 6- and 7-positions and each $R^1$ is fluoro, chloro, bromo, hydroxy, amino, methoxy, ethoxy, acetoxy, methylamino, ethylamino, 2-bromoethoxy, 2,2,2-trifluoroethoxy, 2-hydroxyethoxy, 2-methoxyethoxy, 2-ethoxyethoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-(piperazin-1-yl)ethoxy, 3-(piperazin-1-yl)propoxy, 2-(4-methylpiperazin-1-yl)ethoxy, 3-(4-methylpiperazin-1-yl)propoxy, 2-hydroxyethylamino, 2-methoxyethylamino, 2-ethoxyethylamino, 3-methoxypropylamino, 2-dimethylaminoethylamino, 3-dimethylaminopropylamino, 2-(pyrrolidin-1-yl)ethylamino, 3-(pyrrolidin-1-yl)propylamino, 2-piperidinoethylamino, 3-piperidinopropylamino, 2-morpholinoethylamino, 3-morpholinopropylamino, 2-(piperazin-1-yl)ethylamino, 3-(piperazin-1-yl)propylamino, 2-(4-methylpiperazin-1-yl)ethylamino, 3-(4-methylpiperazin-1-yl)propylamino, acetamido, 2-chloroacetamido, 2-methylaminoacetamido, 2-ethylaminoacetamido, 2-dimethylaminoacetamido or 2-diethylaminoacetamido, or $(R^1)_m$ is a 6,7-methylenedioxy group;

n is 0, 1 or 2 and each $R^2$ is independently fluoro, chloro, bromo, cyano, methyl or ethyl;

X is a group of the formula CO, $C(R^3)_2$, $CH(OR^3)$, O, S, $SO_2$, $CONR^3$, $SO_2NR^3$, $NR^3CO$, $NR^3SO_2$, $OC(R^3)_2$ or $SC(R^3)_2$ wherein each $R^3$ is independently hydrogen or methyl; and Q is a phenyl group which is optionally substituted with 1 or 2 substituents selected from fluoro, chloro, bromo, trifluoromethyl, cyano, carbamoyl, methyl and methoxy, or Q is a 5- or 6-membered heteroaryl moiety selected from furyl, thienyl, oxazolyl, imidazolyl, thiazolyl, pyridyl, pyrimidinyl and 1,2,4-triazolyl which is optionally substituted with 1 or 2 substituents selected from fluoro, chloro, methyl, ethyl, methoxy and ethoxy; or a pharmaceutically-acceptable salt thereof.

A further preferred compound of the invention is an aniline derivative of the formula I wherein m is 1 with the substituent located at the 6-position or m is 2 with the substituents located at the 6- and 7-positions and each $R^1$ is hydroxy, amino, methoxy, ethoxy, acetoxy, methylamino, ethylamino, 2-bromoethoxy, 2,2,2-trifluoroethoxy, 2-hydroxyethoxy, 2-methoxyethoxy, 2-ethoxyethoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-hydroxyethylamino, 2-methoxyethylamino, 2-ethoxyethylamino, acetamido, 2-chloroacetamido, 2-methylaminoacetamido, 2-ethylaminoacetamido, 2-dimethylaminoacetamido or 2-diethylaminoacetamido, or $(R^1)_m$ is a 6,7-methylenedioxy group;

n is 0 or n is 1 and $R^2$ is fluoro, chloro, cyano, methyl or ethyl;

X is a group of the formula CO, $C(R^3)_2$, $CH(OR^3)$, O, S, $SO_2$, $CONR^3$, $SO_2NR^3$, $OC(R^3)_2$ or $SC(R^3)_2$ wherein each $R^3$ is independently hydrogen or methyl; and Q is a phenyl group which is optionally substituted with 1 or 2 substituents selected from fluoro, chloro, bromo, trifluoromethyl, cyano and carbamoyl, or Q is a 5- or 6-membered heteroaryl moiety selected from furyl, thienyl, pyridyl, oxazolyl, imidazolyl, thiazolyl, pyrimidinyl and 1,2,4-triazolyl which is optionally substituted with 1 or 2 substituents selected from fluoro, chloro, methyl, ethyl, methoxy and ethoxy;

or a pharmaceutically-acceptable salt thereof.

A further preferred compound of the invention is an aniline derivative of the formula I wherein m is 1 with the substituent located at the 6-position or m is 2 with the substituents located at the 6- and 7-positions and each $R^1$ is hydroxy, methoxy, ethoxy, acetoxy, 2-bromoethoxy, 2,2,2-trifluoroethoxy, 2-hydroxyethoxy, 2-methoxyethoxy, 2-ethoxyethoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy or 3-diethylaminopropoxy, or $(R^1)_m$ is a 6,7-methylenedioxy group;

n is 0 or n is 1 and $R^2$ is fluoro, chloro, cyano, methyl or ethyl;

X is a group of the formula CO, $C(R^3)_2$, $CH(OR^3)$, O, S, $SO_2$, $CONR^3$, $SO_2NR^3$, $OC(R^3)_2$ or $SC(R^3)_2$ wherein each $R^3$ is independently hydrogen or methyl; and Q is a phenyl group which is optionally substituted with 1 or 2 substituents selected from fluoro, chloro, bromo, trifluoromethyl, cyano and carbamoyl, or Q is a 5- or 6-membered heteroaryl moiety selected from furyl, thienyl, pyridyl, oxazolyl, imidazolyl, thiazolyl, pyrimidinyl and 1,2,4-triazolyl which is optionally substituted with one or two substituents selected from fluoro, chloro, methyl, ethyl, methoxy and ethoxy;

or a pharmaceutically-acceptable salt thereof.

A further preferred compound of the invention is an aniline derivative of the formula I wherein m is 1 or 2 and each $R^1$ is hydroxy, methoxy, ethoxy, 2-hydroxyethoxy, 2-methoxyethoxy, 2-methylaminoethoxy or 2-dimethylaminoethoxy, or $(R^1)_m$ is a methylenedioxy group;

n is 0 or n is 1 and $R^2$, which is located ortho to the group of formula —X—Q, is fluoro, chloro, cyano, methyl or ethyl;

X is a group of the formula CO, $C(R^3)_2$, $CH(OR^3)$, O, S, $SO_2$, $CONR^3$, $SO_2NR^3$, $OC(R^3)_2$ or $SC(R^3)_2$ wherein each $R^3$ is independently hydrogen or methyl; and Q is a phenyl group which is optionally substituted with 1 or 2 substituents selected from fluoro, chloro, bromo, trifluoromethyl, cyano and carbamoyl, or Q is a 5- or 6-membered heteroaryl moiety selected from furyl, thienyl, pyridyl, oxazolyl, imidazolyl, thiazolyl, pyrimidinyl and 1,2,4-triazolyl which is optionally substituted with a substituent selected from methyl and ethyl;

or a pharmaceutically-acceptable salt thereof.

A further preferred compound of the invention is an aniline derivative of the formula I wherein m is 1 with the substituent located at the 6-position or m is 2 with the substituents located at the 6- and 7-positions and each $R^1$ is hydroxy, amino, methoxy, ethoxy, acetoxy, methylamino, ethylamino, 2-bromoethoxy, 2,2,2-trifluoroethoxy, 2-hydroxyethoxy, 2-methoxyethoxy, 2-methylaminoethoxy, 3-methylaminopropoxy, 2-dimethylaminoethoxy, 3-dimethylaminopropoxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-(piperazin-1-yl)ethoxy, 3-(piperazin-1-yl)propoxy, 2-(4-methylpiperazin-1-yl)ethoxy, 3-(4-methylpiperazin-1-yl)propoxy, 2-hydroxyethylamino, 2-methoxyethylamino, 3-methoxypropylamino, 2-dimethylaminoethylamino, 3-dimethylaminopropylamino, 2-(pyrrolidin-1-yl)ethylamino, 3-(pyrrolidin-1-yl)propylamino, 2-piperidinoethylamino, 3-piperidinopropylamino, 2-morpholinoethylamino, 3-morpholinopropylamino, 2-(piperazin-1-yl)ethylamino, 3-(piperazin-1-yl)propylamino, 2-(4-methylpiperazin-1-yl)ethylamino, 3-(4-methylpiperazin-1-yl)propylamino, acetamido, 2-chloroacetamido, 2-methylaminoacetamido, 2-ethylaminoacetamido, 2-dimethylaminoacetamido or 2-diethylaminoacetamido, or $(R^1)_m$ is a 6,7-methylenedioxy group;

n is 0, 1 or 2 and each $R^2$ is independently fluoro, chloro, bromo, cyano, methyl or ethyl;

X is a group of the formula CO, $CH_2$, CH(OH), O, S, $SO_2$, CONH, $SO_2NH$, NHCO, $NHSO_2$ or $OCH_2$; and Q is a phenyl group which is optionally substituted with 1 or 2 substituents selected from fluoro, chloro, bromo, trifluoromethyl, cyano, carbamoyl, methyl and methoxy, or Q is a 5- or 6-membered heteroaryl moiety selected from furyl, thienyl, oxazolyl, imidazolyl, thiazolyl and pyridyl which is optionally substituted with 1 or 2 substituents selected from fluoro, chloro, methyl, ethyl, methoxy and ethoxy;

or a pharmaceutically-acceptable salt thereof.

A further preferred compound of the invention is an aniline derivative of the formula I wherein $(R^1)_m$ is 6,7-dimethoxy;

n is 1 and $R^2$, which is located ortho to the group of formula —X—Q, is fluoro, chloro or methyl.

X is a group of the formula CO, $CH_2$, CH(OH), O, S, $SO_2$, CONH, $SO_2NH$ or $OCH_2$; and Q is a phenyl group which is optionally substituted with 1 or 2 substituents selected from fluoro, chloro, trifluoromethyl, cyano and carbamoyl, or Q is 2-furyl, 3-furyl, 2-thienyl, 3-thienyl, 2-pyridyl, 3-pyridyl, 4-pyridyl, 2-oxazolyl, 4-oxazolyl, 5-oxazolyl, 2-imidazolyl, 1-methylimidazol-2-yl, 4-imidazolyl, 1-methylimidazol-4-yl, 5-imidazolyl, 1-methylimidazol-5-yl, 2-thiazolyl, 4-thiazolyl or 5-thiazolyl;

or a pharmaceutically-acceptable acid-addition salt thereof.

A further preferred compound of the invention is an aniline derivative of the formula I wherein $(R^1)_m$ is 6,7-dimethoxy, 6-methoxy-7-(2,2,2-trifluoroethoxy), 6-(2-dimethylaminoethoxy)-7-methoxy, 6-(3-dimethylaminopropoxy)-7-methoxy, 6-(2-morpholinoethoxy)-7-methoxy, 6-(3-morpholinopropoxy)-7-methoxy, 6-(2-dimethylaminoethoxy), 6-(3-dimethylaminopropoxy), 6-(2-morpholinoethoxy), 6-(3-morpholinopropoxy), 6-amino, 6-acetamido, 6-(2-chloroacetamido), 6-(2-methylaminoacetamido), 6-(2-methoxyethylamino), 6-(2-dimethylaminoethylamino)-7-methoxy, 6-(3-dimethylaminopropylamino)-7-methoxy, 6-(2-morpholinoethylamino)-7-methoxy or 6-(3-morpholinopropylamino)-7-methoxy;

n is 1 or 2 and $R^2$ is fluoro, chloro or methyl;

X is a group of formula $OCH_2$; and

Q is 2-furyl, 3-furyl, 2-thienyl, 2-pyridyl or 1-methylimidazol-2-yl;

or a pharmaceutically-acceptable acid-addition salt thereof.

A further preferred compound of the invention is an aniline derivative of the formula I wherein $(R^1)_m$ is 6,7-dimethoxy;

n is 1 and $R^2$, which is located ortho to the group of formula —X—Q, is chloro or methyl;

X is a group of the formula CO, $CH_2$, CH(OH), S, $SO_2NH$ or $OCH_2$; and

Q is phenyl, 3-furyl, 2-pyridyl, 4-pyridyl or 5-thiazolyl;

or a pharmaceutically-acceptable acid-addition salt thereof.

A further preferred compound of the invention is an aniline derivative of the formula I wherein $(R^1)_m$ is 6,7-dimethoxy;

n is 1 and $R^2$ is fluoro, chloro or methyl;

X is a group of the formula $OCH_2$; and

Q is 2-furyl, 3-furyl, 2-thienyl, 2-pyridyl or 1-methylimidazol-2-yl;

or a pharmaceutically-acceptable acid-addition salt thereof.

A specific preferred compound of the invention is the following aniline derivative of the formula I:

4-(4-benzoyl-3-chloroanilino)-6,7-dimethoxyquinazoline,
4-{3-chloro-4-[1-hydroxy-1-(4-pyridyl)methyl]anilino}-6,7-dimethoxyquinazoline,
4-(4-benzyl-3-chloroanilino)-6,7-dimethoxyquinazoline,
4-(3-chloro-4-phenylthioanilino)-6,7-dimethoxyquinazoline,
4-[3-chloro-4-(1-methylimidazol-2-ylthio)anilino]-6,7-dimethoxyquinazoline,
6,7-dimethoxy-4-[4-(N-phenylsulphamoyl)anilino]quinazoline or
6,7-dimethoxy-4-[3-methyl-4-(2-pyridylmethoxy)anilino]quinazoline;

or a pharmaceutically-acceptable acid-addition salt thereof.

A further specific preferred compound of the invention is the following aniline derivative of the formula I:

4-[3-chloro-4-(4-fluorobenzoyl)anilino)-6,7-dimethoxyquinazoline,
4-[2-fluoro-4-(2-pyridylmethoxy)anilino]-6,7-dimethoxyquinazoline,
4-[3-fluoro-4-(2-pyridylmethoxy)anilino]-6,7-dimethoxyquinazoline,
4-[3-chloro-4-(2-pyridylmethoxy)anilino]-6,7-dimethoxyquinazoline or
4-[3-chloro-4-(1-methylimidazol-2-ylmethoxy)anilino]-6,7-dimethoxyquinazoline;

or a pharmaceutically-acceptable acid-addition salt thereof.

A further specific preferred compound of the invention is the following aniline derivative of the formula I:

6,7-dimethoxy-4-[3-methyl-4-(1-methylimidazol-2-ylmethoxy)anilino]quinazoline,
6,7-dimethoxy-4-[3-methyl-4-(2-thiazolylmethoxy)anilino]quinazoline,
4-[3-fluoro-4-(2-pyridylmethoxy)anilino]-6,7-dimethoxyquinazoline,
4-[2-fluoro-4-(2-pyridylmethoxy)anilino]-6-(3-morpholinopropoxy)quinazoline,
6-(3-dimethylaminopropoxy)-7-methoxy-4-[3-methyl-4-(2-pyridylmethoxy)anilino]quinazoline,
7-methoxy-4-[3-methyl-4-(2-pyridylmethoxy)anilino]-6-(3-morpholinopropoxy)quinazoline or
4-[2-fluoro-4-(2-pyridylmethoxy)anilino]-6-(2-methoxyethylamino)quinazoline;

or a pharmaceutically-acceptable acid-addition salt thereof.

An especially preferred compound of the invention is the following aniline derivative of the formula I:

6,7-dimethoxy-4-[3-methyl-4-(2-pyridylmethoxy)anilino]quinazoline;

or a pharmaceutically-acceptable acid-addition salt thereof.

An aniline derivative of the formula I, or a pharmaceutically-acceptable salt thereof, may be prepared by any process known to be applicable to the preparation of chemically-related compounds. Suitable processes include, for example, those illustrated in European Patent Applications Nos. 0520722, 0566226, 0602851, 0635507 and 0635498. Such processes, when used to prepare an aniline derivative of the formula I, or a pharmaceutically-acceptable salt thereof, are provided as a further feature of the invention and are illustrated by the following representative examples in which, unless otherwise stated, m, $R^1$, n, $R^2$, X and Q have any of the meanings defined hereinbefore for an aniline derivative of the formula I. Necessary starting materials may be obtained by standard procedures of organic chemistry. The preparation of such starting materials is described within the accompanying non-limiting- Examples. Alternatively necessary starting materials are obtainable by analogous procedures to those illustrated which are within the ordinary skill of an organic chemist.

(a) The reaction, optionally in the presence of a suitable base, of a quinazoline of the formula II (set out hereinafter), wherein Z is a displaceable group, with an aniline of the formula III.

A suitable displaceable group Z is, for example, a halogeno, alkoxy, aryloxy or sulphonyloxy group, for example a chloro, bromo, methoxy, phenoxy, methanesulphonyloxy or toluene-p-sulphonyloxy group.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide. Alternatively a suitable base is, for example, an alkali metal or alkaline earth metal amide, for example sodium amide or sodium bis(trimethylsilyl)amide.

The reaction is preferably carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10° to 150° C., preferably in the range 20° to 80° C.

The aniline derivative of the formula I may be obtained from this process in the form of the free base or alternatively it may be obtained in the form of a salt with the acid of the formula H—Z wherein Z has the meaning defined hereinbefore. When it is desired to obtain the free base from the salt, the salt may be treated with a suitable base as defined hereinbefore using a conventional procedure.

(b) For the production of those compounds of the formula I wherein $R^1$ or $R^2$ is hydroxy, the cleavage of an aniline derivative of the formula I wherein $R^1$ or $R^2$ is (1–4C)alkoxy.

The cleavage reaction may conveniently be carried out by any of the many procedures known for such a transformation. The reaction may be carried out, for example, by treatment of the aniline derivative with an alkali metal (1–4C)alkylsulphide such as sodium ethanethiolate or, for example, by treatment with an alkali metal diarylphosphide such as lithium diphenylphosphide. Alternatively the cleavage reaction may conveniently be carried out, for example, by treatment of the aniline derivative with a boron or aluminium trihalide such as boron tribromide. Such reactions are preferably carried out in the presence of a suitable inert solvent or diluent as defined hereinbefore and at a suitable temperature as conventionally used with each of the above-mentioned cleavage reagents.

(c) For the production of those compounds of the formula I wherein $R^1$ is amino or hydroxyamino, the reduction of an aniline derivative of the formula I wherein $R^1$ is nitro.

The reduction may conveniently be carried out by any of the many procedures known for such a transformation. The reduction may be carried out, for example, by the hydrogenation of a solution of the nitro compound in an inert solvent or diluent as defined hereinbefore in the presence of a suitable metal catalyst such as palladium or platinum. A further suitable reducing agent is, for example, an activated metal such as activated iron (produced by washing iron powder with a dilute solution of an acid such as hydrochloric acid). Thus, for example, the reduction may be carried out by heating a mixture of the nitro compound and the activated metal in a suitable solvent or diluent such as a mixture of water and an alcohol, for example, methanol or ethanol, to a temperature in the range, for example, 50° to 150° C., conveniently at or near 70° C.

(d) For the production of those compounds of the formula I wherein $R^1$ is (2–4C)alkanoylamino, substituted (2–4C)alkanoylamino, (3–4C)alkenoylamino, (3–4C) alkynoylamino, N-(1–4C)alkyl-(2–4C)alkanoylamino, substituted N-(1–4C)alkyl-(2–4C)-alkanoylamino, N-(1–4C)alkyl-(3–4C)alkenoylamino or N-(1–4C) alkyl-(2–4C)alkynoylamino or $R^2$ is (2–4C) alkanoylamino, the acylation of an aniline derivative of the formula I wherein $R^1$ or $R^2$ is amino.

A suitable acylating agent is, for example, any agent known in the art for the acylation of amino to acylamino, for example an acyl halide, for example a (2–4C)alkanoyl chloride or bromide, conveniently in the presence of a suitable base, as defined hereinbefore, an alkanoic acid anhydride or mixed anhydride, for example a (2–4C) alkanoic acid anhydride such as acetic anhydride or the mixed anhydride formed by the reaction of an alkanoic acid and a (1–4C)alkoxycarbonyl halide, for example a (1–4C) alkoxycarbonyl chloride, in the presence of a suitable base as defined hereinbefore. In general the acylation is carried out in a suitable inert solvent or diluent as defined hereinbefore and at a temperature, in the range, for example, −30° to 120° C., conveniently at or near ambient temperature.

(e) For the production of those compounds of the formula I wherein $R^1$ is (1–4C)alkoxy or substituted (1–4C) alkoxy or $R^1$ is (1–4C)alkylamino, di-[(1–4C)alkyl] amino or substituted (1–4C)alkylamino, the alkylation, preferably in the presence of a suitable base as defined hereinbefore, of an aniline derivative of the formula I wherein $R^1$ is hydroxy or amino as appropriate.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1–4C)alkyl chloride, bromide or iodide or a substituted (1–4C)alkyl chloride, bromide or iodide, in the presence of a suitable base as defined hereinbefore, in a suitable inert solvent or diluent as defined hereinbefore and at a temperature in the range, for example, 10° to 140° C., conveniently at or near ambient temperature.

(f) For the production of those compounds of the formula I wherein X is a group of the formula CH(OH) or $CH_2$, the reduction of a compound of the formula I wherein X is a group of the formula CO.

The reduction may be carried out by any of the many procedures known for such transformations. The reduction to form a compound of the formula I wherein X is a group of the formula CH(OH) may be carried out, for example, by the reduction of a compound of the formula I wherein X is a group of the formula CO with a hydride reducing agent, for example an alkali metal borohydride or cyanoborohydride such as sodium borohydride or sodium cyanoborohydride, or an alkali metal aluminium hydride such as lithium aluminium hydride. The reduction may be carried out in the presence of a suitable inert solvent or diluent, for example a (1–4C)alcohol such as methanol or ethanol when an alkali metal borohydride or cyanoborohydride is employed, or an inert ether such as diethyl ether or tetrahydrofuran when an alkali metal aluminium hydride is employed. The reduction to form a compound of the formula I wherein X is a group of the formula $CH_2$ may be carried out, for example, by the reduction of a compound of the formula I wherein X is a group of the formula CO with a hydride reducing agent, for example an alkali metal aluminium hydride such as lithium aluminium hydride. Alternatively the reduction of a compound of the formula I wherein X is a group of the formula CO may be carried out in two steps, a first reduction step as described hereinbefore to provide a compound of the formula I wherein X is a group of the formula CH(OH) and a second reduction step to provide a compound of the formula I wherein X is a group of the formula $CH_2$. The second reduction step may be carried out by any of the many procedures known for such a transformation, for example the compound of the formula I wherein X is a group of the formula CH(OH) may be reacted with a tri-(1–4C)alkylsilyl halide such as trimethylsilyl chloride or an aryl-di-(1–4C) alkyl halide such as phenyldimethylsilyl chloride and the material so obtained may be reacted with an alkali metal halide such as sodium iodide. The reduction may be carried out in a suitable inert solvent or diluent such as acetonitrile.

(g) For the production of those compounds of the formula I wherein X is a group of the formula SO or $SO_2$, the oxidation of an aniline derivative of the formula I wherein X is a group of the formula S.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinium. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature in the range, for example, –25° to 50° C., conveniently at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a (1–4C)alkylsulphonyl group is required, it may be obtained by oxidation of the corresponding (1–4C)alkylsulphinyl compound as well as of the corresponding (1–4C)alkylthio compound.

(h) For the production of those compounds of the formula I wherein $R^1$ is (2–4C)alkanoyloxy, the acylation, optionally in the presence of a suitable base as defined hereinbefore, of an aniline derivative of the formula I wherein $R^1$ is hydroxy.

A suitable acylating agent is, for example, any agent known in the art for the acylation of hydroxy to acyloxy, for example any of the acylating agents disclosed in paragraph (d) hereinbefore which may conveniently be used according to the reaction conditions disclosed therein.

(i) For the production of those compounds of the formula I wherein $R^1$ is hydroxy, the hydrolysis, optionally in the presence of a suitable base, of an aniline derivative of the formula I wherein $R^1$ is (2–4C)alkanoyloxy.

The hydrolysis reaction may conveniently be carried out by any of the many procedures known in the art for such a transformation. The reaction may be carried out, for example, by hydrolysis under acidic or basic conditions. A suitable base is, for example, an alkali metal, alkaline earth metal or ammonium carbonate or hydroxide, for example sodium carbonate, potassium carbonate, sodium hydroxide, potassium hydroxide or ammonium hydroxide. The reaction is preferably carried out in the presence of water and a suitable solvent or diluent such as methanol or ethanol. The reaction is conveniently carried out at a temperature in the range 10° to 150° C., preferably at or near ambient temperature.

(j) For the production of those compounds of the formula I wherein $R^1$ is a (2–4C)alkoxy group which bears a hydroxy, amino, substituted hydroxy or substituted amino group, the reaction, preferably in the presence of a suitable base as defined hereinbefore, of a compound of the formula I wherein $R^1$ is a hydroxy-(2–4C)alkoxy group, or a reactive derivative thereof, with water, ammonia, an alcohol or an amine as appropriate.

A suitable reactive derivative of a compound of the formula I wherein $R^1$ is a hydroxy-(2–4C)alkoxy group is, for example, a halogeno- or sulphonyloxy-(2–4C)alkoxy group such as a bromo- or methanesulphonyloxy-(2–4C) alkoxy group.

The reaction is preferably carried out in the presence of a suitable inert solvent or diluent as defined hereinbefore and at a temperature in the range, for example, 10° to 150° C., conveniently at or near 50° C.

(k) For the production of those compounds of the formula I wherein X is a group of the formula $OC(R^3)_2$, the alkylation, preferably in the presence of a suitable base as defined hereinbefore, of a phenol of the formula IV with an alkylating agent of the formula $Z-C(R^3)_2-Q$ wherein Z is a displaceable group as defined hereinbefore.

The reaction is conveniently carried out in the presence of a suitable inert solvent or diluent as defined hereinbefore and at a temperature in the range, for example, 10° to 150° C., preferably in the range 20° to 80° C.

(l) For the production of those compounds of the formula I wherein $R^1$ is (1–4C)alkylamino or substituted (2–4C)alkylamino, the reductive amination of formaldehyde, a (2–4C)alkanoaldehyde or a substituted (2–4C)alkanoaldehyde.

A suitable (2–4C)alkanoaldehyde is, for example, acetaldehyde or propionaldehyde. A suitable substituted (2–4C) alkanoaldehyde is, for example, 2-methoxyacetaldehyde, 3-methoxypropionaldehyde, 2-dimethylaminoacetaldehyde, 3-dimethylaminopropionaldehyde, 2-morpholinoacetaldehyde or 3-morpholinopropionaldehyde.

The reduction may be carried out by any of the many procedures known for such a transformation. For example a hydride reducing agent may be used, for example an alkali metal borohydride or cyanoborohydride such as sodium borohydride or sodium cyanoborohydride, or an alkali metal aluminium hydride such as lithium aluminium hydride. The reduction may be carried out in the presence of a suitable inert solvent or diluent, for example a (1–4C)alcohol such as methanol or ethanol when an alkali metal borohydride or cyanoborohydride is employed, or an inert ether such as diethyl ether or tetrahydrofuran when an alkali metal aluminium hydride is employed.

The reaction is conveniently carried out at a temperature in the range, for example, –10° to 100° C. conveniently at or near ambient temperature.

When a pharmaceutically-acceptable salt of an aniline derivative of the formula I is required, for example an acid-addition salt of an aniline derivative of the formula I, it may be obtained, for example, by reaction of said compound with, for example, a suitable acid using a conventional procedure.

As stated hereinbefore the aniline derivatives defined in the present invention possesses anti-proliferative activity which is believed to arise from the Class I receptor tyrosine kinase inhibitory activity of the compounds. These properties may be assessed, for example, using one or more of the procedures set out below:

(a) An in vitro assay which determines the ability of a test compound to inhibit the enzyme EGF receptor tyrosine kinase. Receptor tyrosine kinase was obtained in partially purified form from A-431 cells (derived from human vulval carcinoma) by procedures related to those described by Carpenter et al., *J. Biol. Chem.*, 1979, 254, 4884, Cohen et al., *J. Biol. Chem.*, 1982, 257, 1523 and by Braun et al., *J. Biol. Chem.*, 1984, 259, 2051.

A-431 cells were grown to confluence using Dulbecco's modified Eagle's medium (DHEM) containing 5% fetal calf serum (FCS). The obtained cells were homogenised in a hypotonic borate/EDTA buffer at pH 10.1. The homogenate was centrifuged at 400 g for 10 minutes at 0°–4° C. The supernatant was centrifuged at 25,000 g for 30 minutes at 0°–4° C. The pelleted material was suspended in 30 mM Hepes buffer at pH 7.4 containing 5% glycerol, 4 mM benzamidine and 1% Triton X-100, stirred for 1 hour at 0°–4° C., and recentrifuged at 100,000 g for 1 hour at 0°–4° C. The supernatant, containing solubilised receptor tyrosine kinase, was stored in liquid nitrogen.

For test purposes 40 $\mu$l of the enzyme solution so obtained was added to a mixture of 400 $\mu$l of a mixture of 150 mM Hepes buffer at pH 7.4, 500 $\mu$M sodium orthovanadate, 0.1% Triton X-100, 10% glycerol, 200 $\mu$l water, 80 $\mu$l of 25 mH DTT and 80 $\mu$l of a mixture of 12.5 mM manganese chloride, 125 mM magnesium chloride and distilled water. There was thus obtained the test enzyme solution.

Each test compound was dissolved in dimethylsulphoxide (DMSO) to give a 50 mM solution which was diluted with 40 mM Hepes buffer containing 0.1% Triton X-100, 10% glycerol and 10% DMSO to give a 500 $\mu$M solution. Equal volumes of this solution and a solution of epidermal growth factor (EGF; 20 $\mu$g/ml) were mixed.

[$\gamma$-$^{32}$P]ATP (3000 Ci/mM, 250 $\mu$Ci) was diluted to a volume of 2 ml by the addition of a solution of ATP (100 $\mu$M) in distilled water. An equal volume of a 4 mg/ml solution of the peptide Arg-Arg-Leu-Ile-Glu-Asp-Ala-Glu-Tyr-Ala-Ala-Arg-Gly in a mixture of 40 mH Hepes buffer at pH 7.4, 0.1% Triton X-100 and 10% glycerol was added.

The test compound/EGF mixture solution (5 $\mu$l) was added to the test enzyme solution (10 $\mu$l) and the mixture was incubated at 0°–4° C. for 30 minutes. The ATP/peptide mixture (10 $\mu$l) was added and the mixture was incubated at 25° C. for 10 minutes. The phosphorylation reaction was terminated by the addition of 5% trichloroacetic acid (40 $\mu$l) and bovine serum albumin (BSA; 1 mg/ml, 5 $\mu$l). The mixture was allowed to stand at 4° C. for 30 minutes and then centrifuged. An aliquot (40 $\mu$l) of the supernatant was placed onto a strip of Whatman p 81 phosphocellulose paper. The strip was washed in 75 mH phosphoric acid (4×10 ml) and blotted dry. Radioactivity present in the filter paper was measured using a liquid scintillation counter (Sequence A). The reaction sequence was repeated in the absence of the EGF (Sequence B) and again in the absence of the test compound (Sequence C).

Receptor tyrosine kinase inhibition was calculated as follows:

$$\% \text{ Inhibition} = \frac{100 - (A - B)}{C - B} \times 100$$

The extent of inhibition was then determined at a range of concentrations of test compound to give an IC$_{50}$ value.

(b) An in vitro assay which determines the ability of a test compound to inhibit the EGF-stimulated growth of the human naso-pharyngeal cancer cell line KB.

KB cells were seeded into wells at a density of 1×10$^4$–1.5×10$^4$ cells per well and grown for 24 hours in DHEM supplemented with 5% FCS (charcoal-stripped). Cell growth was determined after incubation for 3 days by the extent of metabolism of MTT tetrazolium dye to furnish a bluish colour. Cell growth was then determined in the presence of EGF (10 ng/ml) or in the presence of EGF (10 ng/ml) and a test compound at a range of concentrations. An IC$_{50}$ value could then be calculated.

(c) An in vivo assay in a group of male rats which determines the ability of a test compound (usually administered orally as a ball-milled suspension in 0.5% polysorbate) to inhibit the stimulation of liver hepatocyte growth caused by the administration of the growth factor TGF$\alpha$ (400 $\mu$g/kg subcutaneously, usually dosed twice, 3 and 7 hours respectively after the administration of the test compound).

In a control group of rats, the administration of TGF$\alpha$ causes on average a 5-fold stimulation of liver hepatocyte growth.

Cell-growth in the control and test animals is determined as follows:

On the morning of the day after the dosing of the test compound (or 0.5% polysorbate in the control group), the animals are dosed with bromodeoxyuridine (BrdU; 100 mg/kg intraperitoneally). The animals are killed four hours later and the livers are excised. Slices are cut from each liver and the uptake of BrdU is determined by a conventional immunohistochemical technique similar to that described on pages 267 and 268 of an article by Goldsworthy et al. in Chemically Induced Cell Proliferation: Implications for Risk Assessment, Wiley-Liss Inc., 1991, pages 253–284.

Further tests were carried out using a range of doses of the test compounds to allow the calculation of an approximate ED$_{50}$ value for the inhibition of liver hepatocyte proliferation as determined by inhibition of the uptake of BrdU.

(d) An in-vivo assay in a group of athymic nude mice (strain ONU:Alpk) which determines the ability of a test compound (usually administered orally as a ball-milled suspension in 0.5% polysorbate) to inhibit the growth of xenografts of the human vulval epidermoid carcinoma cell line A-431.

A-431 cells were maintained in culture in DHEM supplemented with 5% FCS and 2 mM glutamine. Freshly cultured cells were harvested by trypsinization and injected subcutaneously (10 million cells/0.1 ml/mouse) into both flanks of a number of donor nude mice. When sufficient tumour material was available (after approximately 9 to 14 days), fragments of tumour tissue were transplanted in the flanks of recipient nude mice (test day 0). Generally, on the seventh day after transplantation (test day 7) groups of 7 to 10 mice with similar-sized tumours were selected and dosing of the test compound was commenced. Once daily dosing of test compound was continued for a total of 13 days (test days 7 to 19 inclusive). In some studies the dosing of the test compound was continued beyond test day 19, for example to test day 26. In each case, on the following test day the animals were killed and the final tumour volume was calculated from measurements of the length and width of the tumours. Results were calculated as a percentage inhibition of tumour volume relative to untreated controls.

Although the pharmacological properties of the compounds of the formula I vary with structural change as expected, in general activity possessed by compounds of the formula I may be demonstrated at the following concentrations or doses in one or more of the above tests (a), (b), (c) and (d):

Test (a):—$IC_{50}$ in the range, for example, 0.001–1 $\mu M$;
Test (b):—$IC_{50}$ in the range, for example, 0.1–10 $\mu M$;
Test (c):—$ED_{50}$ in the range, for example, 1–100 mg/kg;
Test (d):—20 to 70% inhibition of tumour volume from a daily dose in the range, for example, 50 to 400 mg/kg.

Thus, by way of example, the compound 4-(4-benzoyl-3-chloroanilino)-6,7-dimethoxyquinazoline hydrochloride salt has an $IC_{50}$ of 0.03 $\mu M$ in Test (a), an $IC_{50}$ of 0.38 $\mu M$ in Test (b) and an $ED_{50}$ of <5 mg/kg in Test (c);

4-(4-benzyl-3-chloroanilino)-6,7-dimethoxyquinazoline hydroiodide salt has an $IC_{50}$ of 0.1 $\mu M$ in Test (a), an $IC_{50}$ of 1.2 $\mu M$ in Test (b) and an $ED_{50}$ of <12.5 mg/kg in Test (c);

4-(3-chloro-4-phenylthioanilino)-6,7-dimethoxyquinazoline has an $IC_{50}$ of 0.08 $\mu M$ in Test (a), an $IC_{50}$ of 1.3 $\mu M$ in Test (b) and an $ED_{50}$ of 12.5 mg/kg in Test (c);

4-[3-chloro-4-(1-methylimidazol-2-ylthio)anilino]-6,7-dimethoxyquinazoline dihydrochloride salt has an $IC_{50}$ of 0.007 $\mu M$ in Test (a), an $IC_{50}$ of 0.2 $\mu M$ in Test (b) and an $ED_{50}$ of <12.5 mg/kg in Test (c);

6,7-dimethoxy-4-[3-methyl-4-(2-pyridylmethoxy)anilino]quinazoline dihydrochloride salt has an $IC_{50}$ of 0.04 $\mu M$ in Test (a), an $IC_{50}$ of 0.93 $\mu M$ in Test (b) and an $ED_{50}$ of 5 mg/kg in Test (c);

6-(3-dimethylaminopropoxy)-7-methoxy-4-[3-methyl-4-(2-pyridylmethoxy)anilino]quinazoline has an $IC_{50}$ of 0.066 $\mu M$ in Test (a) and an $IC_{50}$ of 0.43 $\mu M$ in Test (b); and 7-methoxy-4-[3-methyl-4-(2-pyridyl-methoxy)anilino]-6-(3-morpholinopropoxy)quinazoline has an $IC_{50}$ of 0.45 $\mu M$ in Test (a) and an $IC_{50}$ of 2.09 $\mu M$ in Test (b).

According to a further aspect of the invention there is provided a pharmaceutical composition which comprises an aniline derivative of the formula I, or a pharmaceutically-acceptable salt thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The aniline derivative will normally be administered to a warm-blooded animal at a unit dose within the range 5–10000 mg per square meter body area of the animal, i.e. approximately 0.1–200 mg/kg, and this normally provides a therapeutically-effective dose. A unit dose form such as a tablet or capsule will usually contain, for example 1–250 mg of active ingredient. Preferably a daily dose in the range of 1–100 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided an aniline derivative of the formula I as defined hereinbefore for use in a method of treatment of the human or animal body by therapy.

We have now found that the compounds of the present invention possess anti-proliferative properties such as anti-cancer properties which are believed to arise from their Class I receptor tyrosine kinase inhibitory activity. Accordingly the compounds of the present invention are expected to be useful in the treatment of diseases or medical conditions mediated alone or in part by Class I receptor tyrosine kinases, i.e. the compounds may be used to produce a Class I receptor tyrosine kinase inhibitory effect in a warm-blooded animal in need of such treatment. Thus the compounds of the present invention provide a method for treating the proliferation of malignant cells characterised by inhibition of Class I receptor tyrosine kinases, i.e. the compounds may be used to produce an anti-proliferative effect mediated alone or in part by the inhibition of Class I receptor tyrosine kinase. Accordingly the compounds of the present invention are expected to be useful in the treatment of psoriasis and/or cancer by providing an anti-proliferative effect, particularly in the treatment of Class I receptor tyrosine kinase sensitive cancers such as cancers of the breast, lung, colon, rectum, stomach, prostate, bladder, pancreas and ovary.

Thus according to this aspect of the invention there is provided the use of an aniline derivative of the formula I, or a pharmaceutically-acceptable salt thereof, as defined hereinbefore in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of an aniline derivative as defined immediately above.

As stated above the size of the dose required for the therapeutic or prophylactic treatment of a particular proliferative disease will necessarily be varied depending on the host treated, the route of administration and the severity of the illness being treated. A unit dose in the range, for example, 1–200 mg/kg, preferably 1–100 mg/kg is envisaged.

The anti-proliferative treatment defined hereinbefore may be applied as a sole therapy or may involve, in addition to the aniline derivative of the invention, conventional radiotherapy or one or more other anti-tumour substances, for example those selected from, for example, mitotic inhibitors, for example vinblastine; alkylating agents, for example cis-platin, carboplatin and cyclophosphamide; antimetabolites, for example 5-fluorouracil, cytosine arabinoside and hydroxyurea, or, for example, one of the preferred antimetabolites disclosed in European Patent Application No. 239362 such as N-{5-[N-(3,4-dihydro-2-methyl-4-oxoquinazolin-6-ylmethyl)-N-methylamino]-2-thenoyl}-L-glutamic acid; intercalating antibiotics, for example adriamycin and bleomycin; enzymes, for example asparaginase; topoisomerase inhibitors, for example etoposide; biological response modifiers, for example interferon; and anti-hormones, for example antioestrogens such as 'NOLVADEX' (tamoxifen) or, for example antiandrogens such as 'CASODEX' (4'-cyano-3-(4-fluorophenylsulphonyl)-2- hydroxy-2-methyl-3'-(trifluoromethyl)propionanilide. Such conjoint treatment may be achieved by way of the simultaneous, sequential or separate dosing of the individual components of the treatment. According to this aspect of the invention there is provided a pharmaceutical product comprising an aniline derivative of the formula I as defined hereinbefore and an additional anti-tumour substance as defined hereinbefore for the conjoint treatment of cancer.

As stated above the aniline derivative defined in the present invention is an effective anti-cancer agent, which property is believed to arise from its Class I receptor tyrosine kinase inhibitory properties. Such an aniline derivative of the invention is expected to possess a wide range of anti-cancer properties as Class I receptor tyrosine kinases have been implicated in many common human cancers such as leukaemia and breast, lung, colon, rectal, stomach, prostate, bladder, pancreas and ovarian cancer. Thus it is expected that an aniline derivative of the invention will possess anti-cancer activity against these cancers. It is in addition expected that an aniline derivative of the present invention will possess activity against a range of leukaemias, lymphoid malignancies and solid tumours such as carcinomas and sarcomas in tissues such as the liver, kidney, prostate and pancreas.

It is further expected that an aniline derivative of the invention will possess activity against other diseases involving excessive cellular proliferation such as psoriasis and BPH.

It is also to be expected that an aniline derivative of the invention will be useful in the treatment of additional disorders of cellular growth in which aberrant cell signalling by way of receptor tyrosine kinase enzymes, including as yet unidentified receptor tyrosine kinase enzymes, are involved. Such disorders include, for example, inflammation, angiogenesis, vascular restenosis, immunological disorders, pancreatitis, kidney disease and blastocyte maturation and implantation.

The invention will now be illustrated in the following non-limiting Examples in which, unless otherwise stated:

(i) evaporations were carried out by rotary evaporation in vacuo and work-up procedures were carried out after removal of residual solids such as drying agents by filtration, unless otherwise stated magnesium sulphate was used as a drying agent for organic solutions;

(ii) operations were carried out at ambient temperature, that is in the range 18°–25° C. and under an atmosphere of an inert gas such as argon;

(iii) column chromatography (by the flash procedure) and medium pressure liquid chromatography (HPLC) were performed on Herck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points were determined using a Hettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet, unless otherwise stated end-products of the formula I were dissolved in $CD_3SOCD_3$ for the determination of NMR values;

(vii) intermediates were not generally fully characterised and purity was assessed by thin layer chromatography (TLC), infra-red (IR) or NMR analysis;

(viii) the following abbreviations have been used:
DMF N,N-dimethylformamide;
THF tetrahydrofuran;
NMP N-methylpyrrolidin-2-one;
DMA N,N-dimethylacetamide;
DMSO dimethylsulphoxide.

EXAMPLE 1

A mixture of 4-chloro-6,7-dimethoxyquinazoline hydrochloride (European Patent Application No. 0566226; 1.1 g), 4-amino-2-chlorobenzophenone (1.05 g) and isopropanol (50 ml) was stirred and heated to reflux for 2 hours. The mixture was cooled to ambient temperature and the solid precipitate was isolated by filtration, washed with acetone and with diethyl ether and dried. The solid so obtained was recrystallised from a mixture of hexane, methylene chloride and methanol. There was thus obtained 4-(4-benzoyl-3-chloroanilino)-6,7-dimethoxyquinazoline hydrochloride salt (0.865 g, 45%), m.p. 256°–258° C.;

NMR Spectrum: 4.0 (s, 3H), 4.05 (s, 3H), 7.4 (s, 1H), 7.6 (m, 3H), 7.8 (m, 3H), 8.0 (m, 1H), 8.2 (d, 1H), 8.4 (s, 1H), 9.0 (s, 1H), 11.4 (broad s, 1H);

Elemental Analysis: Found C, 60.1; H, 4.2; N, 9.1; $C_{23}H_{18}ClN_3O_3$ 1HCl requires C, 60.5; H, 4.2; N, 9.2%.

The 4-amino-2-chlorobenzophenone used as a starting material was obtained as follows:

A mixture of 2-chloro-4-nitrobenzoic acid (20 g), thionyl chloride (40 ml) and DMF (5 drops) was stirred and heated to reflux for 1 hour. The mixture was evaporated to give 2-chloro-4-nitrobenzoyl chloride which was used without further purification.

Aluminium chloride (14 g) was added portionwise to a stirred mixture of the 2-chloro-4-nitrobenzoyl chloride so obtained and benzene (50 ml) which had been cooled to 5° C. The mixture was stirred at ambient temperature for 16 hours and then heated to reflux for 1 hour. The mixture was cooled to ambient temperature and added to a vigorously stirred mixture of ice and water. The stirring was continued and concentrated aqueous hydrochloric acid (30 ml) was added. The precipitate was isolated by filtration and dissolved in methylene chloride (250 ml). The organic solution was washed with aqueous sodium hydroxide solution (10%, 2×200 ml) and with brine, dried and evaporated. There was thus obtained 2-chloro-4-nitrobenzophenone as a solid (20 g, 77%).

A mixture of a portion (10 g) of the material so obtained, stannous chloride dihydrate (20 g) and concentrated aqueous hydrochloric acid (100 ml) was stirred and heated to reflux for 5 hours. The mixture was cooled to ambient temperature, poured onto a mixture of ice and water and basified by the addition of concentrated aqueous sodium hydroxide solution (30%). The mixture was extracted with diethyl ether and the organic phase was washed with brine, dried and evaporated. The residue was purified by column chromatography using increasingly polar mixtures of hexane and ethyl acetate as eluent. The resultant product was recrystallised from a mixture of hexane and methylene chloride. There was thus obtained 4-amino-2-chlorobenzophenone (2 g);

NMR Spectrum: 6.0 (s, 2H), 6.6 (m, 1H), 6.7 (d, 1H), 7.1 (d, 1H), 7.5 (m, 2H), 7.7 (m, 3H).

EXAMPLE 2

Using an analogous procedure to that described in Example 1, 4-amino-2-chlorophenyl 2-pyridyl ketone was reacted with 4-chloro-6,7-dimethoxyquinazoline hydrochloride to give 4-[3-chloro-4-(2-pyridylcarbonyl)anilino]-6,7-dimethoxyquinazoline dihydrochloride salt in 45% yield, m.p. 255°–258° C.;

NMR Spectrum: 4.0 (s, 3H), 4.05 (s, 3H), 7.4 (s, 1H), 7.7 (m, 2H), 8.1 (m, 3H), 8.5 (s, 1H), 8.7 (d, 1H), 9.0 (s, 1H), 11.8 (s, 1H); Elemental Analysis: Found C, 53.1; H, 4.3; N, 11.0; $C_{22}H_{17}ClN_4O_3$ 2HCl requires C, 53.5; H, 3.9; N, 11.3%.

The 4-amino-2-chlorophenyl 2-pyridyl ketone used as a starting material was obtained as follows:

n-Butyl lithium (1.6M in hexane, 12.5 ml) was added dropwise to a stirred solution of 3-chloro-4-iodonitrobenzene (5.6 g) in THF (150 ml) which had been cooled to −100° C. The mixture was stirred at −100° C. for 20 minutes. A solution of pyridine-2-carboxaldehyde (2.0 g) in THF (20 ml) was added. The mixture was allowed to warm to ambient temperature and was stirred for 16 hours. The mixture was partitioned between diethyl ether and a saturated aqueous ammonium chloride solution. The organic phase was washed with brine, dried and evaporated. The residue was purified by column chromatography using increasingly polar mixtures of methylene chloride and ethyl acetate as eluent. There was thus obtained 1-(2-chloro-4-nitrophenyl)-1-(2-pyridyl)methanol (2.3 g).

A mixture of the material so obtained, pyridinium chlorochromate (2.0 g) and methylene chloride (30 ml) was stirred at ambient temperature for 3 hours. The mixture was filtered and the filtrate was evaporated. The residue was purified by column chromatography using increasingly polar mixtures of methylene chloride and ethyl acetate as eluent. There was thus obtained 2-chloro-4-nitrophenyl 2-pyridyl ketone (1.4 g).

A mixture of a portion (0.5 g) of the material so obtained, iron powder (0.5 g) and ethanol (30 ml) was stirred and cooled in a salted ice-bath to 0° C. Hydrogen chloride gas was led into the mixture for 5 minutes. The mixture was stirred for 30 minutes and the reaction mixture was allowed to warm to 10° C. The mixture was basified by the addition of concentrated aqueous sodium hydroxide solution (30%) and extracted with ethyl acetate. The organic phase was washed with water, dried and evaporated. The residue was purified by column chromatography using increasingly polar mixtures of methylene chloride and ethyl acetate as eluent. There was thus obtained 4-amino-2-chlorophenyl 2-pyridyl ketone (0.25 g); NMR Spectrum: 6.1 (broad s, 2H), 6.5 (m, 1H), 6.6 (d, 1H), 7.3 (d, 1H), 7.6 (m, 1H), 7.8 (m, 1H), 8.0 (m, 1H), 8.6 (m, 1H).

EXAMPLE 3

Using an analogous procedure to that described in Example 1, 4-amino-2-chlorophenyl 5-thiazolyl ketone was reacted with 4-chloro-6,7-dimethoxyquinazoline hydrochloride to give 4-[3-chloro-4-(5-thiazolylcarbonyl)anilino]-6,7-dimethoxyquinazoline hydrochloride salt in 31% yield, m.p. 254°–257° C.;

NMR Spectrum: 4.02 (s, 3H), 4.09 (s, 3H), 7.32 (s, 1H), 7.91 (d, 2H), 8.14 (d, 1H), 8.2 (d, 1H), 8.28 (s, 1H), 8.37 (d, 1H), 8.93 (s, 1H), 11.3 (s, 1H).

The 4-amino-2-chlorophenyl 5-thiazolyl ketone used as a starting material was obtained as follows:

Triethylamine (20.9 ml) was added to a stirred mixture of 2-chloro-4-nitrobenzoyl chloride (30 g), N,O-dimethylhydroxylamine hydrochloride (14.62 g) and chloroform (300 ml) and the mixture was heated to reflux for 3 hours. The mixture was cooled to ambient temperature, washed with water, dried and evaporated. The residue was purified by column chromatography using methylene chloride as eluent. There was thus obtained 2-chloro-N-methoxy-N-methyl-4-nitrobenzamide.

n-Butyl lithium (1.6M in hexane, 3.67 ml) was added to a stirred mixture of 2-trimethylsilylthiazole (0.936 ml) and THF (50 ml) which had been cooled to −50° C. and the mixture was stirred at that temperature for 1 hour. A solution of 2-chloro-N-methoxy-N-methyl-4-nitrobenzamide (1.43 g) in THF (10 ml) was added. The mixture was stirred at −30° C. for 30 minutes and stored at ambient temperature for 16 hours. The mixture was partitioned between ethyl acetate and water. The organic phase was washed with water, dried and evaporated. The residue was purified by column chromatography using a 1:1 mixture of hexane and methylene chloride as eluent. There were thus obtained: 2-chloro-4-nitrophenyl 2-trimethylsilylthiazol-5-yl ketone (0.25 g) and 2-chloro-4-nitrophenyl 5-thiazolyl ketone (0.25 g).

The materials so obtained were recombined. Iron powder (0.26 g), concentrated hydrochloric acid (1 ml), water (4 ml) and ethanol (40 ml) were added and the mixture was stirred and heated to reflux for 4 hours. The mixture was cooled to ambient temperature, basified by the addition of 2M aqueous sodium hydroxide solution and extracted with methylene chloride. The organic phase was dried and evaporated. The residue was purified by column chromatography using increasingly polar mixtures of methylene chloride and methanol as eluent. There was thus obtained 4-amino-2-chlorophenyl 5-thiazolyl ketone (0.15 g);

NMR Spectrum: ($CDCl_3$) 6.59 (m, 1H), 6.7 (d, 1H), 6.75 (d, 1H), 7.7 (d, 1H), 8.02 (d, 1H).

EXAMPLE 4

A mixture of 4-(4-benzoyl-3-chloroanilino)-6,7-dimethoxyquinazoline hydrochloride (0.2 g), sodium borohydride (0.1 g) and ethanol (30 ml) was stirred at ambient temperature for 18 hours. The mixture was evaporated and the residue was acidified by the addition of glacial acetic acid. The mixture was partitioned between ethyl acetate and water. The organic phase was washed with water and with brine, dried and evaporated. The residue was triturated under a mixture of hexane and ethyl acetate. There was thus obtained 4-[3-chloro-4-(α-hydroxybenzyl)anilino]-6,7-dimethoxyquinazoline acetate salt (0.07 g, 35%), m.p. 159°–162° C.;

NMR Spectrum: 3.94 (s, 3H), 3.97 (s, 3H), 6.0 (broad s, 2H), 7.15–7.4 (m, 6H), 7.65 (d, 1H), 7.75–7.9 (m, 2H), 7.98 (d, 1H), 8.53 (s, 1H), 9.62 (broad s, 1H);

Elemental Analysis: Found C, 62.1; H, 5.0; N, 8.8; $C_{23}H_{20}ClN_3O_3$ $1MeCO_2H$ requires C, 62.3; H, 5.0; N, 8.7%.

EXAMPLE 5

Using an analogous procedure to that described in Example 1, 1-(4-amino-2-chlorophenyl)-1-(4-pyridyl)methanol was reacted with 4-chloro-6,7-dimethoxyquinazoline hydrochloride to give 4-{3-chloro-4-[1-hydroxy-1-(4-pyridyl)methyl]anilino}-6,7-dimethoxyquinazoline dihydrochloride salt in 12% yield;

NMR Spectrum: 4.0 (s, 3H), 4.05 (s, 3H), 6.25 (s, 1H), 7.4 (s, 1H), 7.66 (d, 1H), 7.9 (m, 1H), 8.0 (m, 3H), 8.55 (s, 1H), 8.85 (m, 3H), 11.8 (s, 1H);

Elemental Analysis: Found C, 51.2; H, 4.3; N, 10.8; $C_{22}H_{19}ClN_4O_3$ 2HCl 1H$_2$O requires C, 51.4; H, 4.5; N, 10.9%.

The 1-(4-amino-2-chlorophenyl)-1-(4-pyridyl)methanol used as a starting material was obtained as follows:

The procedures described in the portion of Example 2 which is concerned with the preparation of starting materials were repeated except that pyridine-4-carboxaldehyde was used in place of pyridine-2-carboxaldehyde. However over-reduction at the last stage meant that the expected product, 4-amino-2-chlorophenyl 4-pyridyl ketone, was reduced to give 1-(4-amino-2-chlorophenyl)-1-(4-pyridyl)-methanol in 8% yield;

NMR Spectrum: (CD$_3$SOCD$_3$+CD$_3$CO$_2$D) 5.9 (s, 1H), 6.5 (m, 1H), 6.6 (d, 1H), 7.1 (d, 1H), 7.4 (d, 2H), 8.5 (s, 2H).

EXAMPLE 6

Trimethylsilyl chloride (0.25 g) and sodium iodide (1.3 g) were added in turn to a stirred mixture of 4-[3-chloro-4-(α-hydroxybenzyl)anilino]-6,7-dimethoxyquinazoline acetate salt (0.5 g) and acetonitrile (20 ml) and the resultant mixture was stirred at ambient temperature for 2 hours. The mixture was partitioned between ethyl acetate and water. The organic phase was washed with a saturated aqueous sodium thiosulphate solution and with water, dried and evaporated. The solid residue was recrystallised from a mixture of hexane, methylene chloride and methanol. There was thus obtained 4-(4-benzyl-3-chloroanilino)-6,7-dimethoxyquinazoline hydroiodide salt (0.113 g, 12%), m.p. 200°–204° C.;

NMR Spectrum: 4.0 (s, 6H), 4.1 (s, 2H), 7.3 (m, 6H), 7.5 (d, 1H), 7.6 (m, 1H), 7.9 (d, 1H), 8.0 (s, 1H), 8.9 (s, 1H), 10.9 (s, 1H).

EXAMPLE 7

Using an analogous procedure to that described in Example 1 except that the reaction mixture was heated to reflux for 16 hours, 4-amino-2-chlorophenyl phenyl ether was reacted with 4-chloro-6,7-dimethoxyquinazoline hydrochloride to give 4-(3-chloro-4-phenoxyanilino)-6,7-dimethoxyquinazoline hydrochloride salt in 56% Yield, m.p. 260°–265° C.;

NMR Spectrum: 4.0 (s, 3H), 4.04 (s, 3H), 7.03 (d, 2H), 7.2 (m, 2H), 7.42 (m, 3H), 7.75 (m, 1H), 8.08 (d, 1H), 8.43 (s, 1H), 8.9 (s, 1H), 11.58 (s, 1H);

Elemental Analysis: Found C, 59.9; H, 4.3; N, 9.2; $C_{22}H_{18}ClN_3O_3$ 1HCl requires C, 59.5; H, 4.3; N, 9.5%.

The 4-amino-2-chlorophenyl phenyl ether used as a starting material was obtained as follows:

Sodium hydride (60% dispersion in mineral oil, 0.82 g) was added portionwise to a stirred solution of phenol (1.61 g) in NMP (40 ml) and the mixture was stirred at ambient temperature for 15 minutes. 3-Chloro-4-fluoronitrobenzene (3 g) was added and the mixture was heated to 140° C. for 50 hours. The mixture was cooled to ambient temperature and partitioned between water and ethyl acetate. The organic phase was washed with water and with brine, dried and evaporated. There was thus obtained 2-chloro-4-nitrophenyl phenyl ether (3.5 g).

The material so obtained was reduced using iron powder and hydrochloric acid using an analogous procedure to that described in the last paragraph of the portion of Example 3 which is concerned with the preparation of starting materials. There was thus obtained 4-amino-2-chlorophenyl phenyl ether in 88% yield;

NMR Spectrum: 5.3 (broad s, 2H), 6.55 (m, 1H), 6.9 (m, 5H), 7.3 (m, 2H).

EXAMPLE 8

Using an analogous procedure to that described in Example 1 except that the reaction mixture was heated to reflux for 16 hours, 4-amino-2-chlorophenyl phenyl sulphide was reacted with 4-chloro-6,7-dimethoxyquinazoline hydrochloride to give 4-(3-chloro-4-phenylthioanilino)-6,7-dimethoxyquinazoline hydrochloride salt in 71% yield, m.p. 245°–247° C.;

NMR Spectrum: 3.9 (s, 3H), 3.93 (s, 3H), 7.09 (d, 1H), 7.15–7.45 (m, 6H), 7.54 (m, 1H), 7.98 (d, 1H), 8.28 (s, 1H), 8.78 (s, 1H), 11.43 (s, 1H);

Elemental Analysis: Found C, 56.9; H, 4.0; N, 8.9; $C_{22}H_{18}ClN_3O_2S$ 1HCl 0.25H$_2$O requires C, 56.9; H, 4.2; N, 9.1%.

The 4-amino-2-chlorophenyl phenyl sulphide used as a starting material was obtained as follows:

Sodium hydride (60% dispersion in mineral oil, 0.82 g) was added portionwise to a stirred solution of thiophenol (1.75 ml) in NMP (40 ml) and the mixture was stirred at ambient temperature for 15 minutes. 3-Chloro-4-fluoronitrobenzene (3 g) was added and the mixture was stirred at ambient temperature for 30 hours. Water (150 ml) was added and the precipitate was isolated, washed with water and dried. There was thus obtained 2-chloro-4-nitrophenyl phenyl sulphide (4.5 g).

Hydrogen chloride gas was led during 45 minutes into a stirred mixture of a portion (2 g) of the sulphide so obtained, iron powder (1.5 g) and ethanol (150 ml). The mixture was stirred at ambient temperature for 2 hours. The mixture was evaporated and the residue was partitioned between methylene chloride and dilute aqueous sodium carbonate solution. The organic phase was dried and evaporated. There was thus obtained 4-amino-2-chlorophenyl phenyl sulphide (1.58 g, 89%);

NMR Spectrum: 5.8 (broad s, 2H), 6.57 (m, 1H), 6.8 (d, 1H), 6.99 (d, 2H), 7.14 (t, 1H), 7.27 (m, 3H).

EXAMPLE 9

A solution of potassium peroxymonosulphate (1.1 g) in water (20 ml) was added to a stirred mixture of 4-(3-chloro-4-phenylthioanilino)-6,7-dimethoxyquinazoline hydrochloride salt (0.46 g), concentrated aqueous sulphuric acid (20%, 10 ml) and ethanol (50 ml). The mixture was stirred at ambient temperature for 16 hours. The mixture was neutralised by the addition of potassium carbonate. The bulk of the ethanol was evaporated and the residue was partitioned between water and ethyl acetate. The organic phase was washed with water, dried and evaporated. The solid product was recrystallised from methanol. There was thus obtained 4-(3-chloro-4-phenylsulphonylanilino)-6,7-dimethoxyquinazoline (0.275 g, 60%), m.p. 234°–236° C.;

NMR Spectrum: 3.94 (s, 3H), 3.98 (s, 3H), 7.24 (s, 1H), 7.55 (m, 3H), 7.75 (m, 2H), 7.83 (s, 1H), 7.91 (d, 1H), 8.1 (m, 1H), 8.22 (d, 1H), 8.58 (s, 1H), 9.73 (s, 1H);

Elemental Analysis: Found C, 56.8; H, 4.3; N, 8.8; $C_{22}H_{18}ClN_3O_4S$ 0.5H$_2$O requires C, 56.8; H, 4.1; N, 9.0%.

EXAMPLE 10

Using an analogous procedure to that described in Example 1 except that the reaction mixture was heated to reflux for 16 hours, 4-amino-2-chlorophenyl 1-methylimidazol-2-yl sulphide was reacted with 4-chloro-6,7-dimethoxyquinazoline hydrochloride to give 4-[3-chloro-4-(1-methylimidazol-2-ylthio)anilino]-6,7- dimethoxyquinazoline dihydrochloride salt in 71% yield, m.p. 244°–246° C.;

NMR Spectrum: 3.85 (s, 3H), 4.0 (s, 3H), 4.07 (s, 3H), 7.21 (d, 1H), 7.45 (s, 1H), 7.7 (s, 1H), 7.9 (m, 2H), 8.2 (d, 1H), 8.6 (s, 1H), 8.9 (s, 1H), 11.9 (broad s, 1H);

Elemental Analysis: Found C, 46.5; H, 4.2; N, 13.5; $C_{20}H_{18}ClN_5O_2S$ 2HCl 1H$_2$O requires C, 46.3; H, 4.3; N, 13.5%.

The 4-amino-2-chlorophenyl 1-methylimidazol-2-yl sulphide used as a starting material was obtained as follows:

Using an analogous procedure to that described in the first paragraph of the portion of Example 8 which is concerned with the preparation of starting materials, 3-chloro-4-fluoronitrobenzene was reacted with 1-methyl-2-imidazolethiol to give 2-chloro-4-nitrophenyl 1-methylimidazol-2-yl sulphide in 87% yield.

The material so obtained was reduced using an analogous procedure to that described in the last paragraph of the portion of Example 3 which is concerned with the preparation of starting materials. There was thus obtained 4-amino-2-chlorophenyl 1-methylimidazol-2-yl sulphide in 88% yield.

EXAMPLE 11

Using an analogous procedure to that described in Example 1, 4-amino-2-chlorobenzanilide was reacted with 4-chloro-6,7-dimethoxyquinazoline hydrochloride to give 4-[3-chloro-4-(N-phenylcarbamoyl)anilino]-6,7-dimethoxyquinazoline hydrochloride salt in 71% yield, m.p. >260° C.;

NMR Spectrum: 4.01 (s, 3H), 4.05 (s, 3H), 7.1 (m, 1H), 7.35 (m, 3H), 7.72 (m, 3H), 7.85 (m, 1H), 8.05 (s, 1H), 8.39 (s, 1H), 8.9 (s, 1H), 10.5 (s, 1H), 11.5 (s, 1H).

The 4-amino-2-chlorobenzanilide used as a starting material was obtained as follows:

Aniline (0.995 ml) was added to a solution of 2-chloro-4-nitrobenzoyl chloride and the mixture was stirred and heated to reflux for 16 hours. The mixture was cooled to ambient temperature and the precipitate was isolated, washed with toluene and dried. There was thus obtained 2-chloro-4-nitrobenzanilide (2.64 g, 94%).

Using an analogous procedure to that described in the last paragraph of the portion of Example 1 which is concerned with the preparation of starting materials, the benzanilide so obtained was reduced with stannous chloride to give 4-amino-2-chlorobenzanilide in 13% yield;

NMR Spectrum: 5.72 (s, 2H), 6.54 (s, 1H), 6.64 (d, 1H), 7.04 (m, 1H), 7.28 (m, 3H), 7.66 (d, 2H), 10.0 (s, 1H).

EXAMPLE 12

Using an analogous procedure to that described in Example 1, 4-amino-N-phenylbenzenesulphonamide was reacted with 4-chloro-6,7-dimethoxyquinazoline hydrochloride to give 6,7-dimethoxy-4-[4-(N-phenylsulphamoyl) anilino]quinazoline hydrochloride salt in 95% yield, m.p. 252°–255° C. (decomposes);

NHR Spectrum: 3.9 (s, 3H), 4.0 (s, 3H), 7.0 (m, 1H), 7.2 (m, 4), 7.4 (s, 1H), 7.9 (m, 4H), 8.4 (s, 1H), 8.9 (s, 1H), 10.3 (s, 1H), 11.6 (s, 1H).

EXAMPLE 13

Using an analogous procedure to that described in Example 1, 5-amino-2-tolyl 2-pyridylmethyl ether was reacted with 4-chloro-6,7-dimethoxyquinazoline hydrochloride to give 6,7-dimethoxy-4-[3-methyl-4-(2-pyridylmethoxy)anilino]quinazoline dihydrochloride salt in 60% yield, m.p. 239°–241° C.;

NMR Spectrum: 2.31 (s, 3H), 3.99 (s, 3H), 4.01 (s, 3H), 5.34 (s, 2H), 7.11 (d, 1H), 7.36–7.57 (m, 4H), 7.73 (d, 1H), 8.04 (m, 1H), 8.28 (s, 1H), 8.67 (d, 1H), 8.78 (s, 1H), 11.32 (s, 1H);

Elemental Analysis: Found C, 55.5; H, 5.4; N, 11.0; $C_{23}H_{22}N_4O_3$ 2HCl 1H$_2$O requires C, 56.0; H, 5.3; N, 11.4%.

The 5-amino-2-tolyl 2-pyridylmethyl ether used as a starting material was obtained as follows:

Sodium hydride (60% dispersion in mineral oil, 1.24 g) was added to a solution of 2-pyridylmethanol (2.49 ml) in NMP (100 ml) and the mixture was stirred at ambient temperature for 15 minutes. 2-Fluoro-5-nitrotoluene (4 g) was added and the mixture was heated to 140° C. for 2.5 hours. The mixture was cooled to ambient temperature, poured into water (300 ml) and stirred for 30 minutes. The precipitate was isolated, washed with water and dried. The material so obtained was purified by column chromatography using increasingly polar mixtures of methylene chloride and methanol as eluent. There was thus obtained 5-nitro-2-tolyl 2-pyridylmethyl ether (1.61 g, 26%);

NMR Spectrum: 2.32 (s, 3H), 5.35 (s, 2H), 7.21 (d, 1H), 7.35 (m, 1H), 7.55 (d, 1H), 7.85 (m, 1H), 8.09 (m, 1H), 8.1 (s, 1H), 8.6 (m, 1H).

The material so obtained was reduced using an analogous procedure to that described in the last paragraph of the portion of Example 3 which is concerned with the preparation of starting materials. There was thus obtained 5-amino-2-tolyl 2-pyridylmethyl ether in 97% yield;.

NMR Spectrum: 2.09 (s, 3H), 4.61 (s, 2H), 5.0 (s, 2H), 6.32 (m, 1H), 6.42 (d, 1H), 6.67 (d, 1H), 7.31 (m, 1H), 7.50 (d, 1H), 7.81 (m, 1H), 8.54 (m, 1H).

EXAMPLE 14

Using an analogous procedure to that described in Example 1 except that the reaction mixture was heated to reflux for 6 hours, 4-amino-2-chlorophenyl 3-furylmethyl ether was reacted with 4-chloro-6,7-dimethoxyquinazoline hydrochloride to give 4-[3-chloro-4-(3-furylmethoxy) anilino]-6,7-dimethoxyquinazoline hydrochloride salt in 79% yield, m.p. 244°–246° C.;

NMR Spectrum: 4.0 (s, 3H), 4.04 (s, 3H), 5.12 (s, 2H), 6.58 (d, 1H), 7.33 (s, 1H), 7.37 (d, 1H), 7.65 (m, 1H), 7.68 (m, 1H), 7.82 (m, 2H), 8.28 (s, 1H), 8.82 (s, 1H), 11.32 (s, 1H);

Elemental Analysis: Found C, 55.9; H, 4.2; N, 9.3; $C_{21}H_{18}ClN_3O_4$ 1HCl 0.2H$_2$O requires C, 55.8; H, 4.3; N, 9.3%.

The 4-amino-2-chlorophenyl 3-furylmethyl ether used as a starting material was obtained in 17% yield from 3-chloro-4-fluoronitrobenzene using analogous procedures to those described in the portion of Example 13 which is concerned with the preparation of starting materials. The required material gave the following NMR chemical sheft data: 4.82 (s, 2H), 4.9 (s, 2H), 6.45 (m, 1H), 6.52 (d, 1H), 6.61 (d, 1H), 6.9 (d, 1H), 7.65 (s, 1H), 7.7 (s, 1H).

EXAMPLE 15

Using an analogous procedure to that described in Example 1 except that the reactants were stirred and unless otherwise stated heated to reflux for 16 hours, the appropriate aniline was reacted with 4-chloro-6,7- dimethoxyquinazoline hydrochloride to give the compounds described in Table I.

TABLE I (R²)ₙ—Ar—X—Q, HN, quinazoline with OMe, OMe substituents

Example 15 Compound

| Compound No. | (R²)ₙ | X | Q | Yield (%) | m.p. (°C.) |
|---|---|---|---|---|---|
| 1[a] | 3-chloro | CO | 4-chlorophenyl | 78 | 247–249 |
| 2[b] | 3-chloro | CO | 4-fluorophenyl | 37 | 253–255 |
| 3[c] | 3-chloro | CO | 3-cyanophenyl | 10 | 135–137 |
| 4[d] | 3-chloro | CO | 3-pyridyl | 39 | 185–188 |
| 5[e] | 3-chloro | CO | 2-furyl | 73 | ND |
| 6[f] | 3-chloro | CO | 2-thienyl | 71 | 270–272 |
| 7[g] | 3-chloro | CO | 3-thienyl | 28 | ND |
| 8[h] | 3-chloro | CO | 2-thiazolyl | 72 | ND |
| 9[i] | 3-chloro | CO | 2-imidazolyl | 57 | ND |
| 10[j] | 3-chloro | CH(OH) | 2-pyridyl | 63 | 220–223 |
| 11[k] | 3-chloro | O | 3-chlorophenyl | 52 | 242–244 |
| 12[l] | 3-chloro | O | 2-pyridyl | 81 | 255–260 (decomposes) |
| 13[m] | 3-chloro | S | 2-tolyl | 88 | >250 |
| 14[n] | 3-chloro | S | 2-pyridyl | 64 | 245 (decomposes) |
| 15[o] | 3-chloro | S | 3-methylpyrid-2-yl | 18 | ND |
| 16[p] | 3-chloro | S | 2-imidazolyl | 61 | 230–235 (decomposes) |
| 17[q] | 3-chloro | S | 2-thienyl | 80 | >250 |
| 18[r] | 3-chloro | S | 2-thiazolyl | 85 | 246–248 |
| 19[s] | hydrogen | OCH₂ | phenyl | 49 | 267–269 |
| 20[t] | 2-fluoro | OCH₂ | 2-pyridyl | 37 | 203–205 |
| 21[u] | 3-chloro | OCH₂ | 2-pyridyl | 71 | 237–239 (decomposes) |
| 22[v] | 3-chloro | OCH₂ | 2-furyl | 55 | 237–240 (decomposes) |
| 23[w] | 3-chloro | OCH₂ | 2-thienyl | 49 | 225–227 |
| 24[x] | 3-chloro | OCH₂ | 1-methyl-imidazol-2-yl | 69 | 247–249 (decomposes) |
| 25[y] | 3-chloro | CO | 2-oxazolyl | 86 | >250 |
| 26[z] | 3-chloro | NHSO₂ | phenyl | 51 | >250 |
| 27[aa] | 3-chloro | CONH | 2-pyridyl | 70 | >250 |
| 28[bb] | 3-methyl | OCH₂ | 2-thiazolyl | 63 | 248–250 |
| 29[cc] | 3-methyl | OCH₂ | 1-methyl-imidazol-2-yl | 71 | 238–239 (decomposes) |
| 30[dd] | 3-methyl | OCH₂ | 4-methylpyrid-2-yl | 47 | 231–233 |
| 31[ee] | 3-fluoro | OCH₂ | 2-pyridyl | 15 | 236–238 |
| 32[ff] | 3-methyl | OCH₂ | 4-chloro-pyrid-2-yl | 41 | ND |
| 33[gg] | 3-methyl | OCH₂ | 4-methoxy-pyrid-2-yl | 9 | 179–183 |
| 34[hh] | 3-methyl | OCH₂ | 6-methyl-pyrid-2-yl | 29 | 240–242 |
| 35[ii] | 2,5-difluoro | OCH₂ | 2-pyridyl | 40 | 214–216 |
| 36[jj] | 2-fluoro-3-methyl | OCH₂ | 2-pyridyl | 40 | >240 |
| 37[kk] | 2,3-difluoro | OCH₂ | 2-pyridyl | 21 | 246–248 |

Notes

The numerical location of the (R¹)ₙ group, where present, is indicated relative to the imino (NH) group, for example Compound No. 1 is 4-[3-chloro-4-(4-chlorobenzoyl) anilino]-6,7-dimethoxyquinazoline hydrochloride salt.

The abbreviation ND means 'not determined'.

a. The product was obtained as a hydrochloride salt and gave the following NMR data: 4.03 (s, 3H), 4.06 (s, 3H), 7.36 (s, 1H), 7.68 (m, 3H), 7.78 (m, 1H), 7.98 (m, 1H), 8.17 (d, 1H), 8.28 (s, 1H), 8.93 (s, 1H), 11.23 (s, 1H).

The 4-amino-2,4'-dichlorobenzophenone used as a starting material was obtained from 2-chloro-4-nitrobenzoic acid using an analogous procedure to that described in the portion of Example 1 which is concerned with the preparation of starting materials except that chlorobenzene was used in place of benzene.

b. The reaction mixture was heated to reflux for 4 hours. The product was obtained as a hydrochloride salt and gave the following NMR data: 4.0 (s, 3H), 4.1 (s, 3H), 7.4 (m, 3H), 7.6 (d, 1H), 7.9 (m, 2H), 8.0 (m, 1H), 8.2 (s, 1H), 8.5 (s, 1H), 9.0 (s, 1H), 11.5 (s, 1H).

The 4-amino-2-chloro-4'-fluorobenzophenone used as a starting material was obtained from 2-chloro-4-nitrobenzoic acid using an analogous procedure to that described in the portion of Example 1 which is concerned with the preparation of starting materials except that fluorobenzene was used in place of benzene.

c. The product was purified by column chromatography using a 20:3 mixture of methylene chloride and methanol as eluent. The product gave the following NMR data: 3.95 (s, 3H), 4.05 (s, 3H), 7.3 (s, 1H), 7.6 (d, 1H), 7.8 (t, 1H), 7.9 (s, 1H), 8.05 (m, 2H), 8.2 (m, 2H), 8.6 (s, 1H), 9.8 (s, 1H).

The 4-amino-2-chloro-3'-cyanobenzophenone used as a starting material was obtained from 3-chloro-4-iodonitrobenzene and 3-cyanobenzaldehyde using analogous procedures to those described in the portion of Example 2 which is concerned with the preparation of starting materials.

d. The product was obtained as a dihydrochloride salt, monohydrate and gave the following NMR data: 3.9 (s, 3H), 4.0 (s, 3H), 7.4 (s, 1H), 7.7 (m, 2H), 8.0 (d, 1H), 8.2 (d, 2H), 8.6 (s, 1H), 8.9 (m, 2H), 9.0 (s, 1H), 11.9 (s, 1H).

The 4-amino-2-chlorophenyl 3-pyridyl ketone used as a starting material was obtained from 3-chloro-4-iodonitrobenzene and pyridine-3-carboxaldehyde using analogous procedures to those described in the portion of Example 2 which is concerned with the preparation of starting materials.

e. The reaction mixture was heated to reflux for 3 hours. The product was obtained as a hydrochloride salt and gave the following NMR data: 4.05 (s, 3H), 4.08 (s, 3H), 6.8 (m, 1H), 7.29 (d, 1H), 7.38 (s, 1H), 7.75 (d, 1H), 7.97 (m, 1H), 8.18 (d, 2H), 8.39 (s, 1H), 8.96 (s, 1H), 11.49 (s, 1H).

The 4-amino-2-chlorophenyl 2-furyl ketone used as a starting material was obtained as follows:

n-Butyl lithium (1.6M in hexane, 2.95 ml) was added dropwise to a stirred solution of furan (0.18 ml) in THF (50 ml) which had been cooled to −65° C. and the mixture was stirred at that temperature for 1 hour. A solution of 2-chloro-N-methoxy-N-methyl-4-nitrobenzamide (0.5 g) in THF (20 ml) was added dropwise and the mixture was stirred at −65° C. for 90 minutes. The mixture was allowed to warm to 0° C. A saturated aqueous ammonium chloride solution was added and the mixture was extracted with methylene chloride. The organic phase was washed with water, dried (MgSO$_4$) and evaporated. The residue was purified by column chromatography using a 1:4 mixture of hexane and methylene chloride as eluent. There was thus obtained 2-chloro-4-nitrophenyl 2-furyl ketone (0.5 g).

Hydrogen chloride gas was bubbled into a stirred mixture of 2-chloro-4-nitrophenyl 2-furyl ketone (0.5 g), iron powder (0.6 g) and ethanol (50 ml) which had been cooled to approximately 5° C. until the exothermic reaction ceased. The mixture was stored at 5° C. for 16 hours, basified by the addition of 2M aqueous sodium hydroxide solution and extracted with methylene chloride. The mixture was dried (MgSO$_4$) and evaporated to give 4-amino-2-chlorophenyl 2-furyl ketone (0.1 g);

NMR Spectrum: 6.06 (s, 2H), 6.54 (m, 1H), 6.66 (d, 1H), 6.69 (m, 1H), 7.10 (d, 1H), 7.32 (d, 1H), 8.01 (d, 1H).

f. The reaction mixture was heated to reflux for 3 hours. The product was obtained as a hydrochloride salt and gave the following NMR data: 4.01 (s, 3H), 4.07 (s, 3H), 7.3 (m, 1H), 7.4 (s, 1H), 7.56 (m, 1H), 7.73 (d, 1H), 8.0 (m, 1H), 8.2 (m, 2H), 8.48 (s, 1H), 8.98 (s, 1H), 11.64 (s, 1H).

The 4-amino-2-chlorophenyl 2-thienyl ketone used as a starting material was obtained using analogous procedures to those described in Note e. immediately above except that thiophene was used in place of furan.

g. The product gave the following NMR data: 4.04 (s, 3H), 4.06 (s, 3H), 7.38 (s, 1H), 7.53 (m, 1H), 7.67 (d, 1H), 7.74 (m, 1H), 7.95 (m, 1H), 8.15 (m, 2H), 8.32 (s, 1H), 8.93 (s, 1H), 11.28 (s, 1H).

The 4-amino-2-chlorophenyl 3-thienyl ketone used as a starting material was obtained as follows:

n-Butyl lithium (1.6M in hexane, 3.84 ml) was added dropwise to a solution of 3-bromothiophene (1 g) in hexane (10 ml) which had been cooled to −48° C. THF (1 ml) was added and the mixture was stirred at −48° C. for 15 minutes. Hexane (20 ml) was added and the mixture was stirred and allowed to warm to ambient temperature. A solution of 2-chloro-N-methoxy-N-methyl-4-nitrobenzamide (1.5 g) in THF (2 ml) was added and the mixture was stirred at ambient temperature for 16 hours. The mixture was partitioned between ethyl acetate and water. The organic phase was washed with water, dried (MgSO$_4$) and evaporated. The residue was purified by column chromatography using a 2:1 mixture of hexane and methylene chloride as eluent. There was thus obtained 2-chloro-4-nitrophenyl 3-thienyl ketone (0.13 g).

The material so obtained was reduced using iron powder and hydrochloric acid using an analogous procedure to that described in the last paragraph of the portion of Example 3 which is concerned with the preparation of starting materials. There was thus obtained 4-amino-2-chlorophenyl 3-thienyl ketone in 82% yield;

NMR Spectrum: 6.56 (m, 1H), 6.68 (d, 1H), 7.24 (d, 1H), 7.42 (m, 1H), 7.64 (m, 1H), 8.01 (m, 1H).

h. The reaction mixture was heated to reflux for 3 hours. The product was obtained as a hydrochloride salt containing 0.8 equivalents of water and it gave the following NMR data: 4.14 (s, 3H), 4.18 (s, 3H), 7.59 (s, 1H), 8.0–8.14 (m, 2H), 8.28 (d, 1H), 8.33 (d, 1H), 8.48 (d, 2H), 9.09 (s, 1H), 11.62 (s, 1H).

The 4-amino-2-chlorophenyl 2-thiazolyl ketone used as a starting material was obtained as follows:

Using analogous procedures to those described in Note e. above, 2-chloro-N-methoxy-N-methyl-4-nitrobenzamide was reacted with thiazole and the ketone so obtained was reduced with iron powder and hydrogen chloride gas. Over-reduction occurred and the material obtained was 1-(4-amino-2-chlorophenyl)-1-(2-thiazolyl)methanol.

A mixture of this material (0.3 g), manganese dioxide (0.433 g) and chloroform (50 ml) was stirred at ambient temperature for 16 hours. The mixture was filtered and evaporated. There was thus obtained 4-amino-2-chlorophenyl 2-thiazolyl ketone (0.13 g);

NMR Spectrum: 6.30 (s, 2H), 6.56 (m, 1H), 6.69 (d, 1H), 7.84 (d, 1H), 8.14 (m, 2H).

i. The reaction mixture was heated to reflux for 3 hours. The product was obtained as a hydrochloride salt containing 0.2 equivalents of water. The material gave the following NMR data: 4.02 (s, 3H), 4.03 (s, 3H), 7.4 (s, 1H), 7.45 (s, 2H), 7.88 (m, 2H), 8.08 (d, 1H), 8.34 (s, 1H), 8.94 (s, 1H), 11.4 (s, 1H).

The 4-amino-2-chlorophenyl 2-imidazolyl ketone used as a starting material was obtained as follows:

A mixture of imidazole (12.81 g), triethyl orthoformate (133 ml) and 4-toluenesulphonic acid (1 g) was stirred and heated to 130° C. for 3 hours. The mixture was stored at ambient temperature for 16 hours. The triethyl orthoformate was evaporated and the residue was distilled under vacuum to give imidazole-l-carboxaldehyde diethyl acetal (3.44 g).

n-Butyl lithium (1.6M in hexane, 12.6 ml) was added dropwise to a stirred solution of the diethyl acetal (3.44 g) in THF (100 ml) which had been cooled to −48° C. The mixture was stirred at −48° C. for 30 minutes. A solution of 2-chloro-N-methoxy-N-methyl-4-nitrobenzamide (4.5 g) in THF (10 ml) was added and the mixture was stirred at ambient temperature for 4 hours. The mixture was partitioned between ethyl acetate and 2M aqueous hydrochloric acid. The organic phase was wished with 2M aqueous hydrochloric acid. The aqueous extracts were combined, neutralised by the addition of 2M aqueous sodium hydroxide solution, and extracted with methylene chloride. The organic phase was dried (MgSO$_4$) and evaporated. There was thus obtained 2-chloro-4-nitrophenyl 2-imidazolyl ketone (0.8 g).

A mixture of the material so obtained, iron powder (1.6 g), ferrous sulphate (0.4 g) and water (10 ml) was stirred and heated to reflux for 3 hours. The mixture was cooled to ambient temperature and extracted with ethyl acetate. The organic phase was dried (MgSO$_4$) and evaporated to give 4-amino-2-chlorophenyl 2-imidazolyl ketone (0.46 g);

NMR Spectrum: 6.12 (s, 2H), 6.53 (m, 1H), 6.68 (d, 1H), 7.18 (s, 1H), 7.42 (s, 1H), 7.64 (d, 1H), 13.2 (s, 1H).

j. The reaction mixture was heated to reflux for 2 hours. The product was obtained as a dihydrochloride salt and gave the following NMR data: 3.9 (s, 3H), 4.0 (s, 3H), 6.2 (s, 1H), 7.4 (s, 1H), 7.5–7.8 (m, 3H), 7.9 (d, 1H), 8.1 (t, 1H), 8.3 (s, 1H), 8.6 (d, 1H), 8.9 (s, 1H), 11.7 (s, 1H).

The 1-(4-amino-2-chlorophenyl)-1-(2-pyridyl)methanol used as a starting material was obtained in 68% yield by the reaction of 4-amino-2-chlorophenyl 2-pyridyl ketone, iron powder and hydrogen chloride gas using an analogous procedure to that described in the last paragraph of the portion of Example 2 which is concerned with the preparation of starting materials.

k. The product was obtained as a hydrochloride salt and gave the following NMR data: 4.0 (s, 3H), 4.05 (s, 3H), 6.95 (m, 1H), 7.05 (t, 1H), 7.2 (m, 1H), 7.4 (m, 3H), 7.8 (m, 1H), 8.1 (d, 1H), 8.4 (s, 1H), 8.9 (s, 1H), 11.5 (s, 1H).

The 4-amino-2-chlorophenyl 3-chlorophenyl ether used as a starting material was obtained using analogous procedures to those described in the portion of Example 7 which is concerned with the preparation of starting materials except that 3-chlorophenol was used in place of phenol.

l. The product was obtained as a hydrochloride salt containing 0.5 equivalents of water and gave the following NMR data: 4.01 (s, 3H), 4.04 (s, 3H), 7.15 (m, 2H), 7.35 (s, 1H), 7.41 (d, 1H), 7.76 (m, 1H), 7.91 (m, 1H), 8.01 (d, 1H), 8.14 (m, 1H), 8.37 (s, 1H), 8.89 (s, 1H), 11.48 (broad s, 1H).

The 4-amino-2-chlorophenyl 2-pyridyl ether used as a starting material was obtained using analogous procedures to those described in the portion of Example 7 which is concerned with the preparation of starting materials except that 2-hydroxypyridine was used in place of phenol.

m. The reaction mixture was heated to reflux for 3 hours. The product was obtained as a hydrochloride salt and gave the following
NMR data: 2.37 (s, 3H), 4.0 (s, 3H), 4.02 (s, 3H), 6.4 (d, 1H), 7.3 (m, 5H), 7.45 (m, 1H), 7.67 (m, 1H), 8.03 (d, 1H), 8.29 (s, 1H), 8.88 (s, 1H), 11.32 (s, 1H).

The 4-amino-2-chlorophenyl 2-tolyl sulphide used as a starting material was obtained as follows:

Using an analogous procedure to that described in the first paragraph of the portion of Example 8 which is concerned with the preparation of starting materials, 3-chloro-4-fluoronitrobenzene was reacted with 2-toluenethiol. The reaction mixture was partitioned between ethyl acetate and water. The organic phase was dried (MgSO$_4$) and evaporated to give 2-chloro-4-nitrophenyl 2-tolyl sulphide in 31% yield.

The material so obtained was reduced using an analogous procedure to that described in the last paragraph of the portion of Example 3 which is concerned with the preparation of starting materials. There was thus obtained 4-amino-2-chlorophenyl 2-tolyl sulphide in 18% yield.

n. The product was obtained as a dihydrochloride salt and gave the following NMR data: 4.01 (s, 3H), 4.06 (s, 3H), 7.09 (d, 1H), 7.20 (m, 1H), 7.43 (s, 1H), 7.51 (m, 1H), 7.79 (d, 1H), 7.94 (m, 1H), 8.24 (d, 1H), 8.43 (m, 1H), 8.57 (s, 1H), 8.96 (s, 1H), 11.84 (s, 1H).

The 4-amino-2-chlorophenyl 2-pyridyl sulphide used as a starting material was obtained using analogous procedures to those described in the portion of Example 8 which is concerned with the preparation of starting materials except that 2-pyridinethiol was used in place of thiophenol.

o. The reaction mixture was heated to reflux for 3 hours. The product was-obtained as a hydrochloride salt containing 0.2 equivalents of water. The product gave the following NMR data: 2.37 (s, 3H), 4.0 (s, 3H), 4.05 (s, 3H), 7.15 (m, 1H), 7.37 (s, 1H), 7.64 (m, 1H), 7.67 (d, 1H), 7.83 (m, 1H), 8.12 (d, 1H), 8.18 (m, 1H), 8.36 (s, 1H), 8.93 (s, 1H), 11.43 (s, 1H).

The 4-amino-2-chlorophenyl 3-methylpyrid-2-yl sulphide used as a starting material was obtained as follows:

A mixture of 2-hydroxy-3-methylpyridine (2 g), phosphorus pentasulphide (8.97 g) and pyridine (60 ml) was stirred and heated to reflux for 4 hours. The mixture was poured into water and extracted with ethyl acetate. The organic phase was washed with water, dried (MgSO$_4$) and evaporated to give 3-methyl-2-pyridinethiol (0.87 g).

Using an analogous procedure to that described in the first paragraph of the portion of Example 8 which is concerned with the preparation of starting materials, 3-chloro-4-fluoronitrobenzene was reacted with 3-methyl-2-pyridinethiol to give 2-chloro-4-nitrophenyl 3-methylpyrid-2-yl sulphide in 50% yield.

The material so obtained was reduced using an analogous procedure to that described in the last paragraph of the portion of Example 3 which is concerned with the preparation of starting materials. There was thus obtained 4-amino-2-chlorophenyl 3-methylpyrid-2-yl sulphide in 31% yield.

p. The product was obtained as a dihydrochloride salt containing one equivalent of water. The product gave the following NMR data: 4.0 (s, 3H), 4.04 (s, 3H), 7.28 (d, 1H), 7.42 (s, 1H), 7.72 (s, 2H), 7.89 (m, 1H), 8.17 (d, 1H), 8.56 (s, 1H), 8.89 (s, 1H), 11.85 (broad s, 1H).

The 4-amino-2-chlorophenyl 2-imidazolyl sulphide used as a starting material was obtained as follows:

Using an analogous procedure to that described in the first paragraph of the portion of Example 8 which is concerned with the preparation of starting materials, 3-chloro-4-fluoronitrobenzene was reacted with 2-imidazolethiol to give a precipitated solid which was partitioned between methylene chloride and 2 h aqueous sodium hydroxide solution. The aqueous phase was acidified by the addition of a concentrated (20%) aqueous citric acid solution and the precipitate was isolated and dried. The material was recrystallised from a mixture of hexane and ethyl acetate to give 2-chloro-4-nitrophenyl 2-imidazolyl sulphide in 13% yield.

The material so obtained was reduced using an analogous procedure to that described in the last paragraph of the portion of Example 3 which is concerned with the preparation of starting materials except that a saturated aqueous sodium bicarbonate solution was used in place of 2M aqueous sodium hydroxide solution to basify the reaction mixture. There was thus obtained 4-amino-2-chlorophenyl 2-imidazolyl sulphide in 48% yield.

q. The reaction mixture was heated to reflux for 3 hours. The product was obtained as a hydrochloride salt and gave the following NMR data: 3.98 (s, 3H), 4.0 (s, 3H), 6.93 (d, 1H), 7.28 (m, 1H), 7.35 (s, 1H), 7.56 (m, 1H), 7.68 (m, 1H), 7.95 (m, 1H), 7.99 (d, 1H), 8.32 (s, 1H), 8.84 (s, 1H), 11.45 (s, 1H).

The 4-amino-2-chlorophenyl 2-thienyl sulphide used as a starting material was obtained as follows:

Using an analogous procedure to that described in the first paragraph of the portion of Example 8 which is concerned with the preparation of starting materials, 3-chloro-4-fluoronitrobenzene was reacted with 2-thiophenethiol to give 2-chloro-4-nitrophenyl 2-thienyl sulphide in 32% yield.

The material so obtained was reduced using an analogous procedure to that described in the last paragraph of the portion of Example 3 which is concerned with the preparation of starting materials to give 4-amino-2-chlorophenyl 2-thienyl sulphide in 27% yield.

r. The reaction mixture was heated to reflux for 3 hours. The product was obtained as a hydrochloride salt and gave the following NMR data: 4.04 (s, 3H), 4.08 (s, 3H), 7.38 (s, 1H), 7.76 (d, 1H), 7.78 (s, 1H), 7.85 (d, 1H), 7.94 (m, 1H), 8.27 (d, 1H), 8.38 (s, 1H), 8.94 (s, 1H), 11.44 (s, 1H).

The 4-amino-2-chlorophenyl 2-thiazolyl sulphide used as a starting material was obtained as follows:

Using an analogous procedure to that described in the first paragraph of the portion of Example 8 which is concerned with the preparation of starting materials, 3-chloro-4-fluoronitrobenzene was reacted with 2-thiazolethiol to give a precipitated solid which was partitioned between ethyl acetate and water. The organic phase was dried (MgSO$_4$) and evaporated to give 2-chloro-4-nitrophenyl 2-thiazolyl sulphide in 26% yield.

The material so obtained was reduced using an analogous procedure to that described in the last paragraph of the portion of Example 3 which is concerned with the preparation of starting materials. There was thus obtained 4-amino-2-chlorophenyl 2-thiazolyl sulphide in 51% yield.

s. The product was obtained as a hydrochloride salt and gave the following NMR data: 4.0 (s, 3H), 4.02 (s, 3H), 5.18 (s, 2H), 7.14 (d, 1H), 7.3 (s, 11), 7.48 (m, 2H), 8.2 (s, 1H), 8.75 (s, 1H), 11.15 (s, 1H).

The 4-benzyloxyaniline used as a starting material was obtained from 4-fluoronitrobenzene and benzyl alcohol using analogous procedures to those described in the portion of Example 13 which is concerned with the preparation of starting materials.

t. The reaction mixture was heated to reflux for 3 hours. The precipitate was dissolved in water and the solution was washed with ethyl acetate. The aqueous solution was basified by the addition of 2M aqueous sodium hydroxide solution and extracted with ethyl acetate. The organic phase was dried ($MgSO_4$) and evaporated. The residue was purified by column chromatography using increasingly polar mixtures of methylene chloride and methanol as eluent. The product so obtained contained 0.5 equivalents of water.

The 4-amino-3-fluorophenyl 2-pyridylmethyl ether used as a starting material was obtained as follows:

A mixture of 3-fluoro-4-nitrophenol (3.14 g), 2-pyridylmethyl chloride (3.28 g), potassium carbonate (5.52 g) and DMF (20 ml) was stirred at ambient temperature for 16 hours. The mixture was partitioned between ethyl acetate and water. The organic phase was washed with water, dried ($MgSO_4$) and evaporated. The residue was purified by column chromatography using increasingly polar mixtures of hexane and ethyl acetate to give 3-fluoro-4-nitrophenyl 2-pyridylmethyl ether (0.86 g).

A mixture of the material so obtained, ethyl acetate (25 ml) and 10% palladium-on-carbon catalyst (0.08 g) was stirred under an atmosphere of hydrogen gas for 5 hours. The mixture was filtered and evaporated. The residue was purified by column chromatography using increasingly polar mixtures of hexane and ethyl acetate as eluent. There was thus obtained 4-amino-3-fluorophenyl 2-pyridylmethyl ether (0.32 g);

NMR Spectrum: 4.6 (broad s, 2H), 5.0 (s, 2H), 6.7 (m, 3H), 7.3 (m, 1H), 7.5 (d, 1H), 7.8 (m, 1H), 8.6 (d, 1H).

u. The reaction mixture was heated to reflux for 5 hours. The product was obtained as a dihydrochloride salt containing one equivalent of water. The product gave the following NMR data: 4.0 (s, 3H), 4.04 (s, 3H), 5.42 (s, 2H), 7.37 (d, 1H), 7.40 (s, 1H), 7.56 (m, 1H), 7.69 (m, 1H), 7.75 (d, 1H), 7.93 (d, 1H), 8.09 (m, 1H), 8.45 (s, 1H), 8.71 (d, 1H), 8.84 (s, 1H), 11.64 (broad s, 1H).

The 4-amino-2-chlorophenyl 2-pyridylmethyl ether used as a starting material was obtained as follows:

2-Pyridinemethanol (3.7 ml) was added to a stirred suspension of sodium hydride (80% dispersion in mineral oil, 1.38 g) in NHP (70 ml) and the mixture was stirred at ambient temperature for 15 minutes. 3-Chloro-4-fluoronitrobenzene (6.73 g) was added portionwise and the mixture was stirred at ambient temperature for 20 hours. Water (175 ml) was added and the precipitate was isolated, washed with water and with hexane and dried. There was thus obtained 2-chloro-4-nitrophenyl 2-pyridylmethyl ether (8.06 g), m.p. 141°–144° C.

A mixture of a portion (2.95 g) of the material so obtained, 5% platinum-on-carbon catalyst (0.15 g) and ethanol (200 ml) was stirred under an atmosphere of hydrogen for 5 hours. The mixture was filtered and the filtrate was evaporated to give 4-amino-2-chlorophenyl 2-pyridylmethyl ether (2.48 g) which was used without further purification.

v. The reaction mixture was heated to reflux for 3 hours. The product was obtained as a hydrochloride salt containing 0.25 equivalents of water and gave the following NMR data: 4.0 (s, 3H), 4.01 (s, 3H), 5.21 (s, 2H), 6.49 (m, 1H), 6.65 (d, 1H), 7.34 (s, 1H), 7.41 (d, 1H), 7.65 (m, 1H), 7.72 (d, 1H), 7.83 (d, 1H), 8.29 (s, 1H), 8.83 (s, 1H), 11.33 (broad s, 1H).

The 4-amino-2-chlorophenyl furfuryl ether used as a starting material was obtained using analogous procedures to those described in Note u. immediately above except that 2-furylmethanol was used in place of 2-pyridinemethanol.

w. The reaction mixture was heated to reflux for 3 hours. The product was obtained as a hydrochloride salt containing 0.2 equivalents of water and gave the following NMR data: 4.03 (s, 3H), 4.05 (s, 3H), 5.48 (s, 2H), 7.08 (m, 1H), 7.15 (s, 1H), 7.28 (d, 1H), 7.43 (d, 1H), 7.62 (m, 2H), 7.84 (d, 1H), 8.26 (s, 1H), 8.85 (s, 1H), 11.3 (broad s, 1H).

The 4-amino-2-chlorophenyl 2-thienylmethyl ether used as a starting material was obtained as follows:

Using an analogous procedure to that described in the first paragraph of the portion of Example 8 which is concerned with the preparation of starting materials, 3-chloro-4-fluoronitrobenzene was reacted with 2-thienylmethanol to give 2-chloro-4-nitrophenyl 2-thienylmethyl ether in 40% yield.

The material so obtained was reduced using an analogous procedure to that described in the last paragraph of the portion of Example 3 which is concerned with the preparation of starting materials. There was thus obtained 4-amino-2-chlorophenyl 2-thienylmethyl ether in 38% yield.

x. The mixture was heated to reflux for 5 hours. The product was obtained as a dihydrochloride salt containing one equivalent of water. The product gave the following NMR data: 3.95 (s, 3H), 4.0 (s, 3H), 4.04 (s, 3H), 5.62 (s, 2H), 7.42 (s, 1H), 7.52 (d, 1H), 7.69 (m, 1H), 7.78 (m, 2H), 7.95 (d, 1H), 8.52 (s, 1H), 8.82 (s, 1H), 11.72 (broad s, 1H).

The 4-amino-2-chlorophenyl 1-methylimidazol-2-ylmethyl ether used as a starting material was obtained using analogous procedures to those described in Note u. above except that 1-methylimidazol-2-ylmethanol was used in place of 2-pyridinemethanol.

y. The product gave the following NMR data: 4.02 (s, 3H), 4.06 (s, 3H), 7.77 (d, 1H), 7.90 (s, 1H), 7.98 (m, 1H), 8.16 (s, 1H), 8.43 (s, 1H), 8.62 (s, 1H), 8.94 (d, 1H), 11.61 (s, 1H).

The 4-amino-2-chlorophenyl 2-oxazolyl ketone used as a starting material was obtained as follows:

Di-isobutylaluminium hydride (1.5M in toluene, 16.34 ml) was added to a stirred solution of 2-chloro-N-methoxy-N-methyl-4-nitrobenzamide (5 g) in toluene (100 ml) which had been cooled to −78° C. The mixture was stirred for 40 minutes. Methanol (10 ml) was added and the solvent was evaporated. The residue was partitioned between ethyl acetate and 2M aqueous hydrochloric acid. The organic solution was washed with water, dried ($MgSO_4$) and evaporated to give 2-chloro-4-nitrobenzaldehyde (2 g).

n-Butyl lithium (1.6M in hexane, 7.4 ml) was added to a solution of oxazole (0.78 ml) in THF (100 ml) which had been cooled to −70° C. The mixture was stirred at that temperature for 1 hour. A solution of 2-chloro-4-nitrobenzaldehyde (2 g) in THF (5 ml) was added and the mixture was stirred at −70° C. for 3 hours. A saturated aqueous ammonium chloride solution was added and the mixture was extracted with ethyl acetate. The organic phase was dried ($MgSO_4$) and evaporated to give 1-(2-chloro-4-nitrophenyl)-1-(2-oxazolyl)methanol (1.45 g), m.p. 158°–160° C.

The material so obtained was oxidised with manganese dioxide using an analogous procedure to that described in Note h. above to give 2-chloro-4-nitrophenyl 2-oxazolyl ketone in 68% yield, m.p. 124°–125° C.

A mixture of the material so obtained (0.87 g), iron powder (1.74 g), ferrous sulphate (0.46 g) and water (100 ml) was stirred and heated to reflux for 3 hours. The mixture was cooled to ambient temperature and extracted with ethyl acetate. The organic phase was dried (MgSO$_4$) and evaporated to give 4-amino-2-chlorophenyl 2-oxazolyl ketone (0.46 g), m.p. 92°–94° C.; NMR Spectrum: 6.18 (s, 2H), 6.54 (m, 1H), 6.68 (d, 1H), 7.43 (d, 1H), 8.52 (s, 1H), 8.69 (s, 1H).

z. The product was obtained as a hydrochloride salt containing 0.25 equivalents of water and gave the following NMR data: 4.0 (s, 3H), 4.01 (s, 3H), 7.34 (d, 1H), 7.37 (s, 1H), 7.5–7.95 (m, 7H), 8.33 (s, 1H), 8.87 (s, 1H), 10.08 (s, 1H), 11.39 (s, 1H).

The N-(4-amino-2-chlorphenyl)benzenesulphonamide used as a starting material was obtained as follows:

A mixture of 2-chloro-4-nitroaniline (4.33 g), benzenesulphonyl chloride (3.25 ml) and pyridine (2.5 ml) was stirred and heated to 100° C. for 18 hours. The mixture was cooled to ambient temperature and partitioned between methylene chloride and 2M aqueous hydrochloric acid. The organic phase was washed with water, dried and evaporated. The residue was recrystallised from ethyl acetate to give N-(2-chloro-4-nitrophenyl)benzenesulphonamide (6.07 g), m.p. 155°–157° C.

A portion (2 g) of the material so obtained was reduced using an analogous procedure to that described in Example 32 to give N-(4-amino-2-chlorophenyl)benzenesulphonamide in 75% yield.

aa. The product was obtained as a hydrochloride salt and gave the following NMR data: 4.03 (s, 3H), 4.08 (s, 3H), 7.21 (m, 1H), 7.4 (s, 1H), 7.72 (d, 1H), 7.89 (m, 1H), 7.91 (m, 1H), 8.08 (d, 1H), 8.20 (d, 1H), 8.39 (m, 1H), 8.42 (s, 1H), 8.95 (s, 1H), 11.08 (s, 1H), 11.56 (s, 1H).

The 4-amino-2-chloro-N-(2-pyridyl)benzamide used as a starting material was obtained as follows:

A mixture of 2-chloro-4-nitrobenzoyl chloride (3 g), 2-aminopyridine (1.4 g) and toluene (200 ml) was stirred and heated to reflux for 16 hours. The mixture was evaporated and the residue was purified by column chromatography using increasingly polar mixtures of methylene chloride and methanol as eluent. There was thus obtained 2-chloro-4-nitro-N-(2-pyridyl)benzamide (0.8 g), m.p. 168°–170° C.

The material so obtained was reduced using an analogous procedure to that described in Example 32 to give 4-amino-2-chloro-N-(2-pyridyl)benzamide in 67% yield.

bb. The product was obtained as a hydrochloride salt containing 0.2 equivalents of water and gave the following NMR data: 2.3 (s, 3H), 4.0 (s, 3H), 4.02 (s, 3H), 5.53 (s, 2H), 7.19 (d, 1H), 7.38 (s, 1H), 7.46 (d, 1H), 7.48 (s, 1H), 7.80 (d, 1H), 7.87 (d, 1H), 8.31 (s, 1H), 8.8 (s, 1H), 11.34 (s, 1H).

The 5-amino-2-tolyl 2-thiazolylmethyl ether used as a starting material was obtained as follows:

A solution of thiazole (5 g) in diethyl ether (50 ml) was added dropwise to n-butyl lithium (1.6M in hexane, 30 ml) which had been cooled to −70° C. and the mixture was stirred at −70° C. for 3 hours. Formaldehyde gas [obtained by heating paraformaldehyde (5.05 g) to 140° C.] was led into the reaction mixture and the resultant mixture was allowed to warm to ambient temperature and was stirred for 16 hours. The mixture was partitioned between diethyl ether and 4M aqueous hydrochloric acid. The aqueous layer was basified by adding aqueous potassium hydroxide solution and extracted with a mixture of ethyl acetate (80 ml), chloroform (20 ml) and ethanol (20 ml). The extract was evaporated to give 2-thiazolylmethanol (.4.4 g), m.p. 46°–47° C.;

A mixture of a portion (3.1 g) of the material so obtained, sodium hydride (60% dispersion in mineral oil, 1.29 g) and NMP (100 ml) was stirred at ambient temperature for 30 minutes. 2-Fluoro-5-nitrotoluene (4.18 g) was added and the mixture was stirred at ambient temperature for 16 hours. The mixture was partitioned between ethyl acetate and water. The organic phase was washed with water, dried (MgSO$_4$) and evaporated to give 5-nitro-2-tolyl 2-thiazolylmethyl ether (3.3 g), m.p. 151°–153° C.

A portion (1.5 g) of the material so obtained was reduced with iron powder and hydrochloric acid using an analogous procedure to that described in the last paragraph of the portion of Example 3 which is concerned with the preparation of starting materials. There was thus obtained 5-amino-2-tolyl 2-thiazolylmethyl ether in 98% yield;

NMR Spectrum: 2.12 (s, 3H), 4.66 (s, 2H), 5.23 (s, 2H), 6.32–6.44 (m, 2H), 6.76 (d, 1H), 7.73 (d, 1H), 7.80 (d, 1H).

cc. The product was obtained as a dihydrochloride salt, monohydrate and gave the following NMR data: 2.36 (s, 3H), 3.9 (s, 3H), 4.0 (s, 3H), 4.02 (s, 3H), 5.54 (s, 2H), 7.29 (d, 1H), 7.4 (s, 1H), 7.51 (s, 1H), 7.54 (d, 1H), 7.7 (d, 1H), 7.78 (d, 1H), 8.39 (s, 1H), 8.78 (s, 1H), 11.45 (s, 1H).

The 5-amino-2-tolyl 1-methylimidazol-2-ylmethyl ether used as a starting material was obtained using analogous procedures to those described in Note u. above except that 1-methylimidazol-2-ylmethanol was used in place of 2-pyridinemethanol and 2-fluoro-5-nitrotoluene was used in place of 3-chloro-4-fluoronitrobenzene.

dd. The product was obtained as a dihydrochloride salt, monohydrate and gave the following NMR data: 2.3 (s, 3H), 2.6 (s, 3H), 3.97 (s, 3H), 4.03 (s, 3H), 7.1–7.13 (d, 1H), 7.43 (s, 1H), 7.48 (m, 1H), 7.5 (s, 1H), 7.71 (d, 1H), 7.86 (s, 1H), 8.45 (s, 1H), 8.72 (d, 1H), 8.78 (s, 1H), 11.56 (s, 1H).

The 5-amino-2-tolyl 4-methylpyrid-2-ylmethyl ether used as a starting material was obtained using analogous procedures to those described in Note u. above except that 4-methylpyrid-2-ylmethanol was used in place of 2-pyridinemethanol and 2-fluoro-5-nitrotoluene was used in place of 3-chloro-4-fluoronitrobenzene.

ee. The product was obtained as a dihydrochloride salt containing 1.5 equivalents of water and gave the following NMR data: 3.9 (s, 3H), 4.0 (s, 3H), 5.42 (s, 2H), 7.35 (t, 1H), 7.4 (s, 1H), 7.54 (m, 1H), 7.59 (t, 1H), 7.76 (m, 2H), 8.11 (t, 1H), 8.47 (s, 1H), 8.71 (d, 1H), 8.82 (s, 1H), 11.68 (s, 1H).

The 4-amino-2-fluorophenyl 2-pyridylmethyl ether used as a starting material was obtained using analogous procedures to those described in Note u. above except that 3,4-difluoronitrobenzene was used in place of 3-chloro-4-fluoronitrobenzene. The material so obtained was purified by column chromatography using ethyl acetate as eluent. There was thus obtained the required starting material in 52% overall yield which gave the following NMR data: 4.9 (broad s, 2H), 5.05 (s, 2H), 6.25 (m, 1H), 6.42 (m, 1H), 6.87 (t, 1H), 7.33 (m, 1H), 7.51 (d, 1H), 7.84 (m, 1H), 8.55 (m, 1H).

ff. The product was obtained as a dihydrochloride salt and gave the following NMR data: 2.3 (s, 3H), 3.98 (s, 3H), 4.02 (s, 3H), 5.27 (s, 2H), 7.1 (d, 1H), 7.34 (s, 1H), 7.44 (m, 1H), 7.48 (s, 1H), 7.54 (m, 1H), 7.64 (d, 1H), 8.26 (s, 1H), 8.59 (d, 1H), 8.8 (s, 1H), 11.28 (s, 1H).

The 5-amino-2-tolyl 4-chloropyrid-2-ylmethyl ether used as a starting material was obtained using analogous procedures to those described in Note u. above except that 4-chloropyrid-2-ylmethanol was used in place of 2-pyridinemethanol and 2-fluoro-5-nitrotoluene was used in place of 3-chloro-4-fluoronitrobenzene.

gg. The product was obtained as a hydrochloride salt, monohydrate and gave the following NMR data: 2.3 (s, 3H), 3.85 (s, 3H), 3.93 (s, 3H), 3.96 (s, 3H), 5.15 (s, 2H), 6.95 (m, 1H), 7.02 (d, 1H), 7.1 (d, 1H), 7.15 (s, 1H), 7.5 (s, 1H), 7.52 (m, 1H), 7.83 (s, 1H), 8.38 (s, 1H), 8.42 (d, 1H), 9.35 (s, 1H).

The 5-amino-2-tolyl 4-methoxypyrid-2-ylmethyl ether used as a starting material was obtained as follows:

A mixture of methyl 4-chloropyridine-2-carboxylate (3.7 g), sodium metal (0.5 g) and methanol (100 ml) was stirred and heated to reflux for 8 hours. The mixture was evaporated and the residue was partitioned between ethyl acetate and water. The organic phase was dried ($MgSO_4$) and evaporated to give methyl 4-methoxypyridine-2-carboxylate (3 g).

A solution of lithium aluminium hydride (1M in diethyl ether, 16 ml) was added dropwise to a stirred mixture of methyl 4-methoxypyridine-2-carboxylate (2.7 g) and diethyl ether (50 ml). The resultant mixture was heated to reflux for 1 hour. The mixture was treated with potassium sodium tartrate tetrahydrate and extracted with ethyl acetate. The organic phase was dried ($MgSO_4$) and evaporated. The residue was purified by column chromatography using increasingly polar mixtures of methylene chloride and methanol as eluent to give 4-methoxypyrid-2-ylmethanol (0.8 g);

NMR Spectrum: 3.62 (s, 3H), 4.51 (d, 2H), 5,34 (broad t, 1H), 6.8 (m, 1H), 6.99 (d, 1H), 8.27 (d, 1H).

The material so obtained was coupled to 2-fluoro-5-nitrotoluene and the resultant product was reduced using analogous procedures to those described in Note u. above. There was thus obtained 5-amino-2-tolyl 4-methoxypyrid-2-ylmethyl ether in 62% yield which gave the following NMR data: 2.18 (s, 3H), 3.85 (s, 3H), 4.5 (broad s, 2H), 4.85 (s, 2H), 6.34 (m, 1H), 6.43 (d, 1H), 6.68 (d, 1H), 6.9 (m, 1H), 7.05 (d, 1H), 8.36 (d, 1H).

hh. The product was obtained as a dihydrochloride salt, monohydrate and gave the following NMR data: 2.3 (s, 3H), 2.72 (s, 3H), 3.97 (s, 3H), 4.03 (s, 3H), 5.46 (s, 2H), 7.11 (d, 1H), 7.41 (s, 1H), 7.49 (m, 1H), 7.51 (s, 1H), 7.69 (d, 1H), 7.79 (d, 1H), 8.26 (t, 1H), 8.42 (s, 1H), 8.77 (s, 1H), 11.57 (s, 1H).

The 5-amino-2-tolyl 6-methylpyrid-2-ylmethyl ether used as a starting material was obtained using analogous procedures to those described in Note u. above except that 6-methylpyrid-2-ylmethanol (*Chem. Pharm. Bull.*, 1955, 3, 415) was used in place of 2-pyridinemethanol and 2-fluoro-5-nitrotoluene was used in place of 3-chloro-4-fluoronitrobenzene.

ii. The product was obtained as a dihydrochloride salt, monohydrate and gave the following NMR data: 3.98 (s, 6H), 5.41 (s, 2H), 7.4 (s, 1H), 7.45–7.62 (m, 3H), 7.71 (d, 1H), 8.04 (m, 1H), 8.34 (s, 1H), 8.71 (m, 1H), 8.82 (s, 1H), 11.58 (s, 1H).

The 4-amino-2,5-difluorophenyl 2-pyridylmethyl ether used as a starting material was obtained using analogous procedures to those described in Note u. above except that 2,4,5-trifluoronitrobenzene was used in place of 3-chloro-4-fluoronitrobenzene.

jj. The product was obtained as a dihydrochloride salt, monohydrate and gave the following NMR data: 2.24 (s, 3H), 3.98 (s, 6H), 5.36 (s, 2H), 7.01 (d, 1H), 7.31 (t, 1H), 7.4 (s, 1H), 7.53 (t, 1H), 7.74 (d, 1H), 8.06 (m, 1H), 8.3 (s, 1H), 8.69 (d, 1H), 8.76 (s, 1H), 11.47 (s, 1H).

The 5-amino-6-fluoro-2-tolyl 2-pyridylmethyl ether used as a starting material was obtained using analogous procedures to those described in Note u. above except that 2,6-difluoro-3-nitrotoluene was used in place of 3-chloro-4-fluoronitrobenzene.

kk. The product was obtained as a dihydrochloride salt, dihydrate and gave the following NMR data: 4.03 (s, 6H), 5.42 (s, 2H), 7.2–7.35 (m, 2H), 7.4 (s, 1H), 7.52 (t, 1H), 7.7 (d, 1H), 8.03 (m, 1H), 8.35 (s, 1H), 8.68 (d, 1H), 8.8 (s, 1H), 11.73 (s, 1H).

The 4-amino-2,3-difluorophenyl 2-pyridylmethyl ether used as a starting material was obtained using analogous procedures to those described in Note u. above except that 2,3,4-trifluoronitrobenzene was used in place of 3-chloro-4-fluoronitrobenzene.

EXAMPLE 16

Using an analogous procedure to that described in Example 4, the appropriate ketone was reduced with sodium borohydride to give the compounds described in Table II.

TABLE II

| Example 16 Compound No. | Q | Yield (%) | m.p. (°C.) |
|---|---|---|---|
| 1[a] | 4-chlorophenyl | 48 | 195–199 (decomposes) |
| 2[b] | 3-pyridyl | 15 | 238–241 |
| 3[c] | 2-furyl | 39 | 228–230 |
| 4[d] | 2-thienyl | 12 | 229–231 |
| 5[e] | 2-thiazolyl | 90 | foam |
| 6[f] | 2-imidazolyl | 75 | >250 |
| 7[g] | 2-oxazolyl | 31 | 252–254 |

Notes a. The product was recrystallised from a mixture of hexane and ethyl acetate. It contained one equivalent of acetic acid and gave the following NMR data: 1.9 (s, 3H), 3.95 (s, 3H), 4.0 (s, 3H), 6.0 (d, 1H), 6.1 (d, 1H), 7.2 (s, 1H), 7.4 (s, 4H), 7.6 (m, 1H), 7.8 (m, 2H), 8.0 (d, 1H), 8.5 (s, 1H), 9.5 (s, 1H), 11.9 (s, 1H).

b. The product contained 0.5 equivalents of acetic acid and gave the following NMR data: 3.9 (s, 3H), 4.0 (s, 3H), 6.0 (d, 1H), 6.2 (d, 1H), 7.25 (s, 1H), 7.35 (m, 1H), 7.7 (d, 2H), 7.8 (m, 2H), 8.0 (d, 1H), 8.4 (d, 1H), 8.5 (s, 1H), 8.6 (s, 1H), 9.5 (s, 1H).

c. The product contained 0.6 equivalents of water and gave the following NMR data: 3.95 (s, 3H), 3.98 (s, 3H), 5.95 (d, 1H), 6.10 (m, 2H), 6.38 (m, 1H), 7.21 (s, 1H), 7.57 (d, 1H), 7.67 (d, 1H), 7.82 (s, 1H), 7.86 (m, 1H), 8.02 (d, 1H), 8.53 (s, 1H), 9.54 (s, 1H).

d. The product contained 0.6 equivalents of water and gave the following NMR data: 3.95 (s, 3H), 3.98 (s, 3H), 6.22 (d, 1H), 6.32 (d, 1H), 6.92 (m, 2H), 7.22 (s, 1H), 7.43 (m, 1H), 7.68 (d, 1H), 7.83 (s, 1H), 7.86 (m, 1H), 8.03 (d, 1H), 8.52 (s, 1H), 9.53 (s, 1H).

e. The product gave the following NMR data: 3.68 (s, 3H), 3.72 (s, 3H), 6.0 (d, 1H), 6.25 (d, 1H), 6.56 (d, 1H), 6.95 (s, 1H), 7.44 (m, 2H), 7.55 (m, 2H), 7.78 (s, 1H), 8.25 (s, 1H), 9.28 (s, 1H).

f. The product contained 1.2 equivalents of water and gave the following NMR data: 3.94 (s, 3H), 3.99 (s, 3H), 6.05 (d, 1H), 6.17 (d, 1H), 6.94 (s, 2H), 7.24 (s, 1H), 7.64 (d, 1H), 7.82 (m, 1H), 7.84 (s, 1H), 8.0 (d, 1H), 8.53 (s, 1H), 9.54 (s, 1H), 11.98 (s, 1H).

g. The product gave the following NMR data: 3.93 (s, 3H), 3.97 (s, 3H), 5.97 (m, 2H), 7.21 (s, 1H), 7.59 (d, 1H), 7.78–7.88 (m, 3H), 8.01 (d, 1H), 8.28 (s, 1H), 8.51 (s, 1H), 9.52 (s, 1H).

EXAMPLE 17

A mixture of 7-acetoxy-4-(4-benzoyl-3-chloroanilino)-6-methoxyquinazoline (0.75 g), a saturated aqueous ammonium hydroxide solution (16 ml) and methanol (25 ml) was stirred at ambient temperature for 30 minutes. The mixture was evaporated and the residue was triturated under water. There was thus obtained 4-(4-benzoyl-3-chloroanilino)-7-hydroxy-6-methoxyquinazoline (0.58 g, 68%), m.p. 155°–157° C.;

NMR Spectrum: 4.0 (s, 3H), 7.14 (s, 1H), 7.58 (m, 3H), 7.75 (m, 3H), 7.87 (s, 1H), 8.04 (m, 1H), 8.26 (d, 1H), 8.56 (s, 1H), 9.74 (s, 1H), 10.47 (s, 1H).

The 7-acetoxy-4-(4-benzoyl-3-chloroanilino)-6-methoxyquinazoline used as a starting material was obtained as follows.

A mixture of 2-amino-4-benzyloxy-5-methoxybenzamide (*J. Med. Chem,* 1977, 20, 146; 3.65 g), (3-dimethylamino-2-azaprop-2-en-1-ylidene)dimethylammonium chloride (Gold's Reagent, 2.7 g) and 1,4-dioxan (40 ml) was stirred and heated to reflux for 24 hours. Sodium acetate (1.1 g) and glacial acetic acid (0.6 ml) were added and the mixture was heated to reflux for 3 hours. The mixture was evaporated and water was added to the residue. The solid so obtained was isolated and recrystallised from acetic acid. There was thus obtained 7-benzyloxy-6-methoxyquinazolin-4-one (2.3 g, 61%), m.p. >250° C.

After appropriate repetition of the previous reaction, a mixture of the material so obtained (5 g), acetic anhydride (200 ml), sodium acetate (12 g), 10% palladium-on-carbon catalyst (1.5 g) and toluene (100 ml) was stirred under an atmosphere of hydrogen for 3 hours. The mixture was filtered and the filtrate was evaporated. The residue was partitioned between a mixture of ethyl acetate (500 ml), methanol (20 ml) and water (300 ml). The organic phase was dried (MgSO$_4$) and evaporated. The residue was triturated under hexane. There was thus obtained 7-acetoxy-6-methoxyquinazolin-4-one (1.1 g, 27%).

After appropriate repetition of the previous reaction, a mixture of the material so obtained (2.1 g), thionyl chloride (75 ml) and DMF (5 drops) was stirred and heated to reflux for 3 hours. The mixture was evaporated and the residue was partitioned between methylene chloride and a saturated aqueous sodium bicarbonate solution. The organic phase was dried (MgSO$_4$) and evaporated to give 7-acetoxy-4-chloro-6-methoxyquinazoline (2 g, 93%).

Using an analogous procedure to that described in Example 1, 4-amino-2-chlorobenzophenone was reacted with 7-acetoxy-4-chloro-6-methoxyquinazoline to give the required starting material in 54% yield;

NMR Spectrum: 2.38 (s, 3H), 4.05 (s, 3H), 7.62 (m, 3H), 7.74 (m, 4H), 7.99 (m, 1H), 8.20 (d, 1H), 8.52 (s, 1H), 8.91 (s, 1H), 11.44 (broad s, 1H).

EXAMPLE 18

A mixture of 4-(4-benzoyl-3-chloroanilino)-7-hydroxy-6-methoxyquinazoline (0.3 g), 2-bromoethyl methyl ether (0.155 g), potassium carbonate (0.308 g) and DMA (50 ml) was stirred and heated to 80° C. for 2 hours. The mixture was cooled to ambient temperature and partitioned between ethyl acetate and water. The organic phase was washed with water, dried (MgSO$_4$) and evaporated. The residue was purified by column chromatography using increasingly polar mixtures of methylene chloride and methanol as eluent. There was thus obtained 4-(4-benzoyl-3-chloroanilino)-6-methoxy-7-(2-methoxyethoxy)quinazoline (0.205 g, 60%), m.p. 183°–184° C.;

NMR Spectrum: 3.37 (s, 3H), 3.76 (m, 2H), 4.0 (s, 3H), 4.3 (m, 2H), 7.26 (s, 1H), 7.58 (m, 3H), 7.74 (m, 3H), 7.88 (s, 1H), 8.05 (m, 1H), 8.27 (d, 1H), 8.61 (s, 1H), 9.76 (s, 1H);

Elemental Analysis: Found C, 63.1; H, 5.1; N, 9.0; C$_{25}$H$_{22}$ClN$_3$O$_4$ 0.5 H$_2$O requires C, 63.5; H, 4.9; N, 8.9%.

EXAMPLE 19

Using an analogous procedure to that described in Example 1, 4-chloro-6,7-di-(2-methoxyethoxy)quinazoline hydrochloride was reacted with 4-amino-2-chlorobenzophenone to give 4-(4-benzoyl-3-chloroanilino)-6,7-di-(2-methoxyethoxy)quinazoline hydrochloride salt in 32% yield, m.p. 242°–244° C.;

NMR Spectrum: 3.37 (s, 6H), 3.8 (m, 4H), 4.36 (m, 2H), 4.44 (m, 2H), 7.43 (s, 1H), 7.62 (m, 3H), 7.75 (m, 3H), 8.0 (m, 1H), 8.18 (d, 1H), 8.51 (s, 1H), 8.93 (s, 1H), 11.63 (broad s, 1H);

Elemental Analysis: Found C, 59.3; H, 5.1; N, 8.0; C$_{27}$H$_{26}$ClN$_3$O$_5$ HCl requires C, 59.6; H, 5.0; N, 7.7%.

The 4-chloro-6,7-di-(2-methoxyethoxy)quinazoline hydrochloride used as a starting material was obtained as follows:

A mixture of ethyl 3,4-dihydroxybenzoate (7.29 g), 2-bromoethyl methyl ether (11.3 ml), potassium carbonate (16.6 g) and acetone (100 ml) was stirred and heated to reflux for 20 hours. The mixture was filtered and the filtrate was evaporated. The residue was purified by column chromatography using a 3:2 mixture of hexane and ethyl acetate as eluent. There was thus obtained ethyl 3,4-di-(2-methoxyethoxy)benzoate (9.4 g), m.p. 53°–54° C.

Nitric acid (70%, 75 ml) was stirred and cooled to 0° C. The benzoate so obtained was added portionwise over 30 minutes and the mixture was stirred at 0° C. for 10 minutes. The mixture was diluted into water and extracted with methylene chloride. The organic phase was evaporated to give ethyl 4,5-di-(2-methoxyethoxy)-2-nitrobenzoate (10.4 g).

A mixture of the material so obtained, 10% palladium-on-carbon catalyst (2 g), cyclohexane (25 ml) and methanol (125 ml) was stirred and heated to reflux for 9 hours. The mixture was cooled to ambient temperature, filtered and the filtrate was evaporated. There was thus obtained ethyl 2-amino-4,5-di-(2-methoxyethoxy)benzoate.

A mixture of the material so obtained and formamide (50 ml) was stirred and heated to 170° C. for 18 hours. The mixture was cooled to ambient temperature and the bulk of the remaining formamide was evaporated. The residue was triturated under ethanol to give 6,7-di-(2-methoxyethoxy) quinazolin-4-one (4.9 g).

A mixture of a portion (3.54 g) of the material so obtained, thionyl chloride (50 ml) and DMF (0.3 ml) was stirred and heated to reflux for 2.5 hours. The mixture was evaporated and the residue was stirred under isohexane to give 4-chloro-6,7-di-(2-methoxyethoxy)quinazoline hydrochloride (4.08 g).

EXAMPLE 20

Using an analogous procedure to that described in Example 1, 6-acetoxy-4-chloroquinazoline hydrochloride was reacted with 4-amino-2-chlorobenzophenone to give 6-acetoxy-4-(4-benzoyl-3-chloroanilino)quinazoline hydrochloride salt in 47% yield, m.p. >250° C.;

NMR Spectrum: 2.4 (s, 3H), 7.6 (m, 3H), 7.75 (m, 3H), 7.9–8.1 (m, 3H), 8.2 (d, 1H), 8.7 (d, 1H), 9.0 (s, 1H), 11.25 (broad s, 1H);

Elemental Analysis: Found C, 60.4; H, 3.7; N, 9.2; $C_{23}H_{16}ClN_3O_3$ HCl requires C, 60.8; H, 3.8; N, 9.25%.

The 6-acetoxy-4-chloroquinazoline hydrochloride used as a starting material was obtained as follows:

A mixture of 5-hydroxyanthranilic acid (40 g) and formamide (100 ml) was stirred and heated to 160° C. for 90 minutes. The mixture was cooled to 100° C. and water (600 ml) was added. The solid was isolated and dried. There was thus obtained 6-hydroxyquinazolin-4-one (29.6 g).

A mixture of a portion (24.5 g) of the material so obtained, acetic anhydride (50 ml), 4-dimethylaminopyridine (0.2 g) and DMA (100 ml) was stirred and heated to 80° C. for 1 hour. The mixture was cooled to ambient temperature and evaporated. The residue was triturated under water (500 ml). The solid so obtained was isolated and dried to give 6-acetoxyquinazolin-4-one (23.4 g).

Using an analogous procedure to that described in the first paragraph of the portion of Example 1 which is concerned with the preparation of starting materials, 6-acetoxyquinazolin-4-one was reacted with thionyl chloride to give 6-acetoxy-4-chloroquinazoline hydrochloride which was used without further purification.

EXAMPLE 21

A mixture of 6-acetoxy-4-(4-benzoyl-3-chloroanilino) quinazoline hydrochloride salt (1.55 g), a saturated aqueous ammonium hydroxide solution (10 ml) and methanol (100 ml) was stirred and heated to reflux for 30 minutes. The mixture was evaporated. The residue was stirred with water (100 ml) and the solid material was isolated and washed with water (10 ml) and diethyl ether (20 ml) and dried. There was thus obtained 4-(4-benzoyl-3-chloroanilino)-6-hydroxyquinazoline (1.19 g), m.p. >250° C.;

NMR Spectrum: 7.5–7.65 (m, 4H), 7.7–7.9 (m, 5H), 8.1 (m, 1H), 8.4 (d, 1H), 8.65 (s, 1H);

Elemental Analysis: Found C, 66.0; H, 3.7; N, 11.0; $C_{21}H_4ClN_3O_2$ 0.35$H_2O$ requires C, 66.0; H, 3.9; N, 11.0%.

EXAMPLE 22

A mixture of 4-(4-benzoyl-3-chloroanilino)-6-hydroxyquinazoline (1.09 g), 1,2-dibromoethane (15 ml), potassium carbonate (3 g) and DMF (125 ml) was stirred and heated to 80° C. for 2 hours. The mixture was filtered and the filtrate was evaporated. The residue was purified by column chromatography using increasingly polar mixtures of methylene chloride and methanol to give an oil which was treated with a saturated solution of hydrogen chloride gas in diethyl ether. The precipitate was isolated, washed with diethyl ether and dried. The material so obtained was further purified by column chromatography using increasingly polar mixtures of methylene chloride and methanol as eluent. There was thus obtained 4-(4-benzoyl-3-chloroanilino)-6-(2-bromoethoxy)quinazoline (0.45 g), m.p. 104°–106° C.;

NMR Spectrum: 3.95 (t, 2H), 4.55 (t, 2H), 7.55–7.85 (m, 8H), 8.05 (m, 2H), 8.3 (d, 1H), 8.75 (s, 1H), 9.9 (broad s, 1H);

Elemental Analysis: Found C, 55.4; H, 3.9; N, 8.1; $C_{23}H_{17}BrClN_3O_2$ 0.9$H_2O$ requires C, 55.4; H, 3.8; N, 8.4%.

EXAMPLE 23

A mixture of 4-(4-benzoyl-3-chloroanilino)-6-(2-bromoethoxy)quinazoline (0.35 g) and a solution of methylamine in ethanol (33%, 30 ml) was stirred and heated to 55° C. for 5 hours under a condenser loaded with solid carbon dioxide. The mixture was evaporated and the residue was purified by column chromatography using a 15:0.8:0.1 mixture of methylene chloride, methanol and a saturated aqueous ammonium hydroxide solution as eluent. The material so obtained was treated with a saturated solution of hydrogen chloride in diethyl ether. The precipitate was isolated and dried. There was thus obtained 4-(4-benzoyl-3-chloroanilino)-6-(2-methylaminoethoxy)quinazoline dihydrochloride salt (0.24 g), m.p. >250° C.;

NMR Spectrum ($CD_3SOCD_3+CD_3CO_2D$): 2.75 (s, 3H), 3.5 (t, 2H), 4.6 (t, 2H), 7.55–7.85 (m, 7H), 7.95–8.1 (m, 2H), 8.25 (d, 1H), 8.65 (d, 1H), 9.0 (s, 1H);

Elemental Analysis: Found C, 55.5; H, 4.7; N, 11.0; $C_{24}H_{21}ClN_4O_2$ 2HCl 0.6$H_2O$ requires C, 55.8; H, 4.7; N, 10.8%.

EXAMPLE 24

Using an analogous procedure to that described in Example 1, 6-acetoxy-4-chloroquinazoline hydrochloride was reacted with 4-amino-2-chlorophenyl 2-thienyl ketone to give 6-acetoxy-4-[3-chloro-4-(2-thienylcarbonyl)anilino] quinazoline hydrochloride salt in 77% yield, m.p. >250° C.;

NMR Spectrum: 2.4 (s, 3H), 7.3 (m, 1H), 7.55 (m, 1H), 7.75 (d, 1H), 7.9–8.2 (m, 5H), 9.05 (s, 1H), 11.5 (broad s, 1H);

Elemental Analysis: Found C, 53.7; H, 3.2; N, 8.8; $C_{21}H_{14}ClN_3O_3S$ 1HCl 0.5$H_2O$ requires C, 53.7; H, 3.4; N, 8.95%.

EXAMPLE 25

The sequence of reactions described in Examples 21 to 23 were repeated except that 6-acetoxy-4-[3-chloro-4-(2-thienylcarbonyl)anilino]quinazoline hydrochloride salt was used in place of 6-acetoxy-4-[4-benzoyl-3-chloroanilino) quinazoline hydrochloride salt. There were thus obtained:

Compound 25(1): 4-[3-chloro-4-(2-thienylcarbonyl) anilino]-6-hydroxyquinazoline, m.p. >250° C.;

NMR Spectrum: 7.3 (m, 1H), 7.45 (m, 1H), 7.55 (m, 1H), 7.65 (d, 1H), 7.75 (d, 1H), 7.85 (d, 1H), 8.05–8.15 (m, 2H), 8.35 (d, 1H), 8.6 (s, 1H), 9.8 (broad s, 1H), 10.2 (broad s, 1H);

Compound 25(2): 6-(2-bromoethoxy)-4-[3-chloro-4-(2-thienylcarbonyl)anilino]quinazoline, m.p. 175°–177° C.;

NMR Spectrum: 3.95 (t, 2H), 4.55 (t, 2H), 7.25 (t, 1H), 7.6 (m, 3H), 7.8 (d, 1H), 8.0 (d, 1H), 8.1 (m, 1H), 8.15 (d, 1H), 8.3 (d, 1H), 8.65 (s, 1H), 9.85 (broad s, 1H); and Compound 25(3): 4-[3-chloro-4-(2-thienylcarbonyl)anilino] -6-(2-methylaminoethoxy)quinazoline dihydrochloride salt, m.p. >250° C.;

NMR Spectrum (CD$_3$SOCD$_3$+CD$_3$CO$_2$D): 2.65 (s, 3H), 3.45 (t, 2H), 4.55 (t, 2H), 7.25 (t, 1H), 7.5 (d, 1H), 7.65 (m, 2H), 7.9 (d, 1H), 8.1 (m, 2H), 8.25 (d, 1H), 8.5 (d, 1H), 8.85 (s, 1H).

EXAMPLE 26

Using an analogous procedure to that described in Example 21, 6-acetoxy-4-[3-chloro-4-(1-methylimidazol-2-ylthio)anilino]quinazoline hydrochloride salt was hydrolysed to give 4-[3-chloro-4-(1-methylimidazol-2-ylthio)anilino]-6-hydroxyquinazoline in 64% yield;

NMR Spectrum: 3.45 (s, 3H), 6.65 (d, 1H), 7.15 (d, 1H), 7.45 (m, 2H), 7.65–7.8 (m, 3H), 8.25 (d, 1H), 8.45 (s, 1H), 9.55 (broad s, 1H).

The starting material was obtained by the reaction of 6-acetoxy-4-chloroquinazoline hydrochloride with 4-amino-2-chlorophenyl 1-methylimidazol-2-yl sulphide using an analogous procedure to that described in Example 1.

EXAMPLE 27

Using an analogous procedure to that described in Example 1, 6-acetoxy-4-chloroquinazoline hydrochloride was reacted with 4-amino-2-fluorophenyl 1-methylimidazol-2-yl sulphide to give 6-acetoxy-4-[3-fluoro-4-(1-methylimidazol-2-ylthio)anilino]quinazoline dihydrochloride salt in 58% yield, m.p. 245–248 (decomposes);

NMR Spectrum: 2.5 (s, 3H), 4.0 (s, 3H), 7.5–8.2 (m, 7H), 8.95 (d, 1H), 9.1 (s, 1H), 11.6 (broad s, 1H);

Elemental Analysis: Found C, 49.2; H, 3.7; N, 14.1; C$_{20}$H$_{16}$FN$_5$O$_2$S 2HCl 0.3H$_2$O requires C, 49.2; H, 3.8; N, 14.4%.

The 4-amino-2-fluorophenyl 1-methylimidazol-2-yl sulphide used as a starting material was obtained from 3,4-difluoronitrobenzene using analogous procedures to those mentioned in the portion of Example 10 which is concerned with the preparation of starting materials.

EXAMPLE 28

A mixture of 4-(4-hydroxy-3-methylanilino)-6,7-dimethoxyquinazoline (1 g), 4-cyanobenzyl bromide (0.564 g), potassium carbonate (1.59 g), potassium iodide (0.716 g), acetone (50 ml) and ethanol (50 ml) was stirred and heated to reflux for 16 hours. A second portion of 4-cyanobenzyl bromide (0.3 g) was added and the mixture was stirred and heated to reflux for 2 days. The mixture was cooled to ambient temperature, filtered and evaporated. The residue was purified by column chromatography using a 19:1 mixture of methylene chloride and methanol as eluent. There was thus obtained 4-[4-(4-cyanobenzyloxy)-3-methylanilino]-6,7-dimethoxyquinazoline (0.357 g, 29%), m.p. 211°–213° C.;

NMR Spectrum: 2.27 (s, 3H), 3.92 (s, 3H), 3.94 (s, 3H), 5.26 (s, 2H), 7.01 (d, 1H), 7.16 (s, 1H), 7.49 (s, 1H), 7.52 (m, 1H), 7.68 (d, 2H), 7.86 (m, 3H), 8.4 (s, 1H), 9.47 (s, 1H);

Elemental Analysis: Found C, 69.6; H, 5.3; N, 12.5; C$_{25}$N$_{22}$N$_4$O$_3$ 0.2H$_2$O requires C, 69.8; H, 5.25; N, 13.0%.

The 4-(4-hydroxy-3-methylanilino)-6,7-dimethoxyquinazoline used as a starting material was obtained in 90% yield by the reaction of 4-chloro-6,7-dimethoxyquinazoline hydrochloride and 4-hydroxy-3-methylaniline using an analogous procedure to that described in Example 1 except that the reactants were heated to reflux for 3 hours.

EXAMPLE 29

Using an analogous procedure to that described in Example 28, except that the reaction solvent was acetone and the reactants were heated to reflux for 2 hours, 4-(4-hydroxy-3-methylanilino)-6,7-dimethoxyquinazoline was reacted with 4-pyridylmethyl chloride to give 6,7-dimethoxy-4-[3-methyl-4-(4-pyridylmethoxy)anilino] quinazoline in 28% yield, m.p. 229°–231° C.;

NMR Spectrum: 2.3 (s, 3H), 3.94 (s, 3H), 3.96 (s, 3H), 5.24 (s, 2H), 7.0 (d, 1H), 7.17 (s, 1H), 7.5 (m, 4H), 7.82 (s, 1H), 8.4 (s, 1H), 8.6 (m, 2H), 9.25 (broad s, 1H); Elemental Analysis: Found C, 61.6; H, 5.1; N, 12.3; C$_{23}$H$_{22}$N$_4$O$_3$ 0.5CH$_2$Cl$_2$ 0.6H$_2$O requires C, 61.9; H, 5.35; N, 12.3%.

EXAMPLE 30

The procedure disclosed in Example 29 was repeated except that 3-pyridylmethyl chloride was used in place of 4-pyridylmethyl chloride. There was thus obtained 6,7-dimethoxy-4-[3-methyl-4-(3-pyridylmethoxy)anilino] quinazoline in 10% yield, m.p. 211°–213° C.;

NMR Spectrum: 2.24 (s, 3H), 3.93 (s, 3H), 3.95 (s, 3H), 5.20 (s, 2H), 7.08 (d, 1H), 7.18 (s, 1H), 7.58–7.42 (m, 3H), 7.82 (s, 1H), 7.91 (m, 1H), 8.39 (s, 1H), 8.56 (m, 1H), 8.71 (d, 1H), 9.36 (s, 1H);

Elemental Analysis: Found C, 64.9; H, 5.5; N, 12.9; C$_{23}$H$_{22}$N$_4$O$_3$ 1.2H$_2$O requires C, 65.1; H, 5.8; N, 13.2%.

EXAMPLE 31

A mixture of 7-hydroxy-6-methoxy-4-[3-methyl-4-(2-pyridylmethoxy)anilino]quinazoline (0.4 g), 2,2,2-trifluoroethyl trichloromethanesulphonate (0.29 g), potassium carbonate (0.28 g) and DMF (50 ml) was stirred and heated to 100° C. for 3 hours and stored at ambient temperature for 66 hours. The mixture was partitioned between ethyl acetate and water. The organic phase was washed with water and with brine, dried (MgSO$_4$) and evaporated. The mixture was concentrated by evaporation. Hexane was added and the precipitate was isolated. There was thus obtained 6-methoxy-4-[3-methyl-4-(2-pyridylmethoxy) anilino]-7-(2,2,2-trifluoroethoxy)quinazoline (0.225 g, 46%), m.p. 213°–215° C.;

NMR Spectrum: 2.32 (s, 3H), 4.07 (s, 3H), 5.08 (m, 2H), 5.32-(s, 2H), 7.15 (d, 1H), 7.46 (m, 4H), 7.68 (d, 1H), 8.0 (m, 1H), 8.36 (s, 1H), 8.66 (d, 1H), 8.8 (s, 1H), 11.39 (broad s, 1H);

Elemental Analysis: Found C, 60.0; H, 4.6; N, 11.5; C$_{24}$H$_{21}$F$_3$N$_4$O$_3$ 0.6H$_2$O requires C, 59.9; H, 4.65; N, 11.6%.

The 7-hydroxy-6-methoxy-4-[13-methyl-4-(2-pyridylmethoxy)anilino]quinazoline used as a starting material was obtained as follows:

Using an analogous procedure to that described in Example 1 except that the reaction mixture was heated to reflux for 3 hours, 7-acetoxy-4-chloro-6-methoxyquinazoline was reacted with 5-amino-2-tolyl 2-pyridylmethyl ether to give 7-acetoxy-6-methoxy-4-[3-methyl-4-(2-pyridylmethoxy)anilino]quinazoline in 64% yield;

NMR Spectrum: 2.32 (s, 3H), 2.38 (s, 3H), 4.03 (s, 3H), 5.27 (s, 2H), 7.14 (m, 1H), 7.42 (m, 2H), 7.51 (s, 1H), 7.60 (d, 1H), 7.74 (s, 1H), 7.92 (m, 1H), 8.48 (s, 1H), 8.63 (d, 1H), 8.81 (s, 1H), 11.42 (broad s, 1H).

The material so obtained was hydrolysed using an analogous procedure to that described in Example 21. There was thus obtained 7-hydroxy-6-methoxy-4-[3-methyl-4-(2-pyridylmethoxy)anilino]-quinazoline in 91% yield;

NMR Spectrum: 2.31 (s, 3H), 3.98 (s, 3H), 5.24 (s, 2H), 7.03 (d, 1H), 7.08 (s, 1H), 7.36 (m, 1H), 7.5 (m, 2H), 7.58 (d, 1H), 7.87 (m, 2H), 8.42 (s, 1H), 8.6 (m, 1H), 9.65 (s, 1H).

EXAMPLE 32

Hydrogen chloride gas was led during 5 minutes into a stirred mixture of 4-(4-benzoyl-3-chloroanilino)-6-nitroquinazoline hydrochloride salt (0.3 g), iron powder (0.3 g) and ethanol (20 ml). The mixture was stirred at ambient temperature for 16 hours. The mixture was evaporated and the residue was partitioned between ethyl acetate and 2M aqueous sodium hydroxide solution. The organic phase was dried ($MgSO_4$) and evaporated. The residue was purified by column chromatography using increasingly polar mixtures of methylene chloride and methanol as eluent. There was thus obtained 6-amino-4-(4-benzoyl-3-chloro-anilino)quinazoline (0.03 g), m.p. 249°–252° C.;

NMR Spectrum: 5.5 (s, 2H), 7.3 (m, 2H), 7.6 (m, 4H), 7.7 (d, 1H), 7.8 (m, 2H), 8.05 (m, 1H), 8.3 (d, 1H), 8.5 (s, 1H), 9.7 (broad s, 1H).

The 4-(4-benzoyl-3-chloroanilino)-6-nitroquinazoline hydrochloride salt used as a starting material was obtained in 33% yield by the reaction of 4-chloro-6-nitroquinazoline (European Patent Application No. 0566226, within Example 8 thereof) and 4-amino-2-chlorobenzophenone using an analogous procedure to that described in Example 1.

EXAMPLE 33

Using an analogous procedure to that described in Example 22, a mixture of 4-[3-fluoro-4-(1-methylimidazol-2-ylthio)anilino]-6-hydroxyquinazoline was reacted with 1,2-dibromoethane to give 6-(2-bromoethoxy)-4-[3-fluoro-4-(1-methylimidazol-2-ylthio)anilino]quinazoline in 45% yield;

NMR Spectrum: 3.68 (s, 3H), 3.92 (t, 2H), 4.5 (t, 2H), 7.07 (d, 1H), 7.1 (t, 1H), 7.45 (d, 1H), 7.55–7.65 (m, 2H), 7.78 (d, 1H), 7.95 (d, 1H), 8.05 (m, 1H), 8.57 (s, 1H), 9.73 (s, 1H);

Elemental Analysis: Found C, 50.4; H, 3.5; N, 14.4; $C_{20}H_{17}BrFN_5OS$ $0.15H_2O$ requires C, 50.4; H, 3.7; N, 14.7%.

The 4-[3-fluoro-4-(1-methylimidazol-2-ylthio)anilino]-6-hydroxyquinazoline used as a starting material was obtained in 58% yield by the hydrolysis of 6-acetoxy-4-]3-fluoro-4-(1-methylimidazol-2-ylthio)anilino)quinazoline using an analogous procedure to that described in Example 21.

EXAMPLE 34

Using an analogous procedure to that described in Example 23, 6-(2-bromoethoxy)-4-[3-fluoro-4-(1-methylimidazol-2-ylthio)anilino]-quinazoline was reacted with methylamine and the material obtained from the chromatographic purification was triturated under diethyl ether rather than being treated with hydrogen chloride. There was thus obtained 4-[3-fluoro-4-(1-methylimidazol-2-ylthio)anilino]-6-(2-methylaminoethoxy)quinazoline in 65% yield, m.p. 194°–195° C.;

NMR Spectrum: 2.38 (s, 3H), 2.93 (t, 2H), 3.68 (s, 3H), 4.22 (t, 2H), 7.07 (d, 1H), 7.1 (t, 1H), 7.43 (t, 1H), 7.53 (m, 1H), 7.63 (m, 1H), 7.75 (d, 1H), 7.92 (d, 1H), 8.05 (m, 1H), 8.55 (s, 1H), 9.72 (s, 1H);

Elemental Analysis: Found C, 59.6; H, 5.0; N, 19.8; $C_{21}H_{21}FN_6OS$ requires C, 59.4; H, 5.0; N, 19.8%.

EXAMPLE 35

A mixture of 4-[4-(4-cyanobenzyloxy)-3-methylanilino]-6,7-dimethoxyquinazoline (0.05 g), powdered potassium hydroxide (0.05 g) and tert-butanol (3 ml) was stirred and heated to reflux for 90 minutes. A second portion of potassium hydroxide (0.1 g) was added and the mixture was heated to reflux for 4 hours. The mixture was cooled to ambient temperature and partitoned between methylene chloride and a saturated aqueous sodium chloride solution. The organic phase was dried ($MgSO_4$) and evaporated. There was thus obtained 4-[4-(4-carbamoylbenzyloxy)-3-methylanilino]-6,7-dimethoxyquinazoline (0.022 g), m.p. >250° C.;

NMR Spectrum: 2.28 (s, 3H), 3.94 (s, 3H), 3.96 (s, 3H), 5.21 (s, 2H), 7.04 (s, 1H), 7.16 (s, 1H), 7.32 (s, 1H), 7.48 (m, 2H), 7.55 (d, 2H), 7.82 (s, 1H), 7.88–7.95 (m, 3H), 8.38 (s, 1H), 9.32 (s, 1H);

Elemental Analysis: Found C, 65.2; H, 5.7; N, 15.7; $C_{25}H_{24}N_4O_4$ $0.8H_2O$ requires C, 65.4; H, 5.6; N, 12.2%

EXAMPLE 36

A mixture of 6-(2-bromoethoxy)-4-[3-methyl-4-(2-pyridylmethoxy)anilino]quinazoline (0.2 g) and a solution of methylamine in ethanol (33%, 50 ml) was stirred and heated to reflux for 3 hours. The mixture was evaporated and the residue was purified by column chromatography using increasingly polar mixtures of methylene chloride and methanol as eluent. There was thus obtained 6-(2-methylaminoethoxy)-4-[3-methyl-4-(2-pyridylmethoxy)anilino]quinazoline as a gum (0.03 g, 17%);

NMR Spectrum: 2.29 (s, 3H), 2.38 (s, 3H), 2.96 (t, 2H), 4.2 (t, 2H), 5.23 (s, 2H), 7.04 (d, 1H), 7.36 (m, 1H), 7.47 (m, 1H), 7.55 (m, 3H), 7.69 (d, 1H), 7.86 (m, 2H), 8.42 (s, 1H), 8.59 (d, 1H), 9.46 (s, 1H).

The 6-(2-bromoethoxy)-4-[3-methyl-4-(2-pyridylmethoxy)anilino]quinazoline used as a starting material was obtained as follows:

Using an analogous procedure to that described in Example 1, 6-acetoxy-4-chloroquinazoline was reacted with 5-amino-2-tolyl 2-pyridylmethyl ether to give 6-acetoxy-4-[3-methyl-4-(2-pyridylmethoxy)anilino]quinazoline in 35% yield, m.p. 149°–151° C.;

NMR Spectrum: 2.32 (s, 3H), 2.41 (s, 3H), 5.28 (s, 2H), 7.1 (d, 1H), 7.38–7.52 (m, 3H), 7.6 (d, 1H), 7.93 (m, 3H), 8.62 (m, 2H), 8.88 (s, 1H), 11.28 (s, 1H).

The material so obtained was hydrolysed using an analogous procedure to that described in Example 17. There was thus obtained 6-hydroxy-4-[3-methyl-4-(2-pyridylmethoxy)anilino]quinazoline in 93% yield, m.p. >250° C.;

NMR Spectrum: 2.3 (s, 3H), 5.21 (s, 2H), 6.98 (d, 1H), 7.37 (m, 2H), 7.59 (m, 4H), 7.74 (d, 1H), 7.86 (m, 1H), 8.38 (s, 1H), 8.6 (d, 1H), 9.32 (s, 1H), 9.94 (s, 1H).

The material so obtained was reacted with 1,2-dibromoethane using an analogous procedure to that described in Example 22. There was thus obtained 6-(2-bromoethoxy)-4-[3-methyl-4-(2-pyridylmethoxy)anilino]quinazoline in 9% yield;

NMR Spectrum: 2.3 (s, 3H), 3.92 (t, 2H), 4.5 (t, 2H), 5.23 (s, 2H), 7.04 (d, 1H), 7.38 (m, 1H), 7.53 (m, 2H), 7.72 (d, 1H), 7.85 (m, 1H), 7.94 (m, 3H), 8.43 (s, 1H), 8.6 (m, 1H), 9.47 (s, 1H).

EXAMPLE 37

A solution of 2-dimethylaminoethyl chloride, hydrochloride salt (1.19 g) in water (20 ml) was basified by the addition of 2M sodium hydroxide solution. The mixture was extracted with toluene and the organic extract was dried over pellets of potassium hydroxide. There was thus obtained a solution of 2-dimethylaminoethyl chloride.

Sodium hydride (60% dispersion in mineral oil, 0.4 g) was added to a solution of 6-hydroxy-4-[3-methyl-4-(2-pyridylmethoxy)anilino]-quinazoline (2.7 g) in DMF (80 ml). The mixture was stirred and heated to 100° C. for 30 minutes. The solution of 2-dimethylaminoethyl chloride in toluene was added and the mixture was heated to 100° C. for 2.5 hours. The mixture was cooled to ambient temperature and partitioned between ethyl acetate and water. The organic phase was washed with water and with brine, dried ($MgSO_4$) and evaporated. The residue was purified by column chromatography using a 20:1 mixture of methylene chloride and methanol as eluent. There was thus obtained 6-(2-dimethylaminoethoxy)-4-[3-methyl-4-(2-pyridylmethoxy) anilino]quinazoline (0.8 g, 25%), m.p. 93°–95° C.;

NMR Spectrum: 2.32 (s, 3H), 2.78 (t, 2H), 4.24 (t, 2H), 5.22 (s, 2H), 7.03 (d, 1H), 7.36 (m, 1H), 7.45 (m, 1H), 7.55 (m, 3H), 7.67 (d, 1H), 7.86 (m, 2H), 8.39 (s, 1H), 8.58 (m, 1H), 9.43 (s, 1H);

Elemental Analysis: Found C, 66.0; H, 6.5; N, 15.4; $C_{24}H_{27}N_5O_2$ 1.4$H_2O$ requires C, 66.0; H, 6.6; N, 15.4%.

EXAMPLE 38

A mixture of 4-[2-fluoro-4-(2-pyridylmethoxy)anilino]-6-hydroxyquinazoline (1.23 g), 3-morpholinopropyl chloride (*J.Amer.Chem.Soc.*, 1945, 67, 736; 1.5 g), potassium carbonate (3 g) and DMF (100 ml) was stirred and heated to 105° C. for 2 hours. The mixture was cooled to ambient temperature, filtered and the filtrate was evaporated. The residue was purified by column chromatography using increasingly polar mixtures of methylene chloride and methanol as eluent. The material so obtained was triturated under diethyl ether. There was thus obtained 4-[2-fluoro-4-(2-pyridylmethoxy)anilino]-6-(3-morpholinopropoxy) quinazoline (0.89 g), m.p. 164°–166° C.;

NMR Spectrum: 1.98 (m, 2H), 2.4 (m, 4H), 3.6 (t, 4H), 4.15 (t, 2H), 5.25 (s, 2H), 6.95 (m, 1H), 7.07 (m, 1H), 7.35 (m, 2H), 7.45 (m, 1H), 7.55 (m, 1H), 7.68 (d, 1H), 7.83 (t, 1H), 7.9 (m, 1H), 8.33 (s, 1H), 8.6 (m, 1H), 9.48 (s, 1H);

Elemental Analysis: Found C, 66.1; H, 5.9; N, 14.0; $C_{27}H_{28}FN_5O_3$ requires C, 66.2; H, 5.8; N, 14.3%.

The 4-[2-fluoro-4-(2-pyridylmethoxy)anilino]-6-hydroxyquinazoline used as a starting material was obtained as follows:

Using an analogous procedure to that described in Example 1, 6-acetoxy-4-chloroquinazoline was reacted with 4-amino-3-fluorophenyl 2-pyridylmethyl ether to give 6-acetoxy-4-[2-fluoro-4-(2-pyridylmethoxy)anilino] quinazoline in 94% yield.

The material so obtained was hydrolysed using an analogous procedure to that described in Example 17 to give 4-[2-fluoro-4-(2-pyridylmethoxy)anilino]-6-hydroxyquinazoline in 71% yield.

EXAMPLE 39

A mixture of 6-hydroxy-7-methoxy-4-[3-methyl-4-(2-pyridylmethoxy)anilino]quinazoline (1.25 g), 3-dimethylaminopropyl chloride, hydrochloride salt (1.04 g), potassium carbonate (2.2 g) and DMF (80 ml) was stirred and heated to 80° C. for 3 hours. The mixture was cooled to ambient temperature and partitioned between ethyl acetate and water. The organic phase was washed with water and with brine, dried ($MgSO_4$) and evaporated. The material so obtained was recrystallised from a mixture of hexane and methylene chloride. There was thus obtained 6-(3-dimethylaminopropoxy)-7-methoxy-4-[3-methyl-4-(2-pyridylmethoxy)anilino]quinazoline (0.81 g, 52%), m.p. 149°–151° C.;

NMR Spectrum: 1.97 (m, 2H), 2.18 (s, 6H), 2.3 (s, 3H), 2.43 (t, 2H), 3.93 (s, 3H), 4.16 (t, 2H), 5.21 (s, 2H), 7.03 (d, 1H), 7.15 (s, 1H), 7.35 (m, 1H), 7.49 (s, 1H), 7.56 (m, 2H), 7.62 (s, 1H), 7.66 (m, 1H), 8.37 (s, 1H), 8.59 (m, 1H), 9.34 (s, 1H);

Elemental Analysis: Found C, 67.9; H, 6.7; N, 14.6; $C_{27}H_{31}N_5O_3$ requires C, 68.5; H, 6.6; N, 14.8%.

The 6-hydroxy-7-methoxy-4-[3-methyl-4-(2-pyridylmethoxy)anilino]quinazoline used as a starting material was obtained as follows:

6,7-Dimethoxyquinazolin-4-one (European Patent Application No. 0 566 226, Example 1 thereof; 26.5 g) was added portionwise to stirred methanesulphonic acid (175 ml). L-Methionine (22 g) was added and the resultant mixture was stirred and heated to reflux for 5 hours. The mixture was cooled to ambient temperature and poured onto a mixture (750 ml) of ice and water. The mixture was neutralised by the addition of a concentrated (40%) aqueous sodium hydroxide solution. The precipitate was isolated, washed with water and dried. There was thus obtained 6-hydroxy-7-methoxyquinazolin-4-one (11.5 g).

After repetition of the previous reaction, a mixture of 6-hydroxy-7-methoxyquinazolin-4-one (14.8 g), acetic anhydride (110 ml) and pyridine (14 ml) was stirred and heated to 100° C. for 2 hours. The mixture was poured onto a mixture (200 ml) of ice and water. The precipitate was isolated, washed with water and dried. There was thus obtained 6-acetoxy-7-methoxyquinazolin-4-one (13 g, 75%);

NMR Spectrum: 2.3 (s, 3H), 3.8 (s, 3H), 7.3 (s, 1H), 7.8 (s, 1H), 8.1 (s, 1H), 12.2 (broad s, 1H).

After repetition of the previous steps, a mixture of 6-acetoxy-7-methoxyquinazolin-4-one (15 g), thionyl chloride (215 ml) and DMF (4.3 ml) was stirred and heated to 90° C. for 4 hours. The mixture was cooled to ambient temperature and the thionyl chloride was evaporated. There was thus obtained 6-acetoxy-4-chloro-7-methoxyquinazoline, hydrochloride salt, which was used without further purification.

Using an analogous procedure to that described in Example 1, 6-acetoxy-4-chloro-7-methoxyquinazoline, hydrochloride salt, was reacted with 5-amino-2-tolyl 2-pyridylmethyl ether to give 6-acetoxy-7-methoxy-4-[3-methyl-4-(2-pyridylmethoxy)anilino]quinazoline in 60% yield;

NMR Spectrum: 2.3 (s, 3H), 2.38 (s, 3H), 4.01 (s, 3H), 5.26 (s, 2H), 7.1 (d, 1H), 7.34–7.48 (m, 4H), 7.58 (d, 1H), 7.89 (m, 1H), 8.6 (m, 2H), 8.84 (s, 1H), 11.04 (s, 1H).

The material so obtained was hydrolysed using an analogous procedure to that described in Example 17 to give 6-hydroxy-7-methoxy-4-[3-methyl-4-(2-pyridylmethoxy) anilino]quinazoline in 44% yield, m.p. 234°–235° C.;

NMR Spectrum: 2.3 (s, 3H), 3.96 (s, 3H), 5.2 (s, 2H), 6.98 (d, 1H), 7.16 (s, 1H), 7.35 (m, 1H), 7.54 (m, 3H), 7.78 (s, 1H), 7.88 (m, 1H), 8.35 (s, 1H), 8.59 (m, 1H), 9.18 (s, 1H), 9.52 (s, 1H).

EXAMPLE 40

Using an analogous procedure to that described in Example 37, 6-hydroxy-7-methoxy-4-[3-methyl-4-(2-pyridylmethoxy)anilino]quinazoline was reacted with 2-dimethylaminoethyl chloride to give 6-(2-dimethylaminoethoxy)-7-methoxy-4-[3-methyl-4-(2-pyridylmethoxy)anilino]quinazoline in 47% yield, m.p. 125°–126° C.;

NMR Spectrum: 2.27 (s, 6H), 2.65 (t, 2H), 3.95 (s, 3H), 4.2 (t, 2H), 7.15 (m, 1H), 7.2 (s, 1H), 7.38 (m, 1H), 7.57 (m, 1H), 7.82 (s, 1H), 8.33 (s, 1H), 9.43 (s, 1H);

Elemental Analysis: Found C, 66.7; H, 6.2; N, 14.8; $C_{26}H_{29}N_5O_3$ 0.5$H_2O$ requires C, 66.7; H, 6.4; N, 14.95%.

EXAMPLE 41

Using an analogous procedure to that described in Example 38, 6-hydroxy-7-methoxy-4-[3-methyl-4-(2-pyridylmethoxy)anilino]quinazoline was reacted with 3-morpholinopropyl chloride to give 7-methoxy-4-[3-methyl-4-(2-pyridylmethoxy)anilino]-6-(3-morpholinopropoxy)quinazoline in 53% yield;

NMR Spectrum: 1.99 (t, 2H), 2.38 (t, 4H), 2.47 (t, 2H), 3.59 (t, 4H), 3.94 (s, 3H), 4.18 (t, 2H), 5.22 (s, 2H), 7.03 (d, 1H), 7.15 (s, 1H), 7.35 (m, 1H), 7.53 (m, 3H), 7.85 (m, 2H), 8.38 (s, 1H), 8.6 (d, 1H), 9.32 (s, 1H);

Elemental Analysis: Found C, 66.0; H, 6.5; N, 13.0; $C_{29}H_{33}N_5O_4$ 0.6$H_2O$ requires C, 66.2; H, 6.55; N; 13.5%.

EXAMPLE 42

A mixture of 6-amino-4-[3-methyl-4-(2-pyridylmethoxy)anilino]quinazoline (0.78 g), acetic anhydride (1.1 ml) and DMA (8 ml) was stirred at ambient temperature and the residue was triturated under methylene chloride. There was thus obtained 6-acetamido-4-[3-methyl-4-(2-pyridylmethoxy)anilino]quinazoline (0.72 g), m.p. 246°–248° C.;

NMR Spectrum: 2.15 (s, 3H), 2.32 (s, 3H), 5.25 (s, 2H), 7.04 (d, 1H), 7.37 (m, 1H), 7.57 (d, 3H), 7.74 (d, 1H), 7.88 (m, 2H), 8.46 (s, 1H), 8.63 (m, 2H), 9.62 (s, 1H), 10.22 (s, 1H);

Elemental Analysis: Found C, 69.0; H, 5.1; N, 17.5; $C_{23}H_{21}N_5O_2$ requires C, 69.2; H, 5.3; N, 17.5%.

The 6-amino-4-[3-methyl-4-(2-pyridylmethoxy)anilino]quinazoline used as a starting material was obtained as follows:

A mixture of 6-nitroquinazolin-4-one (8.25 g), thionyl chloride (90 ml) and DMF (0.6 ml) was stirred and heated to reflux for 3 hours. The mixture was evaporated and the residue was dissolved in methylene chloride (75 ml). The solution was cooled in an ice-bath and triethylamine (5.4 ml) was added dropwise. Isopropanol (100 ml) and a solution of 5-amino-2-tolyl 2-pyridylmethyl ether (10.1 g) in isopropanol (100 ml) were added in turn and the mixture was concentrated by evaporation of the methylene chloride. A further portion of isopropanol (150 ml) was added and the mixture was heated to reflux for 2 hours. The mixture was stored at ambient temperature for 16 hours. The solid was isolated and washed with diethyl ether. There was thus obtained 4-[3-methyl-4-(2-pyridylmethoxy)anilino]-6-nitroquinazoline (13.3 g) which was used without further purification.

A mixture of a portion (1.75 g) of the material so obtained and ethanol (40 ml) was added portionwise to a stirred mixture of stannous chloride dihydrate (4.1 g) and ethanol (15 ml) which was stirred and heated to 60° C. The resultant mixture was heated to reflux for 2 hours. The mixture was allowed to cool to ambient temperature and to stand for 40 hours. The precipitate was isolated and the filtrate was evaporated. The isolated solid and the residue from the filtrate were combined and partitioned between ethyl acetate and a concentrated (30%) aqueous ammonium hydroxide solution. The two-phase mixture was filtered and the organic phase was separated, washed with brine, dried (MgSO$_4$) and evaporated. The resultant residue was purified by column chromatography using a 9:1 mixture of methylene chloride and methanol as eluent. The material so obtained was triturated under ethyl acetate. There was thus obtained 6-amino-4-[3-methyl-4-(2-pyridylmethoxy)anilino]quinazoline (0.88 g, 55%), NMR Spectrum: 2.29 (s, 3H), 5.2 (s, 2H), 5.45 (broad s, 2H), 6.98 (d, 1H), 7.21 (m, 1H), 7.35 (m, 2H), 7.48 (d, 1H), 7.55 (m, 3H), 7.86 (m, 1H), 8.25 (s, 1H), 8.59 (m, 1H), 9.12 (s, 1H).

EXAMPLE 43

Concentrated hydrochloric acid (0.235 ml) was added to a stirred mixture of 2-methoxyacetaldehyde dimethyl acetal (3.58 ml) and water (16 ml). The mixture was stirred at ambient temperature for 2 hours. The resultant mixture was neutralised by the addition of a saturated aqueous sodium bicarbonate solution. The mixture so obtained was added to a stirred suspension of 6-amino-4-[3-methyl-4-(2-pyridylmethoxyanilino]quinazoline (2 g) in a mixture of ethanol (50 ml) and glacial acetic acid (0.65 ml). Sodium cyanoborohydride (0.71 g) was added and the resultant mixture was stirred at ambient temperature for 16 hours. The mixture was basified to pH8 by the addition of a saturated aqueous sodium bicarbonate solution and the mixture was evaporated. The residue was partitioned between methylene chloride and water. The organic phase was washed with brine, dried (MgSO$_4$) and evaporated. The residue was purified by column chromatography using a 9:1 mixture of methylene chloride and methanol as eluent. The material so obtained was triturated under a mixture of methylene chloride and diethyl ether. There was thus obtained 6-(2-methoxyethylamino)-4-[3-methyl-4-(2-pyridylmethoxy)anilino]quinazoline (1.7 g), m.p. 188°–190° C.;

NMR Spectrum: 2.3 (s, 3H), 3.34 (s, 3H), 3.4 (t, 2H), 3.6 (t, 2H), 5.2 (s, 2H), 6.09 (t, 1H), 7.02 (d, 1H), 7.2–7.38 (m, 3H), 7.47–7.59 (m, 4H), 7.86 (m, 1H), 8.25 (s, 1H), 8.59 (m, 1H), 9.18 (s, 1H);

Elemental Analysis: Found C, 68.7; H, 6.0; N, 16.6; $C_{24}H_{25}N_5O_2$ 0.2$H_2O$ requires C, 68.8; H, 6.1; N, 16.7%.

EXAMPLE 44

A mixture of 6-amino-4-[3-methyl-4-(2-pyridylmethoxy)anilino]quinazoline (4.2 g), 2-chloroacetyl chloride (0.95 ml) and DMA (15 ml) was stirred at ambient temperature for 3 hours. The mixture was evaporated and the residue was triturated under acetone. There was thus obtained 6-(2-chloroacetamido)-4-[3-methyl-4-(2-pyridylmethoxy)anilino]quinazoline, hydrochloride salt (5.4 g), m.p. >250° C.;

NMR Spectrum: 2.3 (s, 3H), 4.43 (s, 2H), 5.28 (s, 2H), 7.11 (d, 1H), 7.36–7.48 (m, 3H), 7.61 (d, 1H), 7.95 (m, 2H), 8.13 (m, 1H), 8.63 (m, 1H), 8.8 (s, 1H), 9.02 (d, 1H), 11.18 (s, 1H), 11.53 (s, 1H);

Elemental Analysis: Found C, 57.6; H, 4.4; N, 14.6; $C_{23}H_{20}ClN_5O_2$ HCl 0.5$H_2O$ requires C, 57.6; H, 4.6; N, 14.6%.

EXAMPLE 45

A mixture of 6-(2-chloroacetamido)-4-[3-methyl-4-(2-pyridylmethoxy)anilino]quinazoline (5.3 g), a solution of methylamine in ethanol (33%, 70 ml) and DMA (200 ml) was stirred at ambient temperature for 3 hours. The mixture was evaporated. Water (450 ml) and a concentrated (30%) aqueous ammonium hydroxide solution were added in turn to the residue to give a precipitate. The solid was isolated, washed with water and dried. The material so obtained was purified by column chromatography using a 10:1:0.1 mixture of methylene chloride, methanol and aqueous ammonium hydroxide solution as eluent. The material so obtained was triturated under a mixture of methylene chloride and diethyl ether. There was thus obtained 6-(2-methylaminoacetamido)-4-[3-methyl-4-(2-pyridylmethoxy) anilino]quinazoline (3.5 g), m.p. 219°–223° C.;

NMR Spectrum: 2.29 (s, 3H), 2.38 (s, 3H), 5.21 (s, 2H), 7.02 (d, 1H), 7.36 (m, 1H), 7.55 (m, 3H), 7.72 (d, 1H), 7.87 (m, 1H), 8.09 (m, 1H), 8.44 (s, 1H), 8.58 (m, 2H), 9.58 (s, 1H);

Elemental Analysis: Found C, 67.2; H, 5.5; N, 19.5; $C_{24}H_{24}N_6O_2$ requires C, 67.3; H, 5.65; N, 19.6%.

EXAMPLE 46

Using an analogous procedure to that described in Example 42 except that the reaction product was purified by column chromatography using increasingly polar mixtures of methylene chloride and methanol as eluent, 6-amino-4-[2-fluoro-4-(2-pyridylmethoxy)anilino]quinazoline was reacted with acetic anhydride to give 6-acetamido-4-[2-fluoro-4-(2-pyridylmethoxy)anilino]quinazoline, hydrochloride salt, in 16% yield;

NMR Spectrum: 2.15 (s, 3H), 5.26 (s, 2H), 6.93 (m, 1H), 7.06 (m, 1H), 7.38 (m, 2H), 7.57 (d, 1H), 7.73 (d, 1H), 7.82 (m, 1H), 7.88 (m, 1H), 8.37 (s, 1H), 8.62 (m, 2H), 9.6 (broad s, 1H), 10.23 (broad s, 1H);

Elemental Analysis: Found C, 60.1; H, 4.4; N, 15.3; $C_{22}H_{18}FN_5O_2$ HCl $0.15H_2O$ requires C; 59.7; H, 4.4; N, 15.8%.

The 6-amino-4-[2-fluoro-4-(2-pyridylmethoxy)anilino] quinazoline used as a starting material was obtained as follows:

Using an analogous procedure to that described in the first paragraph of the portion of Example 42 which is concerned with the preparation of starting materials, 4-chloro-6-nitroquinazoline was reacted with 4-amino-3-fluorophenyl 2-pyridylmethyl ether to give 4-[2-fluoro-4-(2-pyridylmethoxy)anilino]-6-nitroquinazoline in 98% yield.

A mixture of the material so obtained (12 g), 10% palladium-on-carbon (1.2 g) and ethanol (1.2 L) was heated to 50° C. and stirred under an atmosphere of hydrogen for 4 hours. The mixture was cooled to ambient temperature and filtered. The filtrate was evaporated. The residue was suspended in water and the mixture was basified by the addition of a dilute aqueous sodium carbonate solution. The resultant solid was isolated, washed with water and dried. There was thus obtained 6-amino-4-[2-fluoro-4-(2-pyridylmethoxy) anilino]quinazoline (5.3 g) which was used without further purification.

EXAMPLE 47

Using an analogous procedure to that described in Example 43, 6-amino-4-[2-fluoro-4-(2-pyridylmethoxy) anilino]quinazoline was reacted with 2-methoxyacetaldehyde dimethyl acetal to give 4-[2-fluoro-4-(2-pyridylmethoxy)anilino]-6-(2-methoxyethylamino) quinazoline in 52% yield;

NMR Spectrum: 3.33 (s, 3H), 3.35 (t, 2H), 3.57 (t, 2H), 5.22 (s, 2H), 6.13 (t, 1H), 6.94 (m, 1H), 7.05 (m, 1H), 7.19 (d, 1H), 7.29 (m, 1H), 7.38 (m, 2H), 7.5 (d, 1H), 7.56 (d, 1H), 7.86 (m, 1H), 8.19 (s, 1H), 8.62 (d, 1H), 9.18 (broad s, 1H);

Elemental Analysis: Found C, 64.0; H, 5.4; N, 15.9; $C_{23}H_{22}N_5O_2$ $0.7H_2O$ requires C, 63.9; H, 5.4; N, 16.2%.

EXAMPLE 48

Using an analogous procedure to the second paragraph of the portion of Example 42 which is concerned with the preparation of starting materials except that the reaction product was purified by column chromatography using increasingly polar mixtures of methylene chloride and methanol, 4-[3-chloro-4-(2-pyridylmethoxy)anilino]-6-nitroquinazoline was reduced with stannous chloride dihydrate to give 6-amino-4-[3-chloro-4-(2-pyridylmethoxy) anilino]quinazoline in 64% yield;

NMR Spectrum: 5.26 (s, 2H), 7.22 (m, 2H), 7.26 (m, 1H), 7.31 (d, 1H), 7.37 (m, 1H), 7.52 (d, 1H), 7.58 (d, 1H), 7.88 (m, 1H), 8.04 (d, 1H), 8.33 (s, 1H), 8.69 (m, 1H).

The 4-[3-chloro-4-(2-pyridylmethoxy)anilino]-6-nitroquinazoline used as a starting material was obtained as follows:

Using an analogous procedure to that described in the first paragraph of the portion of Example 42 which is concerned with the preparation of starting materials, 4-chloro-6-nitroquinazoline was reacted with 4-amino-2-chlorophenyl 2-pyridylmethyl ether to give the required starting material in 80% yield.

EXAMPLE 49

Using an analogous procedure to that described in Example 43, 6-amino-4-[3-chloro-4-(2-pyridylmethoxy) anilino]quinazoline was reacted with 2-methoxyacetaldehyde dimethyl acetal to give 4-[3-chloro-4-(2-pyridylmethoxy)anilino]-6-(2-methoxyethylamino) quinazoline in 67% yield;

NMR Spectrum; 3.33 (s, 3H), 3.38 (m, 2H), 3.63 (t, 2H), 5.3 (s, 2H), 6.18 (t, 1H), 7.2 (d, 1H), 7.27 (d, 1H), 7.35 (m, 2H), 7.53 (d, 1H), 7.6 (d, 1H), 7.73 (m, 1H), 7.9 (m, 1H), 7.98 (d, 1H), 8.33 (s, 1H), 8.6 (d, 1H), 9.3 (broad s, 1H);

Elemental Analysis: Found C, 60.3%; H, 4.9; N, 15.0; $C_{23}H_{22}ClN_5O_2$ $1.07H_2O$ requires C, 60.7; H, 5.3; N, 15.4%.

EXAMPLE 50

A stirred suspension of 3-morpholinopropionaldehyde dimethyl acetal (3.8 g) in water (30 ml) was acidified to pH1 by the addition of concentrated hydrochloric acid. The mixture was heated to 40° C. for 90 minutes. The mixture was brought to pH6 by the addition of a saturated aqueous sodium bicarbonate solution.

Approximately one half of this mixture was added to a stirred mixture of 6-amino-7-methoxy-4-[3-methyl-4-(2-pyridylmethoxy)anilino]quinazoline (1.16 g) and ethanol (300 ml). Sodium cyanoborohydride (0.244 g) was added and the acidity of the mixture was adjusted to pH4 to 5 by the addition of glacial acetic acid. The mixture was stirred at ambient temperature for 16 hours. A second portion of sodium cyanoborohydride (0.11 g) was added and the mixture was stirred at ambient temperature for 66 hours. The mixture was evaporated and the residue was purified by column chromatography using increasingly polar mixtures of ethyl acetate and methanol as eluent. The material so obtained was dissolved in ethyl acetate and a saturated solution of hydrogen chloride gas in ethyl acetate was added dropwise. The resultant solid was isolated, washed with ethyl acetate and with diethyl ether and dried. There was thus obtained 7-methoxy-4-[3-methyl-4-(2-pyridylmethoxy) anilino]-6-(3-morpholinopropylamino)quinazoline, trihydrochloride salt (0.85 g);

NMR Spectrum: 2.14 (t, 2H), 2.34 (s, 3H), 3.1 (m, 2H), 3.27 (t, 2H), 3.52 (m, 4H), 3.93 (m, 4H), 4.06 (s, 3H), 5.48 (s, 2H), 7.13 (d, 1H), 7.23 (s, 1H), 7.53 (m, 1H), 7.57 (s, 1H), 7.81 (m, 2H), 8.0 (d, 1H), 8.38 (m, 1H), 8.63 (s, 1H), 8.85 (d, 1H);

Elemental Analysis: Found C, 47.0; H, 6.7; N, 11.1; $C_{29}H_{34}N_6O_3$ 3HCl 6.5$H_2O$ requires C, 47.0; H, 6.8; N, 11.3%.

The 6-amino-7-methoxy-4-[3-methyl-4-(2-pyridylmethoxy)anilino]-quinazoline used as a starting material was obtained as follows:

A mixture of 4-chloroanthranilic acid (17.2 g) and formamide (10 ml) was stirred and heated to 130° C. for 45 minutes and to 175° C. for 75 minutes. The mixture was allowed to cool to approximately 100° C. and 2-(2-ethoxyethoxy)ethanol (50 ml) was added. The solution so formed was poured into a mixture (250 ml) of ice and water. The precipitate was isolated, washed with water and dried. There was thus obtained 7-chloroquinazolin-4-one (15.3 g, 85%).

A portion (6 g) of the material so obtained was added portionwise to a stirred mixture of concentrated sulphuric acid (12 ml) and fuming nitric acid (12 ml) which had been cooled to 0° C. The mixture was stirred at ambient temperature for 30 minutes and then heated to 110° C. for 30 minutes. The mixture was cooled to ambient temperature and poured onto a mixture of ice and water. The precipitate was isolated, washed with water and dried. There was thus obtained 7-chloro-6-nitroquinazolin-4-one (6.89 g).

A mixture of a portion (4 g) of the material so obtained, thionyl chloride (30 ml), phosphoryl chloride (5 ml) and DMF (10 drops) was stirred and heated to reflux for 4 hours. The mixture was evaporated. There was thus obtained 4,7-dichloro-6-nitroquinazoline as a solid which was used without further purification.

Using an analogous procedure to that described in Example 1, 4,7-dichloro-6-nitroquinazoline was reacted with 5-amino-2-tolyl 2-pyridylmethyl ether to give 7-chloro-4-[3-methyl-4-(2-pyridylmethoxy)anilino]-6-nitroquinazoline in 81% yield.

After appropriate repetition of the previous steps, sodium methoxide (11 g) was added portionwise to a stirred mixture of 7-chloro-4-[3-methyl-4-(2-pyridylmethoxy)anilino]-6-nitroquinazoline (20 g) and DMSO (200 ml) which was cooled in a water bath to approximately 18° C. The resultant mixture was stirred at ambient temperature for 4 hours. The mixture was poured slowly onto a mixture of ice and water. The precipitate was isolated to give 7-methoxy-4-[3-methyl-4-(2-pyridylmethoxy)anilino]-6-nitroquinazoline (16.5 g) which was used without further purification.

The material so obtained was reduced with stannous chloride dihydrate using an analogous procedure to that described in the second paragraph of the portion of Example 42 which is concerned with the preparation of starting materials. There was thus obtained 6-amino-7-methoxy-4-[3-methyl-4-(2-pyridylmethoxy)anilino]quinazoline in 30% yield;

NMR Spectrum: 2.26 (s, 3H), 3.97 (s, 3H), 5.2 (s, 2H), 6.97 (d, 1H), 7.06 (s, 1H), 7.35 (m, 1H), 7.42 (s, 1H), 7.55 (m, 3H), 7.85 (m, 1H), 8.08 (m, 1H), 8.25 (s, 1H), 9.04 (s, 1H).

The 3-morpholinopropionaldehyde dimethyl acetal used as a starting material was obtained as follows:

Morpholine (11.9 g) and potassium carbonate (11.3 g) were added in turn to a stirred solution of 3-bromoproionaldehyde dimethyl acetal (5 g) in toluene (80 ml) and the mixture was stirred at ambient temperature for 16 hours. The mixture was filtered and the filtrate was evaporated. The residue was purified by column chromatography using increasingly polar mixtures of methylene chloride and methanol as eluent. There was thus obtained 3-morpholinopropionaldehyde dimethyl acetal (3.82 g).

EXAMPLE 51

Using an analogous procedure to that described in Example 1 except that the product was recrystallised from a mixture of methanol and ethanol, 6-bromo-4-chloroquinazoline (European Patent Application No. 0 520 722, Example 9) was reacted with 5-amino-2-tolyl 2-pyridylmethyl ether to give 6-bromo-4-[3-methyl-4-(2-pyridylmethoxy)anilino]quinazoline, dihydrochloride salt, in 68% yield, m.p. 232°–234° C.;

NMR Spectrum: 2.3 (s, 3H), 5.35 (s, 2H), 7.13 (m, 1H), 7.52 (m, 3H), 7.63 (d, 1H), 7.9 (d, 1H), 8.08 (m, 1H), 8.25 (m, 1H), 8.7 (m, 1H), 8.92 (s, 1H), 9.17 (d, 1H), 11.62 (d, 1H);

Elemental Analysis: Found C, 48.4; H, 4.2; N, 10.6; $C_{21}H_{17}BrN_4O$ 2HCl 1.5$H_2O$ requires C, 48.4; H, 4.25; N, 10.7%.

EXAMPLE 52

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph. Eur | 488.5 |
| Magnesium stearate | 1.5 |

| (e) Injection I | (50 mg/ml) |
|---|---|
| Compound X | 5.0% w/v |
| 1M Sodium hydroxide solution | 15.0% w/v |

-continued

| | |
|---|---|
| 0.1M Hydrochloric acid (to adjust pH to 7.6) | |
| Polyethylene glycol 400 | 4.5% w/v |
| Water for injection to 100% | |
| (f) Injection II | (10 mg/ml) |
| Compound X | 1.0% w/v |
| Sodium phosphate BP | 3.6% w/v |
| 0.1M Sodium hydroxide solution | 15.0% v/v |
| Water for injection to 100% | |
| (g) Injection III | (1 mg/ml, buffered to pH6) |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

Note

The above formulations may be obtained by conventional procedures well known in the pharmaceutical art. The tablets (a)–(c) may be enteric coated by conventional means, for example to provide a coating of cellulose acetate phthalate.

CHEMICAL FORMULAE

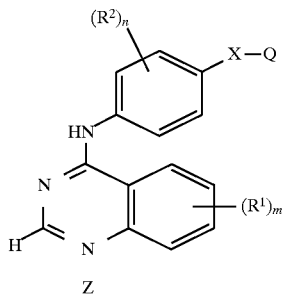

I

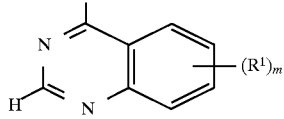

II

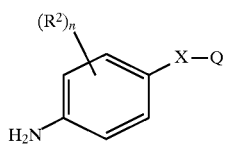

III

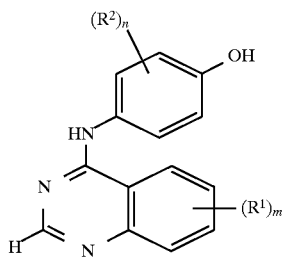

IV

We claim:
1. An aniline derivative of the formula I

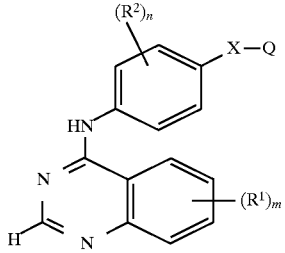

I wherein:
m is 1, 2 or 3;
each $R^1$ is independently hydroxy, amino, hydroxyamino, ureido, trifluoromethoxy, (1–4C)alkyl, (1–4C)alkoxy, (2–4C)alkanoyloxy, (2–4C)alkenyloxy, (2–4C)alkynyloxy, (1–3C)alkylenedioxy, (1–4C)alkylamino, di-[(1–4C)alkyl]amino, pyrrolidin-1-yl, piperidino, morpholino, piperazin-1-yl, 4-(1–4C)alkylpiperazin-1-yl, (1–4C)alkylthio, halogeno-(2–4C)alkoxy, hydroxy-(2–4C)alkoxy, (1–4C)alkoxy-(2–4C)alkoxy, amino-(2–4C)alkoxy, (1–4C)alkylamino-(2–4C)alkoxy, di-[(1–4C)alkyl]amino-(2–4C)alkoxy, pyrrolidin-1-yl-(2–4C)alkoxy, piperidino-(2–4C)alkoxy, morpholino-(2–4C)alkoxy, piperazin-1-yl-(2–4C)alkoxy, 4-(1–4C)alkylpiperazin-1-yl-(2–4C)alkoxy, hydroxy-(2–4C)alkylamino-(2–4C)alkoxy, di-[hydroxy-(2–4C)alkyl]amino-(2–4C)alkoxy, (1–4C)alkoxy-(2–4C)alkylamino-(2–4C)alkoxy, di-[(1–4C)alkoxy-(2–4C)alkyl]amino-(2–4C)alkoxy, amino-(2–4C)alkylamino-(2–4C)alkoxy, di-[amino-(2–4C)alkyl]amino-(2–4C)alkoxy, (1–4C)alkylamino-(2–4C)alkylamino-(2–4C)alkoxy, di-[(1–4C)alkylamino-(2–4C)alkyl]amino-(2–4C)alkoxy, di-[(1–4C)alkyl]amino-(2–4C)alkylamino-(2–4C)alkoxy, di-{di-[(1–4C)alkyl]amino-(2–4C)alkyl}amino-(2–4C)alkoxy, pyrrolidin-1-yl-(2–4C)alkylamino-(2–4C)alkoxy, piperidino-(2–4C)alkylamino-(2–4C)alkoxy, morpholino-(2–4C)alkylamino-(2–4C)alkoxy, piperazin-1-yl-(2–4C)alkylamino-(2–4C)alkoxy, 4-(1–4C)alkylpiperazin-1-yl-(2–4C)alkylamino-(2–4C)alkoxy, (1–4C)alkylthio-(2–4C)alkoxy, (1–4C)alkylsulphinyl-(2–4C)alkoxy, (1–4C)alkylsulphonyl-(2–4C)alkoxy, halogeno-(2–4C)alkylamino, hydroxy-(2–4C)alkylamino, (1–4C)alkoxy-(2–4C)alkylamino, amino-(2–4C)alkylamino, (1–4C)alkylamino-(2–4C)alkylamino, di-[(1–4C)alkyl]amino-(2–4C)alkylamino, pyrrolidin-1-yl-(2–4C)alkylamino, piperidino-(2–4C)alkylamino, morpholino-(2–4C)alkylamino, piperazin-1-yl-(2–4C)alkylamino, 4-(1–4C)alkylpiperazin-1-yl-(2–4C)alkylamino, hydroxy-(2–4C)alkylamino-(2–4C)alkylamino, di-[hydroxy-(2–4C)alkyl]amino-(2–4C)alkylamino, (1–4C)alkoxy-(2–4C)alkylamino-(2–4C)alkylamino, di-[(1–4C)alkoxy-(2–4C)alkyl]amino-(2–4C)alkylamino, amino-(2–4C)alkylamino-(2–4C)alkylamino, di-[amino-(2–4C)alkyl]amino-(2–4C)alkylamino, (1–4C)alkylamino-(2–4C)alkylamino-(2–4C)alkylamino, di-[(1–4C)alkylamino-(2–4C)alkyl]amino-(2–4C)alkylamino, di-[(1–4C)alkyl]amino-(2–4C)alkylamino-(2–4C)alkylamino, di-{di-[(1–4C)alkyl]amino-(2–4C)alkyl}amino-(2–4C)alkylamino, pyrrolidin-1-yl-(2–4C)alkylamino-(2–4C)alkylamino, piperidino-(2–4C)alkylamino-(2–4C)alkylamino, morpholino-(2–4C)alkylamino-(2–4C)alkylamino, piperazin-1-yl-(2–4C)alkylamino-(2–4C)alkylamino, 4-(1–4C)alkylpiperazin-1-yl-(2–4C)

alkylamino-(2–4C)alkylamino, N-(1–4C)alkyl-halogeno-(2–4C)alkylamino, N-(1–4C)alkyl-hydroxy-(2–4C)alkylamino, N-(1–4C)alkyl-(1–4C)alkoxy-(2–4C)alkylamino, di-[halogeno-(2–4C)alkyl]amino, di-[hydroxy-(2–4C)alkyl]amino, di-[(1–4C)alkoxy-(2–4C)alkyl]amino, (2–4C)alkanoylamino, 2-oxopyrrolidin-1-yl, 2-oxopiperidin-1-yl, halogeno-(2–4C)alkanoylamino, hydroxy-(2–4C)alkanoylamino, (1–4C)alkoxy-(2–4C)alkanoylamino, (3–4C)alkenoylamino, (3–4C)alkynoylamino, (2–4C)alkanoyloxy-(2–4C)alkanoylamino, amino-(2–4C)alkanoylamino, (1–4C)alkylamino-(2–4C)alkanoylamino, di-[(1–4C)alkyl]amino-(2–4C)alkanoylamino, pyrrolidin-1-yl-(2–4C)alkanoylamino, piperidino-(2–4C)alkanoylamino, morpholino-(2–4C)alkanoylamino, piperazin-1-yl-(2–4C)alkanoylamino, 4-(1–4C)alkylpiperazin-1-yl-(2–4C)alkanoylamino, (1–4C)alkylthio-(2–4C)alkanoylamino, (1–4C)alkylsulphinyl-(2–4C)alkanoylamino, (1–4C)alkylsulphonyl-(2–4C)alkanoylamino, N-(1–4C)alkyl-(2–4C)alkanoylamino, N-(1–4C)alkyl-halogeno-(2–4C)alkanoylamino, N-(1–4C)alkyl-hydroxy-(2–4C)alkanoylamino, N-(1–4C)alkyl-(1–4C)alkoxy-(2–4C)alkanoylamino, N-(1–4C)alkyl-(3–4C)alkenoylamino or N-(1–4C)alkyl-(3–4C)alkynoylamino, and wherein any of the above-mentioned $R^1$ substituents comprising a $CH_2$ (methylene) group which is not attached to a halogeno, SO or $SO_2$ group or to a N, O or S atom optionally bears on said $CH_2$ group a substituent selected from hydroxy, amino, (1–4C)alkoxy, (1–4C)alkylamino and di-[(1–4C)alkyl]amino;

n is 0, 1, 2 or 3;

each $R^2$ is independently halogeno, trifluoromethyl, hydroxy, amino, nitro, cyano, (1–4C)alkyl, (1–4C)alkoxy, (1–4C)alkylamino, di-[(1–4C)alkyl]amino or (2–4C)alkanoylamino;

X is a group of the formula CO, $C(R^3)_2$, $CH(OR^3)$, $C(R^3)_2$—$C(R^3)_2$, $C(R^3)$=$C(R^3)$, C≡C, CH(CN), O, S, SO, $SO_2$, $CONR^3$, $SO_2NR^3$, $NR^3CO$, $NR^3SO_2$, $OC(R^3)_2$, $SC(R^3)_2$, $C(R^3)_2O$ or $C(R^3)_2S$ wherein each $R^3$ is independently hydrogen or (1–4C)alkyl; and Q is a phenyl or naphthyl group or a 5- or 6-membered heteroaryl moiety containing 1, 2 or 3 heteroatoms selected from oxygen, nitrogen and sulphur, which heteroaryl moiety is a single ring or is fused to a benzo ring, and wherein said phenyl or naphthyl group or heteroaryl moiety is optionally substituted with 1, 2 or 3 substituents selected from halogeno, trifluoromethyl, cyano, carbamoyl, hydroxy, amino, nitro, (1–4C)alkyl, (1–4C)alkoxy, (1–4C)alkylamino, di-[(1–4C)alkyl]amino, (2–4C)alkanoylamino, N-(1–4C)alkylcarbamoyl and N,N-di-[(1–4C)alkyl]carbamoyl;

or a pharmaceutically-acceptable salt thereof.

2. An aniline derivative of the formula I

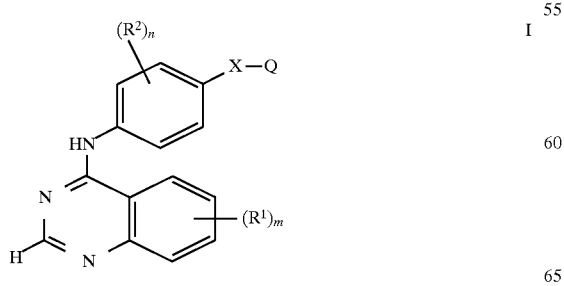

wherein:
m is 1, 2 or 3;

each $R^1$ is independently halogen, hydroxy, amino, hydroxyamino, ureido, trifluoromethoxy, (1–4C)alkyl, (1–4C)alkoxy, (2–4C)alkanoyloxy, (2–4C)alkenyloxy, (2–4C)alkynyloxy, (1–3C)alkylenedioxy, (1–4C)alkylamino, di-[(1–4C)alkyl]amino, pyrrolidin-1-yl, piperidino, morpholino, piperazin-1-yl, 4-(1–4C)alkylpiperazin-1-yl, (1–4C)alkylthio, halogeno-(2–4C)alkoxy, hydroxy-(2–4C)alkoxy, (1–4C)alkoxy-(2–4C)alkoxy, amino-(2–4C)alkoxy, (1–4C)alkylamino-(2–4C)alkoxy, di-[(1–4C)alkyl]amino-(2–4C)alkoxy, pyrrolidin-1-yl-(2–4C)alkoxy, piperidino-(2–4C)alkoxy, morpholino-(2–4C)alkoxy, piperazin-1-yl-(2–4C)alkoxy, 4-(1–4C)alkylpiperazin-1-yl-(2–4C)alkoxy, hydroxy-(2–4C)alkylamino-(2–4C)alkoxy, di-[hydroxy-(2–4C)alkyl]amino-(2–4C)alkoxy, (1–4C)alkoxy-(2–4C)alkylamino-(2–4C)alkoxy, di-[(1–4C)alkoxy-(2–4C)alkyl]amino-(2–4C)alkoxy, amino-(2–4C)alkylamino-(2–4C)alkoxy, di-[amino-(2–4C)alkyl]amino-(2–4C)alkoxy, (1–4C)alkylamino-(2–4C)alkylamino-(2–4C)alkoxy, di-[(1–4C)alkylamino-(2–4C)alkyl]amino-(2–4C)alkoxy, di-[(1–4C)alkyl]amino-(2–4C)alkylamino-(2–4C)alkoxy, di-{di-[(1–4C)alkyl]amino-(2–4C)alkyl}amino-(2–4C)alkoxy, pyrrolidin-1-yl-(2–4C)alkylamino-(2–4C)alkoxy, piperidino-(2–4C)alkylamino-(2–4C)alkoxy, morpholino-(2–4C)alkylamino-(2–4C)alkoxy, piperazin-1-yl-(2–4C)alkylamino-(2–4C)alkoxy, 4-(1–4C)alkylpiperazin-1-yl-(2–4C)alkylamino-(2–4C)alkoxy, (1–4C)alkylthio-(2–4C)alkoxy, (1–4C)alkylsulphinyl-(2–4C)alkoxy, (1–4C)alkylsulphonyl-(2–4C)alkoxy, halogeno-(2–4C)alkylamino, hydroxy-(2–4C)alkylamino, (1–4C)alkoxy-(2–4C)alkylamino, amino-(2–4C)alkylamino, (1–4C)alkylamino-(2–4C)alkylamino, di-[(1–4C)alkyl]amino-(2–4C)alkylamino, pyrrolidin-1-yl-(2–4C)alkylamino, piperidino-(2–4C)alkylamino, morpholino-(2–4C)alkylamino, piperazin-1-yl-(2–4C)alkylamino, 4-(1–4C)alkylpiperazin-1-yl-(2–4C)alkylamino, hydroxy-(2–4C)alkylamino-(2–4C)alkylamino, di-[hydroxy-(2–4C)alkyl]amino-(2–4C)alkylamino, (1–4C)alkoxy-(2–4C)alkylamino-(2–4C)alkylamino, di-[(1–4C)alkoxy-(2–4C)alkyl]amino-(2–4C)alkylamino, amino-(2–4C)alkylamino-(2–4C)alkylamino, di-[amino-(2–4C)alkyl]amino-(2–4C)alkylamino, (1–4C)alkylamino-(2–4C)alkylamino-(2–4C)alkylamino, di-[(1–4C)alkylamino-(2–4C)alkyl]amino-(2–4C)alkylamino, di-[(1–4C)alkyl]amino-(2–4C)alkylamino-(2–4C)alkylamino, di-{di-[(1–4C)alkyl]amino-(2–4C)alkyl}amino-(2–4C)alkylamino, pyrrolidin-1-yl-(2–4C)alkylamino-(2–4C)alkylamino, piperidino-(2–4C)alkylamino-(2–4C)alkylamino, morpholino-(2–4C)alkylamino-(2–4C)alkylamino, piperazin-1-yl-(2–4C)alkylamino-(2–4C)alkylamino, 4-(1–4C)alkylpiperazin-1-yl-(2–4C)alkylamino-(2–4C)alkylamino, N-(1–4C)alkyl-halogeno-(2–4C)alkylamino, N-(1–4C)alkyl-hydroxy-(2–4C)alkylamino, N-(1–4C)alkyl-(1–4C)alkoxy-(2–4C)alkylamino, di-[halogeno-(2–4C)alkyl]amino, di-[hydroxy-(2–4C)alkyl]amino, di-[(1–4C)alkoxy-(2–4C)alkyl]amino, (2–4C)alkanoylamino, 2-oxopyrrolidin-1-yl, 2-oxopiperidin-1-yl, halogeno-(2–4C)alkanoylamino, hydroxy-(2–4C)alkanoylamino, (1–4C)alkoxy-(2–4C)alkanoylamino, (3–4C)alkenoylamino, (3–4C)alkynoylamino, (2–4C)alkanoyloxy-(2–4C)alkanoylamino, amino-(2–4C)alkanoylamino, (1–4C)alkylamino-(2–4C)alkanoylamino, di-[(1–4C)alkyl]amino-(2–4C)alkanoylamino, pyrrolidin-1-yl-(2–4C)alkanoylamino, piperidino-(2–4C)alkanoylamino, morpholino-(2–4C)

alkanoylamino, piperazin-1-yl-(2–4C)alkanoylamino, 4-(1–4C)alkylpiperazin-1-yl-(2–4C)alkanoylamino, (1–4C)alkylthio-(2–4C)alkanoylamino, (1–4C)alkylsulphinyl-(2–4C)alkanoylamino, (1–4C)alkylsulphonyl-(2–4C)alkanoylamino, N-(1–4C)alkyl-(2–4C)alkanoylamino, N-(1–4C)alkyl-halogeno-(2–4C)alkanoylamino, N-(1–4C)alkyl-hydroxy-(2–4C)alkanoylamino, N-(1–4C)alkyl-(1–4C)alkoxy-(2–4C)alkanoylamino, N-(1–4C)alkyl-(3–4C)alkenoylamino or N-(1–4C)alkyl-(3–4C)alkynoylamino, and wherein any of the above-mentioned $R^1$ substituents comprising a $CH_2$ (methylene) group which is not attached to a halogeno, SO or $SO_2$ group or to a N, O or S atom optionally bears on said $CH_2$ group a substituent selected from hydroxy, amino, (1–4C)alkoxy, (1–4C)alkylamino and di-[(1–4C)alkyl]amino;

n is 0, 1, 2 or 3;

each $R^2$ is independently halogeno, trifluoromethyl, hydroxy, amino, nitro, cyano, (1–4C)alkyl, (1–4C)alkoxy, (1–4C)alkylamino, di-[(1–4C)alkyl]amino or (2–4C)alkanoylamino;

X is a group of the formula CO, $C(R^3)_2$, $CH(OR^3)$, $C(R^3)_2$—$C(R^3)_2$, $C(R^3)$=$C(R^3)$, C≡C, CH(CN), O, S, SO, $SO_2$, $CONR^3$, $SO_2NR^3$, $NR^3CO$, $NR^3SO_2$, $SC(R^3)_2$, $C(R^3)_2O$ or $C(R^3)_2S$ wherein each $R^3$ is independently hydrogen or (1–4C)alkyl; and Q is a phenyl or naphthyl group or a 5- or 6-membered heteroaryl moiety containing 1, 2 or 3 heteroatoms selected from oxygen, nitrogen and sulphur, which heteroaryl moiety is a single ring or is fused to a benzo ring, and wherein said phenyl or naphthyl group or heteroaryl moiety is optionally substituted with 1, 2 or 3 substituents selected from halogeno, trifluoromethyl, cyano, carbamoyl, hydroxy, amino, nitro, (1–4C)alkyl, (1–4C)alkoxy, (1–4C)alkylamino, di-[(1–4C)alkyl] amino, (2–4C)alkanoylamino, N-(1–4C)alkylcarbamoyl and N,N-di-[(1–4C)alkyl]carbamoyl; or a pharmaceutically-acceptable salt thereof.

3. An aniline derivative of the formula I

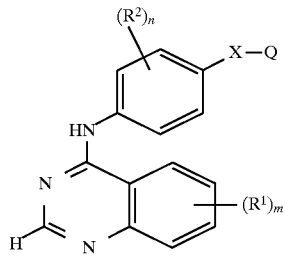

wherein m is 1 with the substituent located at the 6-position, or m is 2 with the substituents located at the 6- and 7-positions;

each $R^1$ is fluoro, chloro, bromo, hydroxy, amino, methoxy, ethoxy, acetoxy, methylamino, ethylamino, 2-bromoethoxy, 2,2,2-trifluoroethoxy, 2-hydroxyethoxy, 2-methoxyethoxy, 2-ethoxyethoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-(piperazin-1-yl)ethoxy, 3-(piperazin-1-yl)propoxy, 2-(4-methylpiperazin-1-yl)ethoxy, 3-(4-methylpiperazin-1-yl)propoxy, 2-hydroxyethylamino, 2-methoxyethylamino, 2-ethoxyethylamino, 3-methoxypropylamino, 2-dimethylaminoethylamino, 3-dimethylaminopropylamino, 2-(pyrrolidin-1-yl)ethylamino, 3-(pyrrolidin-1-yl)propylamino, 2-piperidinoethylamino, 3-piperidinopropylamino, 2-morpholinoethylamino, 3-morpholinopropylamino, 2-(piperazin-1-yl)ethylamino, 3-(piperazin-1-yl)propylamino, 2-(4-methylpiperazin-1-yl)ethylamino, 3-(4-methylpiperazin-1-yl)propylamino, acetamido, 2-chloroacetamido, 2-methylaminoacetamido, 2-ethylaminoacetamido, 2-dimethylaminoacetamido or 2-diethylaminoacetamido, or $(R^1)_m$ is a 6,7-methylenedioxy group;

n is 0, 1 or 2;

each $R^2$ is independently fluoro, chloro, bromo, cyano, methyl or ethyl;

X is a group of the formula CO, $C(R^3)_2$, $CH(OR^3)$, O, S, $SO_2$, $CONR^3$, $SO_2NR^3$, $NR^3CO$, $NR^3SO_2$, $OC(R^3)_2$ or $SC(R^3)_2$ wherein each $R^3$ is independently hydrogen or methyl; and Q is a phenyl group which is optionally substituted with 1 or 2 substituents selected from fluoro, chloro, bromo, trifluoromethyl, cyano, carbamoyl, methyl and methoxy, or Q is a 5- or 6-membered heteroaryl moiety selected from furyl, thienyl, oxazolyl, imidazolyl, thiazolyl, pyridyl, pyrimidinyl and 1,2,4-triazolyl which is optionally substituted with 1 or 2 substituents selected from fluoro, chloro, methyl, ethyl, methoxy and ethoxy;

or a pharmaceutically-acceptable salt thereof.

4. An aniline derivative of the formula I as claimed in claim 1 wherein m is 1 with the substituent located at the 6-position or m is 2 with the substituents located at the 6- and 7-positions and each $R^1$ is hydroxy, amino, methoxy, ethoxy, acetoxy, methylamino, ethylamino, 2-bromoethoxy, 2,2,2-trifluoroethoxy, 2-hydroxyethoxy, 2-methoxyethoxy, 2-ethoxyethoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-hydroxyethylamino, 2-methoxyethylamino, 2-ethoxyethylamino, acetamido, 2-chloroacetamido, 2-methylaminoacetamido, 2-ethylaminoacetamido, 2-dimethylaminoacetamido or 2-diethylaminoacetamido, or $(R^1)_m$ is a 6,7-methylenedioxy group;

n is 0 or n is 1 and $R^2$ is fluoro, chloro, cyano, methyl or ethyl;

X is a group of the formula CO, $C(R^3)_2$, $CH(OR^3)$, O, S, $SO_2$, $CONR^3$, $SO_2NR^3$, $OC(R^3)_2$ or $SC(R^3)_2$ wherein each $R^3$ is independently hydrogen or methyl; and Q is a phenyl group which is optionally substituted with 1 or 2 substituents selected from fluoro, chloro, bromo, trifluoromethyl, cyano and carbamoyl, or Q is a 5- or 6-membered heteroaryl moiety selected from furyl, thienyl, pyridyl, oxazolyl, imidazolyl, thiazolyl, pyrimidinyl and 1,2,4-triazolyl which is optionally substituted with 1 or 2 substituents selected from fluoro, chloro, methyl, ethyl, methoxy and ethoxy;

or a pharmaceutically-acceptable salt thereof.

5. An aniline derivative of the formula I as claimed in claim 1
wherein m is 1 or 2 and each $R^1$ is hydroxy, methoxy, ethoxy, 2-hydroxyethoxy, 2-methoxyethoxy, 2-methylaminoethoxy or 2-dimethylaminoethoxy, or $(R^1)_m$ is a methylenedioxy group;

n is 0 or n is 1 and $R^2$, which is located ortho to the group of formula —X—Q, is fluoro, chloro, cyano, methyl or ethyl;

X is a group of the formula CO, $C(R^3)_2$, $CH(OR^3)$, O, S, $SO_2$, $CONR^3$, $SO_2NR^3$, $OC(R^3)_2$ or $SC(R^3)_2$ wherein each $R^3$ is independently hydrogen or methyl; and Q is a phenyl group which is optionally substituted with 1 or 2 substituents selected from fluoro, chloro, bromo, trifluoromethyl, cyano and carbamoyl, or Q is a 5- or 6-membered heteroaryl moiety selected from furyl, thienyl, pyridyl, oxazolyl, imidazolyl, thiazolyl, pyrimidinyl and 1,2,4-triazolyl which is optionally substituted with a substituent selected from methyl and ethyl;

or a pharmaceutically-acceptable salt thereof.

6. An aniline derivative of the formula I as claimed in claim 1 wherein m is 1 with the substituent located at the 6-position or m is 2 with the substituents located at the 6- and 7-positions and each $R^1$ is hydroxy, amino, methoxy, ethoxy, acetoxy, methylamino, ethylamino, 2-bromoethoxy, 2,2,2-trifluoroethoxy, 2-hydroxyethoxy, 2-methoxyethoxy, 2-methylaminoethoxy, 3-methylaminopropoxy, 2-dimethylaminoethoxy, 3-dimethylaminopropoxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-(piperazin-1-yl)ethoxy, 3-(piperazin-1-yl)propoxy, 2-(4-methylpiperazin-1-yl)ethoxy, 3-(4-methylpiperazin-1-yl)propoxy, 2-hydroxyethylamino, 2-methoxyethylamino, 3-methoxypropylamino, 2-dimethylaminoethylamino, 3-dimethylaminopropylamino, 2-(pyrrolidin-1-yl)ethylamino, 3-(pyrrolidin-1-yl)propylamino, 2-piperidinoethylamino, 3-piperidinopropylamino, 2-morpholinoethylamino, 3-morpholinopropylamino, 2-(piperazin-1-yl)ethylamino, 3-(piperazin-1-yl)propylamino, 2-(4-methylpiperazin-1-yl)ethylamino, 3-(4-methylpiperazin-1-yl)propylamino, acetamido, 2-chloroacetamido, 2-methylaminoacetamido, 2-ethylaminoacetamido, 2-dimethylaminoacetamido or 2-diethylaminoacetamido, or $(R^1)_m$ is a 6,7-methylenedioxy group;

n is 0, 1 or 2 and each $R^2$ is independently fluoro, chloro, bromo, cyano, methyl or ethyl;

X is a group of the formula CO, $CH_2$, CH(OH), O, S, $SO_2$, CONH, $SO_2NH$, NHCO, $NHSO_2$ or $OCH_2$; and Q is a phenyl group which is optionally substituted with 1 or 2 substituents selected from fluoro, chloro, bromo, trifluoromethyl, cyano, carbamoyl, methyl and methoxy, or Q is a 5- or 6-membered heteroaryl moiety selected from furyl, thienyl, oxazolyl, imidazolyl, thiazolyl and pyridyl which is optionally substituted with 1 or 2 substituents selected from fluoro, chloro, methyl, ethyl, methoxy and ethoxy;

or a pharmaceutically-acceptable salt thereof.

7. An aniline derivative of the formula I as claimed in claim 1 wherein $(R^1)_m$ is 6,7-dimethoxy;

n is 1 and $R^2$, which is located ortho to the group of formula —X—Q, is fluoro, chloro or methyl.

X is a group of the formula CO, $CH_2$, CH(OH), O, S, $SO_2$, CONH, $SO_2NH$ or $OCH_2$; and Q is a phenyl group which is optionally substituted with 1 or 2 substituents selected from fluoro, chloro, trifluoromethyl, cyano and carbamoyl, or Q is 2-furyl, 3-furyl, 2-thienyl, 3-thienyl, 2-pyridyl, 3-pyridyl, 4-pyridyl, 2-oxazolyl, 4-oxazolyl, 5-oxazolyl, 2-imidazolyl, 1-methylimidazol-2-yl, 4-imidazolyl, 1-methylimidazol-4-yl, 5-imidazolyl, 1-methylimidazol-5-yl, 2-thiazolyl, 4-thiazolyl or 5-thiazolyl;

or a pharmaceutically-acceptable acid-addition salt thereof.

8. An aniline derivative of the formula I as claimed in claim 1 wherein $(R^1)_m$ is 6,7-dimethoxy, 6-methoxy-7-(2,2,2-trifluoroethoxy), 6-(2-dimethylaminoethoxy)-7-methoxy, 6-(3-dimethylaminopropoxy)-7-methoxy, 6-(2-morpholinoethoxy)-7-methoxy, 6-(3-morpholinopropoxy)-7-methoxy, 6-(2-dimethylaminoethoxy), 6-(3-dimethylaminopropoxy), 6-(2-morpholinoethoxy), 6-(3-morpholinopropoxy), 6-amino, 6-acetamido, 6-(2-chloroacetamido), 6-(2-methylaminoacetamido), 6-(2-methoxyethylamino), 6-(2-dimethylaminoethylamino)-7-methoxy, 6-(3-dimethylaminopropylamino)-7-methoxy, 6-(2-morpholinoethylamino)-7-methoxy or 6-(3-morpholinopropylamino)-7-methoxy;

n is 1 or 2 and $R^2$ is fluoro, chloro or methyl;

X is a group of formula $OCH_2$; and

Q is 2-furyl, 3-furyl, 2-thienyl, 2-pyridyl or 1-methylimidazol-2-yl;

or a pharmaceutically-acceptable acid-addition salt thereof.

9. An aniline derivative of the formula I as claimed in claim 1 wherein $(R^1)_m$ is 6,7-dimethoxy;

n is 1 and $R^2$ is fluoro, chloro or methyl;

X is a group of the formula $OCH_2$; and

Q is 2-furyl, 3-furyl, 2-thienyl, 2-pyridyl or 1-methylimidazol-2-yl;

or a pharmaceutically-acceptable acid-addition salt thereof.

10. An aniline derivative of the formula I as claimed in claim 1 selected from:

4-(4-benzoyl-3-chloroanilino)-6,7-dimethoxyquinazoline,

4-{3-chloro-4-[1-hydroxy-1-(4-pyridyl)methyl]anilino}-6,7-dimethoxyquinazoline, 4-(4-benzyl-3-chloroanilino)-6,7-dimethoxyquinazoline, 4-(3-chloro-4-phenylthioanilino)-6,7-dimethoxyquinazoline, 4-[3-chloro-4-(1-methylimidazol-2-ylthio)anilino]-6,7-dimethoxyquinazoline, 6,7-dimethoxy-4-[4-(N-phenylsulphamoyl)anilino]quinazoline, 6,7-dimethoxy-4-[3-methyl-4-(2-pyridylmethoxy)anilino]quinazoline, 4-[3-chloro-4-(4-fluorobenzoyl)anilino]-6,7-dimethoxyquinazoline, 4-[2-fluoro-4-(2-pyridylmethoxy)anilino]-6,7-dimethoxyquinazoline, 4-[3-fluoro-4-(2-pyridylmethoxy)anilino]-6,7-dimethoxyquinazoline, 4-[3-chloro-4-(2-pyridylmethoxy)anilino]-6,7-dimethoxyquinazoline, 4-[3-chloro-4-(1-methylimidazol-2-ylmethoxy)anilino]-6,7-dimethoxyquinazoline, 6,7-dimethoxy-4-[3-methyl-4-(1-methylimidazol-2-ylmethoxy)anilino]quinazoline, 6,7-dimethoxy-4-[3-methyl-4-(2-thiazolylmethoxy)anilino]quinazoline, 4-[3-fluoro-4-(2-pyridylmethoxy)anilino]-6,7-dimethoxyquinazoline, 4-[2-fluoro-4-(2-pyridylmethoxy)anilino]-6-(3-morpholinopropoxy)quinazoline, 6-(3-dimethylaminopropoxy)-7-methoxy-4-[3-methyl-4-(2-pyridylmethoxy)anilino]quinazoline, 7-methoxy-4-[3-methyl-4-(2-pyridylmethoxy)anilino]-6-(3-morpholinopropoxy)quinazoline or 4-[2-fluoro-4-(2-pyridylmethoxy)anilino]-6-(2-methoxyethylamino)quinazoline;

or a pharmaceutically-acceptable acid-addition salt thereof.

11. A process for the preparation of an aniline derivative of the formula I, or a pharmaceutically-acceptable salt thereof, as claimed in any one of claims 1, 2, 3 and 4 to 10 which comprises:

(a) the reaction of a quinazoline derivative of the formula II

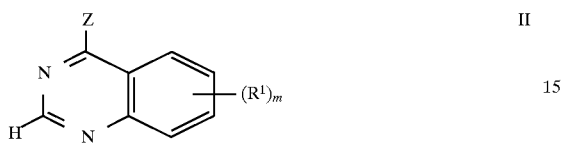

wherein Z is a displaceable group, with an aniline of the formula III,

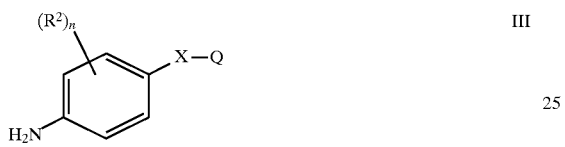

(b) for the production of those compounds of the formula I wherein $R^1$ or $R^2$ is hydroxy, the cleavage of an aniline derivative of the formula I wherein $R^1$ or $R^2$ is (1–4C)alkoxy;

(c) for the production of those compounds of the formula I wherein $R^1$ is amino or hydroxyamino, the reduction of an aniline derivative of the formula I wherein $R^1$ is nitro;

(d) for the production of those compounds of the formula I wherein $R^1$ is (2–4C)alkanoylamino, substituted (2–4C)alkanoylamino, (3–4C)alkenoylamino, (3–4C)alkynoylamino, N-(1–4C)alkyl-(2–4C)alkanoylamino, substituted N-(1–4C)alkyl-(2–4C)-alkanoylamino, N-(1–4C)alkyl-(3–4C)alkenoylamino or N-(1–4C)alkyl-(2–4C)alkynoylamino or $R^2$ is (2–4C)alkanoylamino, the acylation of an aniline derivative of the formula I wherein $R^1$ or $R^2$ is amino;

(e) for the production of those compounds of the formula I wherein $R^1$ is (1–4C)alkoxy or substituted (1–4C)alkoxy or $R^1$ is (1–4C)alkylamino, di-[(1–4C)alkyl]amino or substituted (1–4C)alkylamino, the alkylation of an aniline derivative of the formula I wherein $R^1$ is hydroxy or amino as appropriate;

(f) for the production of those compounds of the formula I wherein X is a group of the formula CH(OH) or $CH_2$, the reduction of a compound of the formula I wherein X is a group of the formula CO;

(g) for the production of those compounds of the formula I wherein X is a group of the formula SO or $SO_2$, the oxidation of an aniline derivative of the formula I wherein X is a group of the formula S;

(h) for the production of those compounds of the formula I wherein $R^1$ is (2–4C)alkanoyloxy, the acylation of an aniline derivative of the formula I wherein $R^1$ is hydroxy;

(i) for the production of those compounds of the formula I wherein $R^1$ is hydroxy, the hydrolysis of an aniline derivative of the formula I wherein $R^1$ is (2–4C)alkanoyloxy;

(j) for the production of those compounds of the formula I wherein $R^1$ is a (2–4C)alkoxy group which bears a hydroxy, amino, substituted hydroxy or substituted amino group, the reaction of a compound of the formula I wherein $R^1$ is a hydroxy-(2–4C)alkoxy group, or a reactive derivative thereof, with water, ammonia, an alcohol or an amine as appropriate;

(k) for the production of those compounds of the formula I wherein X is a group of the formula $OC(R^3)_2$, the alkylation of a phenol of the formula IV

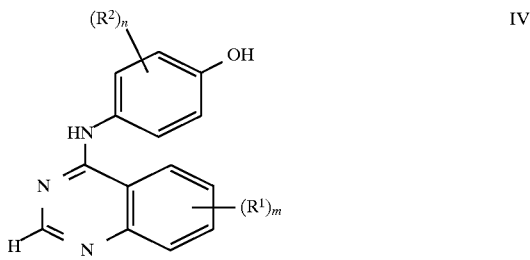

with an alkylating agent of the formula $Z-C(R^3)_2-Q$ wherein Z is a displaceable group; or (l) for the production of those compounds of the formula I wherein $R^1$ is (1–4C)alkylamino or substituted (2–4C)alkylamino, the reductive amination of formaldehyde, a (2–4C)alkanoaldehyde or a substituted (2–4C)alkanoaldehyde;

and when a pharmaceutically-acceptable salt of an aniline derivative of the formula I is required it may be obtained using a conventional procedure.

12. A pharmaceutical composition which comprises an aniline derivative of the formula I, or a pharmaceutically-acceptable salt thereof, as claimed in any one of claims 1, 2, 3 and 4 to 10 in association with a pharmaceutically-acceptable diluent or carrier.

13. A method for producing an anti-proliferative effect in a warm-blooded animal in need of such treatment which comprises administering to said animal an effective amount of an aniline derivative of the formula I, or a pharmaceutically-acceptable salt thereof, as claimed in any one of claims 1, 2, 3 and 4 to 10.

* * * * *